United States Patent
Kiiver et al.

(10) Patent No.: US 9,474,800 B2
(45) Date of Patent: Oct. 25, 2016

(54) EXPRESSION VECTOR ENCODING ALPHAVIRUS REPLICASE AND THE USE THEREOF AS IMMUNOLOGICAL ADJUVANT

(75) Inventors: Kaja Kiiver, Tartu (EE); Rein Sikut, Tartu (EE); Urve Toots, Tartu (EE); Tarmo Mölder, Tartu (EE); Andres Männik, Tartu (EE); Mart Ustav, Tartu (EE); Katrin Kaldma, Tartu (EE)

(73) Assignee: FIT Biotech OY, Tampere (FI)

( * ) Notice: Subject to any disclaimer, the term of this patent is extended or adjusted under 35 U.S.C. 154(b) by 834 days.

(21) Appl. No.: 12/993,987

(22) PCT Filed: May 22, 2009

(86) PCT No.: PCT/EP2009/056240
§ 371 (c)(1),
(2), (4) Date: Jan. 28, 2011

(87) PCT Pub. No.: WO2009/141434
PCT Pub. Date: Nov. 26, 2009

(65) Prior Publication Data
US 2011/0171255 A1 Jul. 14, 2011

Related U.S. Application Data

(60) Provisional application No. 61/071,898, filed on May 23, 2008.

(51) Int. Cl.
| | | |
|---|---|---|
| A61K 39/00 | (2006.01) | |
| A61K 48/00 | (2006.01) | |
| A61K 39/39 | (2006.01) | |
| C07K 14/005 | (2006.01) | |
| C12N 7/00 | (2006.01) | |
| C12N 9/12 | (2006.01) | |

(52) U.S. Cl.
CPC ............ *A61K 39/39* (2013.01); *C07K 14/005* (2013.01); *C12N 7/00* (2013.01); *C12N 9/127* (2013.01); *A61K 2039/53* (2013.01); *A61K 2039/55516* (2013.01); *C07K 2319/09* (2013.01); *C12N 2710/20022* (2013.01); *C12N 2770/36122* (2013.01)

(58) Field of Classification Search
None
See application file for complete search history.

(56) References Cited

U.S. PATENT DOCUMENTS

| | | | | |
|---|---|---|---|---|
| 5,684,136 A | * | 11/1997 | Godowski | ............ 530/399 |
| 2004/0136982 A1 | * | 7/2004 | Tahara | ............ 424/143.1 |
| 2005/0026137 A1 | * | 2/2005 | Krohn et al. | ............ 435/5 |

FOREIGN PATENT DOCUMENTS

| | | | |
|---|---|---|---|
| WO | WO9527044 | * | 10/1995 |
| WO | WO 01/30989 | | 5/2001 |
| WO | WO2006085983 | * | 8/2006 |

OTHER PUBLICATIONS

GenBank: CAB62256.1 by Tuittila et al., 2000 SFV nsP1234 polyprotein seq: submitted as a part of publication: Replicase Complex genes of Semilik Forest Virus confer lethal neurovirulence. J.Virol.74 (10), 4579-4589.*
Nasar et al., 2012. Eilat virus, a unique alphavirus with host range restricted to insects by RNA replication PNAS, vol. 109 (36), 14622-14627.*
Barouch et al.2008. Challenges in the development of HIV1 vaccine. Nature. vol. 455, 613-619.*
Nikonov et al. RIG-I and MDA-5 detection of viral RNA-dependent RNA polymerase activity restricts positive-strand RNA virus replication. PLoS Pathog. 2013;9(9): p. 1-23.*
Thompson et al. Mucosal and systemic adjuvant activity of alphavirus replicon particles. 3722-3727_PNAS_Mar. 7, 2006_ vol. 103_No. 10.*
Forrester et al. Genome-Scale Phylogeny of the Alphavirus Genus Suggests a Marine Origin. J Virol. Mar. 2012; 86(5): 2729-2738.*
Kujala et al. Monoclonal antibodies specific for Semliki Forest virus replicase protein nsP2. J Gen Virol. Feb. 1997;78 ( Pt 2):343-51.*
Campbell. Laboratory techniques in biochemistry and molecular biology. "Monoclonal Antibody Technology. The production and characterization of rodent and human hybridomas." 1984, vol. 13, Chapter 1, p. 1-32. Elsevier.*
Strauss and Strauss. The alphaviruses: gene expression, replication, and evolution. Microbiol Rev. Sep. 1994;58(3):491-562.*
Baker et al., Protein Structure Predication and Structural Genomics, Science (2001) vol. 294, No. 5540, pp. 93-96.*
Attwood, T. The Babel of Bioinformatics, Science (2000) vol. 290, No. 5491, pp. 471-473.*

(Continued)

*Primary Examiner* — Michelle S Horning
(74) *Attorney, Agent, or Firm* — Buchanan Ingersoll & Rooney PC

(57) ABSTRACT

The present invention relates to an alphaviral replicase, especially Semliki Forest Virus replicase, or an expression vector encoding an alphaviral replicase, said alphaviral replicase comprising RNA dependent RNA polymerase activity, for use as an immune system modulating adjuvant. The alphaviral replicase may be used in the combination with a vaccine providing an adjuvant function therein, which when present therein will generate an additional boost to the immune response in the subject to whom this combination is administered as compared to when the vaccine alone is administered to a subject in need thereof. The aim of the present invention is to provide an efficient and easy to administer, species-independent adjuvant which will provide advantages to the adjuvants used together with vaccines today.

27 Claims, 9 Drawing Sheets

(56) References Cited

OTHER PUBLICATIONS

Figure 2:
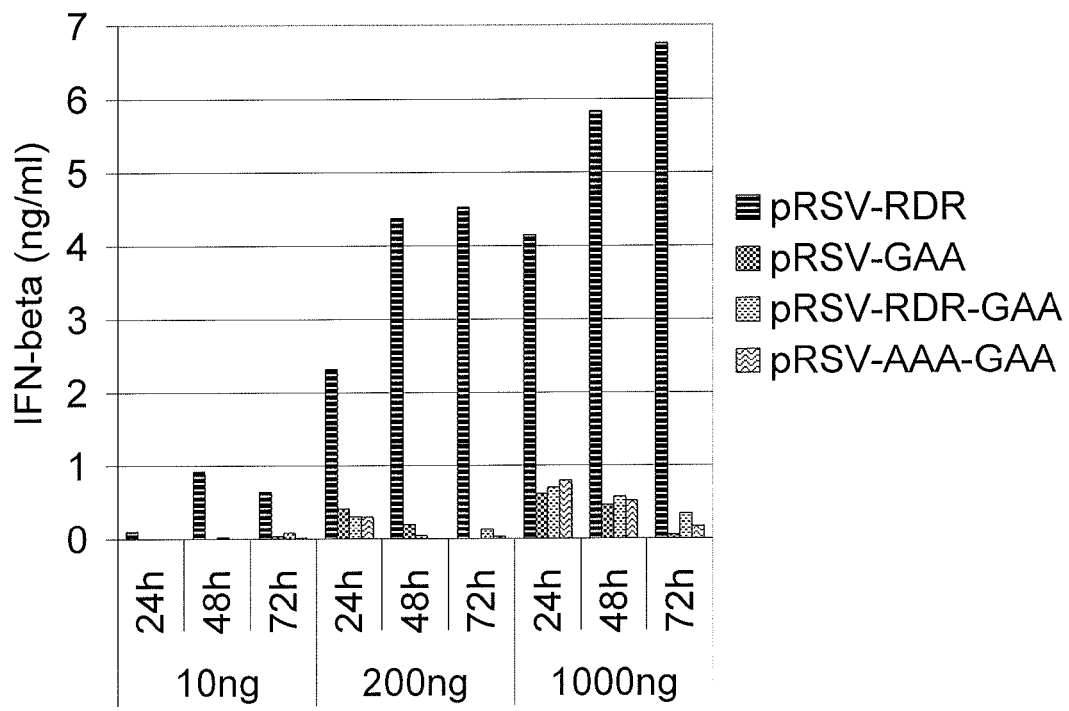
Figure 3:
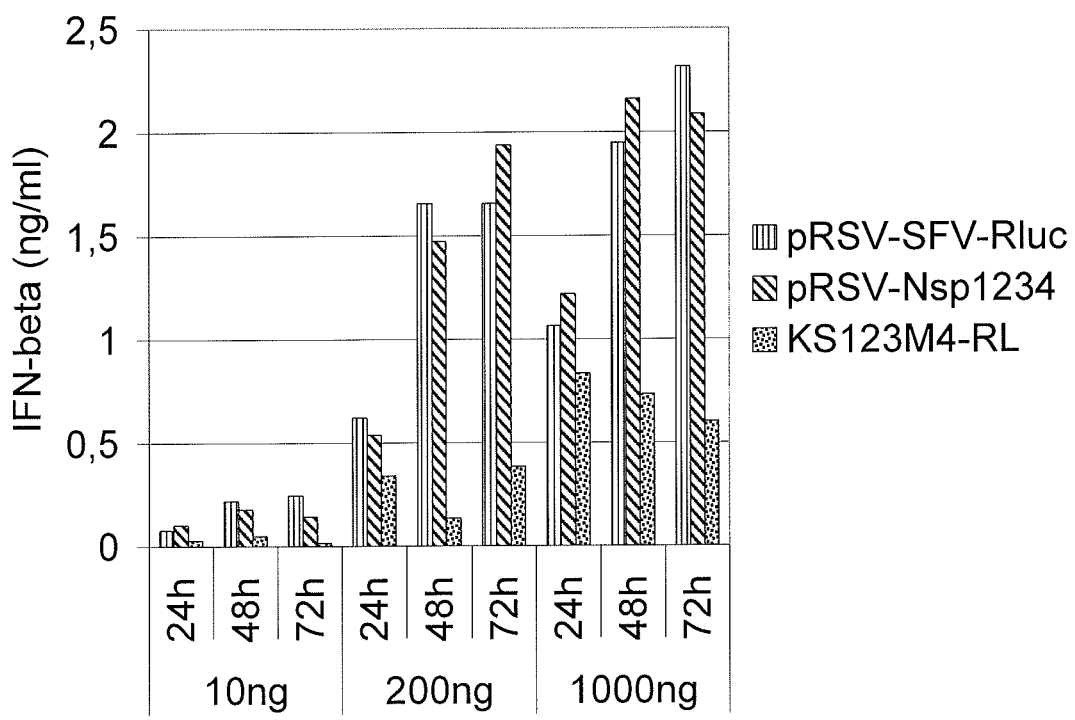
Figure 4:
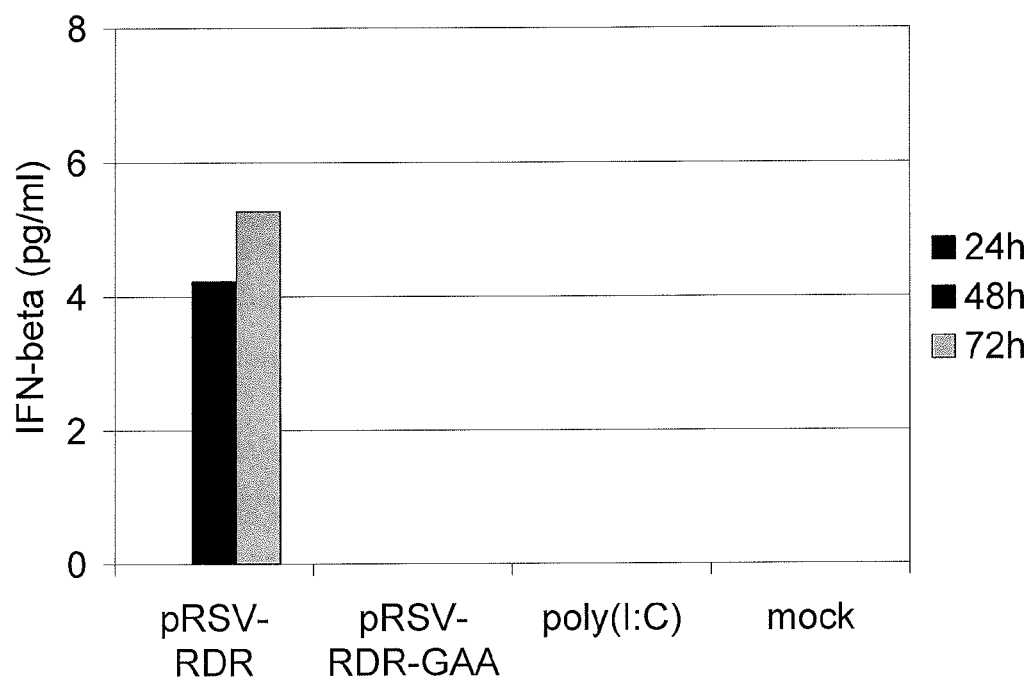

Ahlquist et al., "Host Factors in Positive-Strand RNA Virus Genome Replication" Journal of Virology, (2003), vol. 77, No. 15, pp. 8181-8186.
Akira et al., "Pathogen Recognition and Innate Immunity" Cell, (2006), vol. 124, No. 4, pp. 783-801.
Blazevic et al., "Induction of Human Immunodeficiency Virus Type-1-Specific Immunity with a Novel Gene Transport Unit (GTU)-MultiHIV DNA Vaccine" Aids Research and Human Retroviruses, (2006), vol. 22, No. 7, pp. 667-677.
Breakwell et al., "Semliki Forest Virus Nonstructural Protein 2 Is Involved in Suppression of the Type I Interferon Response" Journal of Virology, (2007), vol. 81, No. 16, pp. 8677-8684.
Edwards et al., "Signalling Pathways Mediating Type I Interferon Gene Expression" Microbes and Infection, (2007), vol. 9, No. 11, pp. 1245-1251.
Fraser et al., "Improving Vaccines by Incorporating Immunological Coadjuvants" Expert Rev. Vaccines, (2007), vol. 6, No. 4, pp. 559-578.
Germain, "An Innately Interesting Decade of Research in Immunology" Nature Medicine, (2004), vol. 10. No. 12, pp. 1307-1320.
Kanzler et al., "Therapeutic Targeting of Innate Immunity with Toll-Like Receptor Agonists and Antagonists" Nature Medicine, (2007), vol. 13, No. 5, pp. 552-559.
Le Bon et al., "Links Between Innate and Adaptive Immunity Via Type I Interferon" Current Opinion in Immunology, (2002), vol. 14, No. 4, pp. 432-436.
Medzhitov, "Recognition of Microorganisms and Activation of the Immune Response" Nature, (2007), vol. 449, pp. 819-826.
Miller et al., "Modification of Intracellular Membrane Structures for Virus Replication" Nature Reviews Microbiology, (2008), vol. 6, No. 5, pp. 363-374.
Moradpour et al., "Replication of Hepatitis C Virus" Nature Reviews Microbiology, (2007), vol. 5, No. 6, pp. 453-463.
Querec et al., "Understanding the Role of Innate Immunity in the Mechanism of Action of the Live Attenuated Yellow Fever Vaccine 17D" Advances in Experimental Medicine and Biology, (2007), vol. 590, pp. 43-53.
Rautsi et al., "Type I Interferon Response Against Viral and Non-Viral Gene Transfer in Human Tumor and Primary Cell Lines" The Journal of Gene Medicine, (2007), vol. 9, No. 2, pp. 122-135.
Riedmann et al., "Bacterial Ghosts as Adjuvant Particles" Expert Review of Vaccines, (2007), vol. 6, No. 2, pp. 241-253.
Rikkonen et al., "Nuclear and Nucleolar Targeting Signals of Semliki Forest Virus Nonstructural Protein nsP2" Virology, (1992), vol. 189, Issue 2, pp. 462-473.
Sioud, "Innate Sensing of Self and Non-Self RNAs by Toll-Like Receptors" Trends in Molecular Medicine, (2006), vol. 12, No. 4, pp. 167-176.
Theofilopoulos et al., "Type I Interferons ($\alpha/\beta$) in Immunity and Autoimmunity" Annual Review of Immunology, (2005), vol. 23, pp. 307-336.
Tomar et al., "Catalytic Core of Alphavirus Nonstructural Protein nsP4 Possesses Terminal Adenylyltransferase Activity" Journal of Virology, (2006), vol. 80, No. 20, pp. 9962-9969.
Ventoso et al., "Translational Resistance of Late Alphavirus mRNA to eIF2$\alpha$ Phosphorylation: A Strategy to Overcome the Antiviral Effect of Protein Kinase PKR" Genes & Development, (2006), vol. 20, pp. 87-100.
Vercammen et al., "Sensing of Viral Infection and Activation of Innate Immunity by Toll-Like Receptor 3" Clinical Microbiology Reviews, (2008), vol. 21, No. 1, pp. 13-25.
Wolfgang Leitner et al., *Alphavirus-based DNA vaccine breaks immunological tolerance by activating innate antiviral pathways*, 9(1) Nature Medicine 33-39 (Jan. 2003).
Tarbatt et al., *Sequence analysis of the avirulent, demyelinating A7 strain of Semliki Forest virus*, 78(7) J. Gen. Virol. 1551-1557 (1997).
Tarbatt et al., Swiss-Prot Accession No. Q809B7, Oct. 31, 2006.

\* cited by examiner

Fig. 1

EXPRESSION VECTOR ENCODING ALPHAVIRUS REPLICASE AND THE USE THEREOF AS IMMUNOLOGICAL ADJUVANT

This application is a U.S. National Phase Patent Application pursuant to 35U.S.C. §371 of International Patent Application No. PCT/EP2009/056240, filed on May 22, 2009, and published as WO 2009/141434 on Nov. 26, 2009, which claims priority to U.S. Provisional Patent Application Serial No. 61/071,898, filed on May 23, 2008, now expired, the contents of which are incorporated herein by reference in their entireties for all purposes.

TECHNICAL FIELD

The present invention relates to the field of immunological tools and in particular to the field of vaccines and to adjuvants suitable for use in vaccine compositions.

BACKGROUND OF THE INVENTION

The mammalian immune system has evolved in order to survive in the environment containing a large variety of microorganisms, which colonize them in a number of niches like skin, intestine, upper and lower respiratory tract, urogenital tract etc. Some of the niches like colon and skin are colonized constitutively by an endogenous microbiota, whereas other niches (internal organs and lower respiratory tract) are normally kept sterile in an immunocompetent host. The effects of microorganism can be positive for the host, as is the case for the many intestinal symbiotic bacteria. In other cases, microbial colonization can be detrimental to the host. Such negative effects depend on the status of the host's immune system—certain pathogens (known as opportunistic pathogens) affect only immunocompromised individuals. The potential detrimental effect of microbial infections has led to the evolution of variety of host-defence mechanisms. In jawed vertebrates, there are two types of defence: innate and adaptive immune responses. The main distinction between these is the receptor types used to recognize pathogens, the time-delay needed to launch the response and the presence/absence of memory. The two types of defence do not operate completely independently from each other. As seen in the below, innate immune system sends specific signals to the adaptive immune system, helping to mount the response that is most efficient to the specific pathogen; and vice versa—adaptive immune response also activates some modules of the innate immune system.

Innate Immune Response

Innate immunity is always present in healthy individuals and its main function is to block the entry of microbes and viruses as well as to provide a rapid elimination of pathogens that do succeed in entering the host tissues. It provides immediate protection for the multicellular organism.

Innate immune system is not a single entity. It is a collection of distinct modules or subsystems that appeared at different stages of evolution:

Mucosal epithelia producing antimicrobial peptides, protecting the host from pathogen invasion;
phagocytes with their anti-microbial mechanisms against intra- and extracellular bacteria;
acute-phase proteins and complement system that are operating in the circulation and body fluids;
natural killer cells, which are involved in killing virus infected cells;
eosinophils, basophils and mast cells, which are involved against protection of multicellular parasites;
type I interferons and proteins induced by them, which have a crucial role in defence against viruses.

The innate immune response is responsible for the early detection and destruction of invading microbes, and relies on a set of limited germ line-encoded pattern-recognition receptors (PRRs) for detection. To initiate immune responses, PRRs recognize pathogen-associated molecular patterns (PAMPs) and induce several extracellular activation cascades such as the complement pathway and various intracellular signalling pathways, which lead to the inflammatory responses.

The innate immune system utilizes PRRs present in three different compartments: body fluids, cell membranes, and cytoplasm. The PRRs in the body fluids play major roles in PAMP opsonization, the activation of complement pathways, and in some cases the transfer of PAMPs to other PRRs. PRRs located on the cell membrane have diverse functions, such as the presentation of PAMPs to other PRRs, the promotion of microbial uptake by phagocytosis, and the initiation of major signalling pathways.

There are several functionally distinct classes of PRRs. The best characterized class is Toll-like receptors (TLRs). These are transmembrane receptors that recognize viral nucleic acids and several bacterial products, including lipopolysaccharide and lipoteichoic acids and are the primary signal-generating PRRs (Akira, S 2006). In addition, cytoplasmic PRRs which can be grouped into three classes: interferon (IFN)-inducible proteins, caspase-recruiting domain (CARD) helicases, and nucleotide-binding oligomerization domain (NOD)-like receptors (NLRs). Among the best studied IFN-induced antiviral proteins are the family of myxovirus resistance proteins (Mx), protein kinase R (PKR), oligoadenylate synthetase (2'-5' OAS). These antiviral proteins and CARD helicases such as RIG-I and Mda5 are involved in antiviral defence. In contrast, NLRs are mainly involved in antibacterial immune responses.

Toll-Like Receptors (TLRs)

TLRs are the best-characterized signal-generating receptors among PRRs. They initiate key inflammatory responses and also shape adaptive immunity. All TLRs (TLR1-11) known in mammals are type I integral membrane glycoproteins containing an extracellular leucine-rich repeat (LRR) domain responsible for ligand recognition and a cytoplasmic Toll-interleukine-1 receptor homology (TIR) domain required for initiating signalling. TLRs recognize quite diverse microbial components in bacteria, fungi, parasites, and viruses including nucleic acids. Although normally present at the plasma membrane to detect extracellular PAMPs, a few TLRs, including TLR3, TLR7, TLR8, and TLR9, recognize their ligands in the intracellular compartments such as endosomes. The latter TLRs share the ability of nucleic acid recognition, detecting dsRNA (TLR3), ssRNA (TLR7 in mice, TLR8 in humans), and non-methylated CpG DNA motifs (TLR9).

TLRs initiate shared and distinct signalling pathways by recruiting different combinations of four TIR domain-containing adaptor molecules: MyD88, TIRAP, Trif, and TRAM. With the exception of TLR3, all the other TLRs recruit the myeloid differentiation factor 88 (MyD88), which is associated with members of the IL-receptor-associated kinase (IRAK) family (Mouldy Sioud 2006). These signalling pathways activate the transcription factors nuclear factor kappa B (NF-κB) and activator protein-1 (AP-1), which is common to all TLRs, leading to the production of inflammatory cytokines and chemokines. They also activate interferon regulatory factor-3 (IRF3) and/or IRF7 in TLRs 3, 4, 7, 8, and 9 which is a prerequisite for the production of type I interferons such as IFN-α and IFN-β (For review Edwards et al 2007, Vercammen et al 2008, Medzitov R 2007).

In addition to direct activation of innate host-defence mechanisms, some PRRs are coupled to the induction of adaptive immune responses. T-and B-cells, the two main classes of cells in the adaptive immune system, express antigen binding receptors with random specificities and therefore recognize antigens that lack any intrinsic characteristics indicative of their origin. Therefore, T-and B-lymphocytes require instructions indicating the origin of the antigen they recognize. These instructions come from the innate immune system in the form of specialized signals inducible by PRRs. For T-cells this association is interpreted by dendritic cells. Type I interferons are involved in the activation and migration of dendritic cells (described in more details under Antiviral response). When activated dendritic cell migrates to the lymph node, they present the pathogen-derived antigens, together with PRR-induced signals, to T-cells. This results in T-cell activation and differentiation of T-helper (Th) cells into one of several types of effector Th-cells (Th1, Th2 and Th-17 cells). For instance TLR-engagement induces IL-12 production by dendritic cells, which directs Th cells to differentiate into Th1 cells. The type of effector response is thus dictated by the innate immune system. In addition, type I interferons also regulate the function of cytotoxic T-cells and NK cells, either directly or indirectly by inducing IL-15 production.

The innate immune system also receives positive feedback signals from the adaptive immune system. For instance, effector Th-cells produce appropriate cytokines that activate specific modules of the innate immune system: macrophages are activated by cytokines (interferon-γ) secreted from Th1 cells, neutrophils are activated by Th-17 cells (interleukin-17) cells, mast cells and basophils are activated by Th2 cells (interleukin-4 and -5). Likewise, bound antibodies (IgG) activate complement proteins and help phagocytosis by opsonizing pathogens.

Adaptive Immune Response

The adaptive immune system uses a broad range of molecules for its activities. Some of these molecules are also used by the innate immune system, e.g. complement proteins, others, including antigen-specific B-cell and T-cell receptors, are unique to the adaptive immune system. The most important properties of the adaptive immune system, distinguishing it from innate immunity, are a fine specificity of B- and T-cell receptors, and a more slow development of the response and memory of prior exposure to antigen. The latter property forms the basis of vaccination—priming of the immune system by attenuated pathogen, by selected components of the pathogen or by mimicking infection in other ways (e.g. by DNA-vaccine encoding selected antigens from a pathogen) results in the development of immunological memory, which triggers response more quickly and more efficiently upon pathogen encounter.

There are two types of adaptive immunity, humoral immunity and cell-mediated immunity. Humoral immunity is mediated by B-cells. Activated B-cells start to secrete the receptors into circulation and mucosal fluids, which in this case are referred to as antibodies (immunoglobulins). The genes encoding these receptors are assembled from variable and constant fragments in the process of somatic recombination, prior to pathogen encounter, which yields a diverse repertoire of receptors. Each B- or T-cell is able to synthesize immunoglobulins or T-cell receptors of a single specificity that bind to a specific molecular structure (epitope). Antibodies bind noncovalently to specific antigens to immobilize them, render them harmless or tag the antigen for destruction (e.g. by complement proteins or by macrophages) and removal by other components of the immune system. Cell mediated immunity is mediated by T-cells. T-cells are key players in most adaptive immune responses. They participate directly in eliminating infected cells (CD8+ cytotoxic T-cells) or orchestrate and regulate activity of other cells by producing various cytokines (CD4+ T-helper cells). Also the induction of antibodies by B-cells is in a majority of cases dependent on T-helper cells. The distinguished feature of T-cell antigen receptors is their inability to recognize soluble molecules—they can recognize peptide fragments of protein antigens on the cell surface bound to specialized peptide display molecules, called major histocompatibility complex (MHC). T-helper cells need MHC class II molecules for recognizing antigenic peptide fragments, and cytotoxic T-cells need MHC class I molecules. This feature enables T-cells to detect intracellular pathogens, which otherwise could remain undetected by the immune system, because short peptides (9-10 amino acids) from all proteins synthesized in eukaryotic cells (including peptides derived from pathogens) are exposed on the cell surface in the, peptide pockets' of MHC molecules. Adaptive immune response is initiated after pathogen capture by professional antigen presenting cells (APCs). Naive T-lymphocytes need to see antigens presented by MHC-antigens on APCs. These cells are present in all epithelia of the body, which is the interface between the body and external environment. In addition to that, APCs are present in smaller numbers in most other organs. APCs in the epithelia belong to the lineage of dendritic cells. In the skin, the epidermal dendritic cells are called Langerhans cells. Dendritic cells capture antigens of microbes that enter the epithelium, by the process of phagocytosis or pinocytosis. After antigen capture dendritic cells round up and lose their adhesiveness for the epithelium, they leave the epithelium and migrate via lymphatic vessels to the lymph node draining that epithelium. During the process of migration the dendritic cells mature into cells capable of stimulating T-cells. This maturation is reflected in increased synthesis and stable expression of MHC molecules, which display antigen to T-cells, and other molecules, co-stimulators, that are required for full T-cell responses. The result of this sequence of events is that the protein antigens of microbes are transported to the specific regions of lymph nodes where the antigens are most likely to encounter T-lymphocytes. Naive T-lymphocytes continuously recirculate through lymph nodes, and it is estimated that every naive T-cell in the body may cycle through some lymph nodes at least once a day. Thus, initial encounter of T-cells with antigens happens in lymph nodes and this is called priming. Primed CD4+ T-helper cells start secreting a variety of cytokines, which help other cells of the immune system to respond. Dendritic cells carry to the lymph nodes not only peptide fragments from pathogens, but also PRR-induced signals sent from innate immune system (as mentioned above, type I IFNs influence activation and differentiation of dendritic cells). Dendritic cells convert this information into activation of specific clones of T-cells (that recognize pathogenic peptides) and differentiation of suitable type of T-helper cells. Priming of CD8+ T-cells is also performed by dendritic cells, but further proliferation and maturation of CD8+ T-cells into fully functional killer cells depends on cytokines secreted by T-helper cells.

Taken together, between the innate and adaptive immune system there is a continuous and complicated interplay.

Success in developing vaccines against "difficult" pathogens where no vaccines are currently available (HIV-1, TB and malaria) might depend on exploiting completely new methods for eliciting a protective immune response.

Antiviral Response to Positive-Strand RNA Viruses and their Replication By-Products Positive-Strand RNA Viruses Positive-strand RNA viruses encompass over one-third of all virus genera. Positive-strand RNA virus genomes are templates for both translation and replication, leading to interactions between host translation factors and RNA replication at multiple levels. All known positive-strand RNA viruses carry genes for an RNA-dependent RNA polymerase (RdRp) used in genome replication. However, unlike other RNA viruses, positive-strand RNA viruses do not encapsidate this polymerase. Thus, upon infection of a new cell, viral RNA replication cannot begin until the genomic RNA is translated to produce polymerase and, for most positive-strand RNA viruses, additional replication factors. All characterized positive-strand RNA viruses assemble their RNA replication complexes on intracellular membranes. In and beyond the alphavirus-like superfamily the replication of viral RNA occurs in association with spherical invaginations of intracellular membranes. For example, alphaviruses use endosomal and lysosomal membranes for their replication complex assembly. The membrane provides a surface on which replication factors are localized and concentrated. This organization also helps to protect any dsRNA replication intermediates from dsRNA-induced host defence responses such as RNA interference or interferon-induced responses (Ahlquist P et al 2003).

Despite differences in genome organization, virion morphology and host range, positive-strand RNA viruses have fundamentally similar strategies for genome replication. By definition, the viral (+)RNA genome has the same polarity as cellular mRNA and the viral genomic RNA is directly translated by the cellular translation machinery. Firstly, non-structural proteins are synthesized as precursor polyproteins and cleaved into mature non-structural proteins by viral proteases. A large part of the viral genome is devoted to non-structural proteins, which are not part of the virion and carry out important functions during viral replication. Following translation and polyprotein processing, a complex is assembled that includes the RdRp, further accessory non-structural proteins, viral RNA and host cell factors. These so-called replication complexes (RCs) carry out viral-RNA synthesis. Negative-sense viral RNA is synthesized early in infection and after the formation of replication complexes this negative-strand RNA is used as a template to synthesize full-length positive-sense genomic RNA as well as the subgenomic RNA. The key enzyme responsible for these steps is the RNA-dependent RNA-polymerase, which act within replicase complex (Moradpour et al 2007, Miller and Krijnse-Locker 2008).

Viral RNA Sensing

Positive strand RNA viruses produce in the process of replication negative strand RNA, positive strand RNA, double strand RNA (dsRNA) and subgenomic mRNA, which are themselves powerful inducers of innate immune response pathways. The effect is induced through TLR3 (dsRNA), TLR7/8 (ssRNA), and some other TLRs which recognize the specific structural elements in the secondary structure of the ssRNA. For example, positive strand RNA virus, yellow fever virus live attenuated vaccine is definitely one of the most effective vaccines available that activates innate immunity via multiple Toll-like receptors which also induces differential effects on the quality of the long-lasting antigen-specific T cell response (Querec TD and Pulendran B Adv Exp Med. Biol. 2007; 590:43-53).

As stated above, cells possess receptors and signalling pathways to induce antiviral gene expression in response to cytosolic viral presence. Multiple cytokines are induced by virus infection including interleukine-6 (IL-6), IL-12 p40, and tumor necrosis factor (TNF), but the hallmark of antiviral responses is the production of type I interferons. Type I interferons include multiple subtypes encoded by separate intronless genes: one IFN-β and 13-14 IFN-α subtypes, depending on species. Type I interferons can be produced by all nucleated cells, including epithelial cells, fibroblasts at mucosal surfaces, and dendritic cells, in response to virus infection. In addition all cells can respond to type I interferons through the type I interferon receptor (IFNAR), which binds all subtypes.

Genes encoding the cytosolic PRRs and the components of the downstream signalling pathways are themselves interferon inducible, leading to a positive-feedback loop that can greatly amplify innate antiviral responses. It has been thought that this loop is set in motion by the presence of dsRNA in cells. dsRNA fulfills the criteria for being a marker of virus infection, as long dsRNA molecules are absent from uninfected cells but can be formed by the complementary annealing of two strands of RNA produced during the replication of RNA viruses. dsRNA is known to activate nuclear factor kappa B (NF-κB) and interferon regulatory factors-3 (IRF-3) and -7, that are essential in the synthesis of type I IFNs. Interferons mediate their antiviral response via specific cell surface receptors, IFNAR, that activate cytoplasmic signal transducers and activators of transcription (STATs), which translocate into the nucleus and activate numerous IFN-stimulated genes (ISGs) (Rautsi et al 2007).

Retinoic acid-inducible gene I (RIG-I) and melanoma differentiation-associated gene 5 (MDA5) are cytoplasmic IFN-inducible DExD/H box RNA-helicases that can detect intracellular viral products, such as genomic RNA, and signal for IRF3 and IRF7 activation and for the induction of IFN-α, -β, and -λ gene expression. RIG-I is a cytosolic protein containing RNA-binding helicase domain and two caspase activation and recruitment domains (CARDS). Like RIG-I, MDA5 bears a RNA-helicase domain and two CARDs. They both signal through interferon-β promoter stimulator-1 (IPS-1). Signal adaptor IPS-1 is located on mitochondria and contains an N-terminal CARD that forms homotypic interactions with CARDs of RIG-I and Mda5. This results in activation of the C-terminal catalytic domain and the initiation of a signalling cascade that culminates in the transcription of cytokine genes through activation of NF-κB and IRF3.

Although both RIG-I and Mda5 bind poly(I:C), a synthetic dsRNA, and signal via a common pathway, they selectively respond to different viruses. For example RIG-I detects influenza A virus, vesicular stomatitis virus (VSV), Japanese encephalitis virus (JEV), and Sendai virus (SeV), whereas MDA5 detects picornaviruses, such as encephalomyocarditis virus (EMCV), Theiler's encephalomyelitis virus, and mengovirus. Independently of single or double strandedness the critical element in RIG-I stimulation by RNA is the presence of 5'-triphosphates. Which also provides explanation for the virus specificity of RIG-I.

Type I interferons affect various subtypes of dendritic cells (DCs). They can act as an autocrine survival factors for certain natural interferon producing cells, promote the differentiation of peripheral blood monocytes to DCs and induce their phenotypic and functional maturation. As most cell types are capable of expressing type I interferons, maturation of DCs in non-lymphoid tissues may be triggered following infection of neighbouring cells. These DCs will acquire the ability to migrate to lymphoid organs and initiate T cell responses (LeBon and Tough 2002).

Type I interferon signalling also upregulates IFN-γ production by DCs and T cells and thereby favours the induction and maintenance of Th1 cells. Additionally, acting directly or indirectly, they can influence the expression and function of a variety of cytokines. For example enhance interleukin-6 (IL-6) signalling, and production of anti-inflammatory transforming growth factor β (TGF-β), IL-1 receptor antagonist and soluble tumor necrosis factor (TNF) receptors. Type I interferons or their inducers can also elicit high IL-15 expression by DCs, thereby causing strong and selective stimulation of memory-phenotype CD8+ T cells (Theofilopoulos et al 2005).

Specific viral pathogen infection related patterns (like accumulation of the dsRNA in cytoplasm of the virus infected cells), recognition factors responding to these patterns (e.g. Toll-like receptors), and different anti-viral defence pathways triggered by these interactions have been described above. The complex system called innate immunity is directed to lead the cascade of events from recognition of pathogen to destroying the virus infected cells and rapid clearing of the virus infection from the body. In addition, the activation of the innate immune system is an important determinant of the quantity and quality of the adaptive immune response evoked against the viral antigens (Germain RN 2004).

Immunological Adjuvants.

Immunological adjuvants were originally described by Ramon in 1924 as substances used in combination with a specific antigen that produced a more robust immune response than the antigen alone. This very broad definition includes a wide variety of materials. The immunological adjuvants available today fall broadly into two categories: delivery systems and immune potentiators (for review Fraser C. K., Diener K. R., Brown M. P. and Hayball J. D. (2007) Expert Reviews in Vaccines 6(4)559-578).

Delivery systems can change the presentation of the antigen within the vaccine thus maximizing antigen exposure to the immune system, targeting antigen in a certain form to specific physiological locations thereby assuring pick-up of the antigen by the professional Antigen Presenting Cells (APCs). Examples of immunological adjuvants presented as delivery system type adjuvants in the formulations of vaccines are alum, emulsions, saponins and cationic lipids.

Immune activators act directly on immune cells by activating the pathways significant for induction of adaptive immunity. These may be exogenous microbial or viral components, their synthetic derivatives or endogenous immunoactive compounds such as cytokines, chemokines and costimulatory molecules. This type of molecules can enhance specific immunity to the target antigen. As of today, toll-like receptor agonists, nucleotide oligomerization domain-like receptor agonists, recombinant endogenous compounds like cytokines, chemokines or costimulatory molecules are available and may serve as immune potentiators. It is however important to emphasize that cytokines and chemokines are species-specific molecules and therefore are not readily comparable in different animals. In these cases the homologues of respective molecules need to be used, which considerably complicates the use of such adjuvants as well as the interpretation of experimental results in one species and the extrapolation thereof to another species.

DNA vaccines as several other genetic vaccines have been developed over several years and present a promising approach in the induction of specific immune responses in test animals. However, these vaccines have turned out to be ineffective in humans and larger animals. One of the reasons is probably that the reactivity and immunogenicity is lower than for traditional vaccines. A likely reason for this deficiency is the limited capacity for protein expression in vivo, which is of greater significance in outbred animals, including humans as well as the more homogeneous nature and lack of contaminating pathogen-derived ingredients in the actual vaccine preparation.

This has caused a need for the development of specific, finely tuned immunological adjuvants for the preparation of vaccines, which would be targeted for activation of the immune system without profound toxic effects. As a result of this need, efforts have been made to combine DNA vaccines with cytokines or chemokines, like hematopoietic growth factors, such as GM-CSF, or chemokines like MIP-1α, which can improve the immune responses against the antigen encoded by the DNA vaccine. However, unfortunately these effects are still quite weak. Co-delivery of the cytokines and chemokines as proteins requires enormous work before a good quality protein can be produced for actual use in animals or humans.

As for the use of nucleic acid based expression vectors for the expression of an adjuvant for use in combination with DNA vaccines, questions arise regarding the appropriate level and site of expression of a particular adjuvant molecule and the effect of this expression on the tissue to which the vaccine is administered.

The observations about the potential useful effect of adjuvants in immune stimulation were made in the early days by Gaston Ramon who found that higher antibody titers were developed in the horses which developed abscesses post-vaccination. The concept of using immunological adjuvants to improve antigen-specific immune responses has been inseparably linked from the early findings with their capacity to induce inflammatory processes due to contaminations. As a result, the use of such immunological adjuvants may cause clinically unacceptable toxicity and serious health concerns. Therefore, the only globally licensed adjuvant for human use is alum, a weak adjuvant capable only of inducing humoral immunity. All the other stronger adjuvants capable of inducing both humoral and cell-mediated immunity available today are confined to experimental use only.

It has been shown that the current repertoire of vaccine adjuvants is inadequate to generate effective vaccines against significant pathogens including HIV1, malaria and tuberculosis (Riedmann et al. 2007; Fraser et al. 20007). Combination of known adjuvants may overcome some of the problems associated with the vaccines that are available, however, a reliable, safe and advanced new generation of immune modulators in the form of adjuvants is certainly needed.

In view of the problems still present in the prior art explained in the above, the aim of the present invention was thus to find a more efficient adjuvant to accompany and improve the responses to vaccines available today. The adjuvant according to the present invention, is a modulator of the immune system, meaning that it will improve and strengthen the immune response in a subject to whom the vaccine is administered.

SUMMARY OF THE INVENTION

The above problems associated with the adjuvants available in the art today are solved by the present invention by providing a novel medical use of an alphaviral replicase or of an expression vector encoding an alphaviral replicase as an immune system modulating adjuvant which is species-independent, more efficient and easier to administer than the immune system modulating adjuvants available today.

The present invention is based upon the surprising discovery that the provision of an alphaviral replicase alone, comprising RNA dependent RNA polymerase (RdRp) activity and compartmentalized to the correct compartment in the cell, is able to induce innate immune responses in a cell. This is possible without the presence of viral genome or any other non-structural or structural viral proteins.

Accordingly, this is a breakthrough discovery which allows for the development of efficient adjuvants which are able to activate the immune response providing a quantitatively and qualitatively more efficient response to a vaccine antigen than when a vaccine is administered on its own.

Hence, in one aspect, the present invention encompasses an alphaviral replicase comprising an RNA dependent RNA polymerase (RdRp) for use as an adjuvant for modulating the immune response. Also, the present invention of course relates to the use of an alphaviral replicase, said replicase comprising an RNA dependent RNA polymerase, in the manufacture of an adjuvant for modulating the immune response. In a preferred embodiment, said replicase is encoded by an expression vector, such as a DNA vector for use as an adjuvant for modulating the immune system. In one preferred embodiment, said replicase is an SFV (Semliki Forest Virus) replicase.

The efficacy of the immune system modulating activity of the alphaviral replicase can be adjusted through specific mutations in the nuclear localization region of the nSP2 subunit of the replicase. Accordingly, the present invention relates to alphaviral replicases having specific mutations in the nSP2 region of the wildtype replicase, for use as adjuvants for modulating the immune system and to expression vectors encoding alphaviral replicases having specific mutations in the nSP2 region of the wildtype replicase for use as adjuvants for modulating the immune system, which mutants have been shown to be even more efficient in inducing an immune response in a subject when administered together with a vaccine of choice. The specific mutations shown to be efficient in the current context are RDR and AAA mutants presented in positions 1185-1187 of the wildtype SFV replicase amino acid sequence, which are further described herein.

The alphaviral replicase has been shown to be exceptionally suitable as an adjuvant by being able to boost and increase the immune response in a subject to whom a vaccine, e.g. in the form of a nucleic acid based vaccine, is administered. The inventors show that the interferon response is increased in vivo when the adjuvant in the form of a replicase is administered together with a vaccine, as compared to when only the vaccine is administered.

Furthermore, the invention relates to the use of the alphaviral replicase or an expression vector encoding an alphaviral replicase as an adjuvant for modulating the immune response. The present invention also relates to use of an alphaviral replicase as disclosed herein as an adjuvant in a vaccine composition for the manufacture of a medicament for the prevention and/or treatment of an infectious disease. Said vaccine accompanying the adjuvant may e.g. be in the form of a nucleic acid based vaccine or a protein-based vaccine. In addition, a method for preparing a vaccine composition comprising the adjuvant according to the invention is provided herein. The present invention also relates to a novel protein with replicase activity as well as an expression vector encoding said replicase.

BRIEF DESCRIPTION OF THE DRAWINGS

Figure 1:
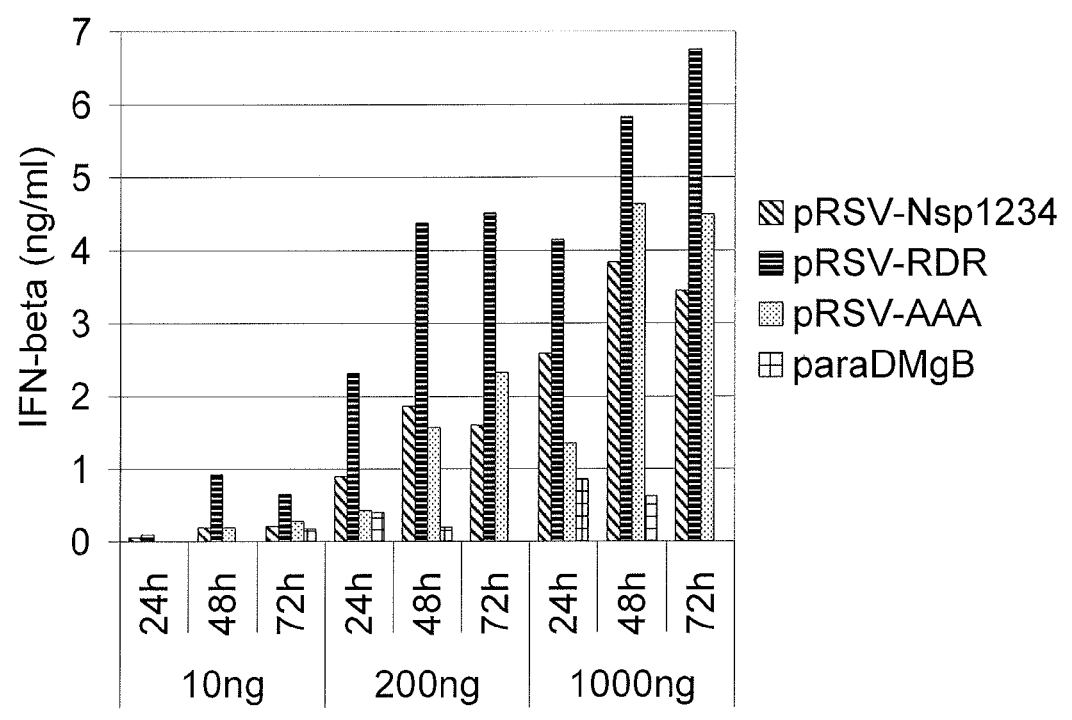

FIG. 1. IFN-beta measured from Cop5 cell culture supernatants transfected with RdRp using different DNA concentrations. 10 ng, 200 ng, or 1000 ng of expression vectors pRSV-Nsp1234, pRSV-RDR, pRSV-AAA, or HIV multiantigen expressing vector paraDMgB (negative control, no RdRp activity) were transfected into Cop5 cells. Cell culture supernatants were collected in three time-points (24 h, 48 h, and 72 h) and assayed for interferon-β expression.

FIG. 2. IFN-beta measured from Cop5 cell culture supernatants transfected with RdRp using different DNA concentrations. 10 ng, 200 ng, or 1000 ng of pRSV-RDR, pRSV-GAA, pRSV-RDR-GAA, and pRSV-AAA-GAA were transfected into Cop5 cells. Cell culture supernatants were collected in three time-points (24 h, 48 h, and 72 h) and assayed for interferon-β expression.

FIG. 3. IFN-beta measured from Cop5 cell culture supernatants transfected with either transreplicase or RdRp constructs. 10 ng, 200 ng, or 1000 ng of pRSV-SFV-Rluc, pRSV-Nsp1234, and KS123M4-RL (negative control, no RdRp activity) were transfected into Cop5 cells. Cell culture supernatants were collected in three time-points (24 h, 48 h, and 72 h) and assayed for interferon-β expression.

FIG. 4. IFN-beta in HEK293 cells. HEK293 cells were transfected with electroporation and with the addition of carrier DNA. 1 μg of plasmid DNA or poly(I:C) was used. Supernatants were collected at three time-points (24 h, 48 h, and 72 h) and assayed for interferon-β expression.

FIG. 5. IFN-a and -b in HACAT cells. Cells were transfected by electroporation and with the addition of carrier DNA. 1 μg of plasmid DNA or poly(I:C) was used. Supernatants were collected at three time-points (24 h, 48 h, and 72 h) and assayed for interferon-β and -α expression. Lanes 1, 5, 9 pRSV-RDR; lanes 2, 6, 10 pRSV-RDR-GAA; lanes 3, 7, 11 poly(I:C); lanes 4, 8, 12 mock transfected.

FIG. 6. IFN-gamma ELISPOT of mice. Augmentation of cellular immune response in mice when plasmid DNA is co-administrated with the plasmid pRSV-RDR at ratio 4:1 (800 ng vaccine vector and 200 ng adjuvant vector). Group 1 GTU-MultiHIV; group 2 GTU-MultiHIV+pRSV-Nsp1234; group 3 GTU-MultiHIV+pRSV-RDR; group 4 control group.

FIG. 7. Augmentation of the humoral immune response against the antigens from influenza virus when the plasmid vector encoding influenza virus HA and NA is co-administrated with the DNA plasmid pRSV-RDR.

FIG. 8. Cumulative IFN-gamma ELISPOT results against two recognized epitopes in Gag and Env, group average. Three groups of Balb/C mice were immunized two times (week 0 and week 4) with plasmid DNA encoding MultiHIV antigen alone or together with pRSV-RDR that was added either with the first or the second immunization. Fourth group was naïve. Interferon gamma Elispot was done from freshly isolated spleen cells 10 days after the second immunization. Group 1 GTU-MultiHIV; group 2 GTU-MultiHIV+pRSV-RDR with 2nd immunization; group 3 GTU-MultiHIV+pRSV-RDR with 1st immunization; group 4 naive mice.

FIG. 9: Cumulative Granzyme B ELISPOT results against two recognized epitopes in Gag and Env, group average. Three groups of Balb/C mice were immunized two times (week 0 and week 4) with plasmid DNA encoding MultiHIV antigen alone or together with pRSV-RDR that was added either with the first or the second immunization. Fourth group was naïve. Granzyme B Elispot was done from freshly isolated spleen cells 10 days after the second immunization. Group 1 GTU-MultiHIV; group 2 GTU-MultiHIV+pRSV-RDR with 2nd immunization; group 3 GTU-MultiHIV+ pRSV-RDR with 1st immunization; group 4 naive mice.

DEFINITIONS

An "expression vector" refers to a DNA or RNA based vector or plasmid which carries genetic information in the form of a nucleic acid sequence. The terms "plasmid", "vector" and/or "expression vector" may be used interchangeably herein.

An "RNA dependent RNA polymerase" or an "RdRp", is an enzyme, protein or peptide having an enzymatic activity that catalyzes the de novo synthesis of RNA from an RNA template. A replicase is a viral polyprotein or complex of polyprotein processing products that has RdRp activity and catalyzes the replication of specific viral RNA. They are commonly encoded by viruses which have a RNA genome. Accordingly, a replicase provides the function of an RNA dependent RNA polymerase, but also further comprises additional viral non-structural polyprotein sub-units providing other functions in addition to RdRp activity. A "compartmentalized" RdRp (CRdRp) is defined herein as an RdRp of a replicase that is capable of providing the RdRp activity and which is able to be directed to the correct compartment in the cell to provide its function.

The terms "antigen" and "gene of interest" as referred to herein, comprises entities, which when administered to a subject in need thereof, for example in the form of an expression vector or in the form of a peptide or a protein, directly or indirectly may generate an immune response in the subject to whom it is administered. When the antigen is a gene which may provide for the expression of an antigenic protein/peptide it may also be referred to as a "gene of interest". If the gene of interest is administered in the form of an expression vector, such as a DNA vector, the immune response will be triggered when the genes encoded by the vector are expressed in the host.

A "vaccine" as referred to herein, is a preparation which is used to improve the immunity to a particular disease. A vaccine can comprise one or more antigen(s) derived from a pathogen which when administered to a subject in need thereof, will trigger an immune response to the one or more antigen(s), thereby inducing an immunity in the subject providing protection towards a later "real" infection with the pathogen in question. Vaccines can be prophylactic, e.g. prevent or lessen the effects of a future infection by any natural pathogen, or they can be therapeutically acting when the infection is already present. In the context of the present invention, the alphaviral replicase or the expression vector encoding the alphaviral replicase is intended to be used as an adjuvant for modulating the immune response together with both a preventive and/or a therapeutic vaccine. Vaccines may be dead or inactivated microorganisms or purified products derived from them. In general, there are four types of traditional vaccines. These are vaccines containing killed microorganisms which are previously virulent micro-organisms, live attenuated virus microorganisms, toxoids which are inactivated toxic compounds, or subunits of the attenuated or inactivated microorganism. A vaccine may be in the form of a protein, or it may be indirect in the form of an expression vector from which one or more antigen(s) are expressed thereby inducing an immune response in a subject. In a vaccine composition as disclosed herein, any vaccine, examples of which are provided in the above, may be administered together with the adjuvant according to the invention. Hence, in the present context, a "vaccine" refers to any entity which comprises one or more antigen(s) or which encodes one or more gene(s) of interest, and which when administered will generate an immune response as explained herein. A "vaccine" may also comprise additional components aiding in the administration to a subject in need thereof, such as a constituent and/or excipient, examples of which are given herein.

An "adjuvant" as referred to herein, may be defined as an immunological agent that can activate the innate immune system and modify the effect of other agents, such as a vaccine. An adjuvant is an agent that may stimulate the immune system and increase the response to a vaccine, providing a stronger and more efficient immune response to the subject who is vaccinated, than when the vaccine is administered on its own. Hence, adjuvants are often used to increase or in any other manner influence the effect of a vaccine by e.g. stimulating the immune system to respond to the vaccine more vigorously, thus providing increased immunity to a particular disease. Adjuvants may accomplish this task by mimicking specific sets of evolutionarily conserved molecules. Examples of such molecules are liposomes, lipopolysaccharide (LPS), bacterial cell wall components, double-stranded RNA (dsRNA), single-stranded DNA (ssDNA), and unmethylated CpG dinucleotide-containing DNA etc. The presence of an adjuvant in conjunction with the vaccine can greatly increase the innate immune response to the antigen by mimicking a natural infection. When an "adjuvant" is referred to herein, what is intended is an alphaviral replicase or an expression vector encoding an alphaviral replicase with RNA dependent RNA polymerase activity as disclosed herein, providing the adjuvant function. The adjuvant may also be an expression vector, such as a DNA vector, providing for the expression of an alphaviral replicase comprising the RNA dependent RNA polymerase activity. Hence, the alphaviral replicase may be administered as it is, or it may be administered in the form of an expression vector, from which the alphaviral replicase is expressed providing the adjuvant function. A vaccine composition as referred to herein, may in some embodiments comprise more than one vaccine entity, such as in the form of one or more expression vector(s), encoding the one or more genes of interest, or providing the one or more antigen(s) by being e.g. a protein-based vaccine, thereby providing a cocktail of vaccines to be administered to the patient in need thereof.

By "modulating the immune system", "modulating the immune response", or an "immune system modulating activity" is meant the actions or activities which are provided by the adjuvant, as defined herein, and which effects are further explained with the term adjuvant in the above. This may for example be in the form of stimulating the immune system to respond to the vaccine more vigorously and/or providing increased immunity to a particular disease. The adjuvant according to the invention is characterized by that it when it is administered together with a vaccine will provide an increased response to the antigen being administered in the form of a vaccine, than when the vaccine is administered on its own without the adjuvant.

An "expression cassette" as disclosed herein, comprises a nucleic acid sequence encoding one or more genes or coding sequences optionally accompanied by various regulatory sequences for regulating the expression of the genes. These genes may form part of a vaccine encoding various antigens which when expressed will generate an immune response in the host.

A "mutation" as referred to herein, constitutes a deletion, substitution, insertion and/or specific point mutation that has been performed in a nucleic acid sequence to change the performance of the adjuvant function according to the invention. Specific mutations introduced into the replicase for improving the adjuvant properties thereof according to the present invention are further exemplified herein.

A "promoter", is a regulatory region located upstream towards the 3' region of the anti-sense strand of a gene, providing a control point for regulated gene transcription. The promoter contains specific DNA sequences, also named response elements that are recognized by transcription factors which bind to the promoter sequences recruiting RNA polymerase, the enzyme that synthesizes the RNA from the coding region of the gene.

In the present context, when a nucleic acid sequence or an amino acid sequence "essentially corresponds to" a certain nucleic acid or amino acid sequence, this refers to a sequence which has from 90% identity with the mentioned sequence, such as about 91, 92, 93, 94, 95, 96, 97, 99 or close to 100% identity with the present sequence. Of course, in some embodiments the nucleic acid or amino acid sequence also consists of the specified sequence.

DETAILED DESCRIPTION OF THE INVENTION

The present inventors disclose for the first time that an alphaviral replicase, carrying functional RNA dependent RNA polymerase (RdRp) activity, is able to cause an immune system modulating effect, i.e. to act as an immune system modulating adjuvant, when administered alone without the need for any additional structural or non-structural viral proteins or genomic nucleic acid sequences to provide this effect.

Herein it is shown for the first time that an alphaviral replicase comprising a functional RdRp administered alone to the cells is able to induce induction of type I interferons, which activate the innate immunity and improve the quality and effectiveness of the adaptive humoral and cellular immune responses. It is envisaged that the alphaviral replicase with the functional RdRp can principally be used as immune system modulating adjuvant in combination with any type of vaccine or antigen.

Furthermore, it is shown that the function of the alphaviral replicase as an immune system modulating adjuvant could be further improved by introducing specific mutations in a region of the replicase defined as the nuclear localization signal of the nSP2 subunit (Rikkonen et al. 1992).

It is important to note that no specific viral template RNA containing cis-signals for interaction with the RdRp of the replicase is needed for its activity as an immune system modulating adjuvant, which means that, without wishing to be bound by theory, the RdRp may use some cellular RNA as a template to initiate synthesis of the RNA replication intermediates in the cell cytoplasm. This is a breakthrough which provides for a novel approach for constructing an adjuvant, only rendering it necessary to administer an alphaviral replicase, e.g. in the form of a protein or encoded by an expression vector, such as a DNA vector, without any other parts of the virus, to obtain an activation of the immune response.

Accordingly, in a first aspect the present invention relates to an alphaviral replicase comprising an RNA dependent RNA polymerase, for use as an adjuvant for modulating the immune system. It should be understood that herein, whenever referred to an alphaviral replicase comprising an RNA dependent RNA polymerase for use as an adjuvant for modulating the immune system herein, whichever the embodiment, it also refers to use of an alphaviral replicase comprising an RNA dependent RNA polymerase for the manufacture of an adjuvant for modulating the immune response. Hence, accordingly, the present invention also in a similar aspect relates to the use of an alphaviral replicase comprising RNA dependent RNA polymerase, such as in the form of an expression vector, for the manufacture of an adjuvant for modulating the immune response.

In one preferred aspect of the invention, the alphavirus is the Semliki Forest Virus. It should be understood that herein, whenever a replicase is referred to, it always comprises the option of the replicase being a SFV replicase. In one embodiment, the amino acid sequence of the replicase of the Semliki Forest Virus essentially corresponds to SEQ ID NO:1, being suitable for use as an adjuvant for modulating the immune system. The amino acid sequence of the replicase of the Semliki Forest Virus may also consist of the sequence corresponding to SEQ ID NO:1, or of the sequences corresponding to the mutant replicases. In one preferred embodiment, said replicase is mutated in the nsP2 region generating the mutant RRR>RDR in positions 1185-1187 of SEQ ID NO:1, being suitable for use as an adjuvant for modulating the immune system. This mutated sequence corresponds to the amino acid sequence provided in SEQ ID NO: 2, and is also encompassed by the present invention for use as an adjuvant for modulating the immune response. In another preferred embodiment, the replicase is mutated in the nsP2 region generating the mutant RRR>AAA in the positions 1185-1187 of SEQ ID NO:1, also being suitable for use as an adjuvant for modulating the immune system. This mutated sequence corresponds to the amino acid sequence as provided in SEQ ID NO:3 and is also encompassed by the present invention for use as an adjuvant for modulating the immune response. The invention of course also relates to an expression vector encoding a replicase as defined in any embodiment herein, for use as an adjuvant for modulating the immune response. Said replicase, either in the form of a peptide and/or a protein, and/or encoded by an expression vector, may be formulated together with a pharmaceutically acceptable excipient and/or constituent, examples of which are given herein. In yet another embodiment, a mixture of both or either of the mutated replicases as mentioned herein and/or together with the wildtype replicase, optionally expressed by one or more expression vector(s) is used as an adjuvant for modulating the immune response.

It is important to note that the present inventors have for the first time discovered that an alphaviral replicase, without the presence of any additional viral antigens, can in itself act as an immune system modulating adjuvant. For example, when in the form of an expression vector, the expression vector when expressed may cause an immune system modulating effect in a subject even in the absence of the simultaneous administration of additional nucleic acid sequences encoding a heterologous antigen or any other alphaviral nucleic acid sequences. To provide this effect, it has been shown that the RdRp activity of the replicase is crucial as well as the ability of the replicase to proceed to the correct compartment in the cell cytoplasm, i.e. the procedure of compartmentalization of the replicase, which is further discussed in the below.

Without wishing to be bound by theory, when the adjuvant is administered in the form of an expression vector, the replicase seems to be activated for expression in the cell nucleus of the transfected cells of the target tissue. It is further envisaged that upon transcription of the expression vector, the mRNA encoding the replicase is transported to the cytoplasm, where it is translated into the replicase protein that possesses cytoplasmic RNA-dependent RNA polymerase activity. This enzyme is compartmentalized to the specific cytoplasmic compartments, where the RNA-dependent RNA polymerase activity generates effector molecules, including, but possibly not limited to, double-stranded RNA, inside of the cell cytoplasm, which trigger a massive, strong and long-lasting cellular antiviral response, including the induction of expression of type I interferons. This type of induction of the antiviral response is universal, species-independent and activates both cell-mediated and humoral immune responses.

Accordingly, in another aspect, the present invention relates to an expression vector encoding an alphaviral replicase, such as SFV replicase, as defined herein, preferably a DNA vector, such as a plasmid DNA expression vector, which in one embodiment is pRSV-Nsp1234, corresponding essentially to the sequence as disclosed in SEQ ID NO:5, for use as an adjuvant for modulating the immune system. The nucleic acid sequence of the replicase of the Semliki Forest Virus may also consist of the sequence corresponding to SEQ ID NO:5, or of the sequences corresponding to the mutant replicases. In some embodiments, the replicase encoded by the expression vector is mutated in the nsP2 region. As a general reference, the nsP2 region of an SFV replicase (SEQ ID NO:1) is located approximately in amino acid positions 538-1336 of SEQ ID NO:1. In one embodiment, the expression vector encodes a replicase which is mutated in the nsP2 region generating the mutant RRR>RDR in positions 1185-1187 of SEQ ID NO:1, being suitable for use as an adjuvant for modulating the immune system. In one embodiment, said expression vector is encoded by the sequence essentially corresponding to SEQ ID NO:4, but wherein a mutation has been introduced into positions 4129-4131 of this sequence, such as in one embodiment the mutation CGG to GAC, for use as an adjuvant for modulating the immune response. The nucleic acid sequence of the replicase of the Semliki Forest Virus may also consist of the sequence corresponding to SEQ ID NO:4, but wherein a mutation has been introduced into positions 4129-4131 of this sequence, such as in one embodiment the mutation CGG to GAC. In another embodiment, the expression vector encodes a replicase which is mutated in the nsP2 region generating the mutant RRR>AAA in the positions 1185-1187 of SEQ ID NO:1, which is used as an adjuvant for modulating the immune system. In one embodiment, the expression vector is encoded by the sequence essentially corresponding to SEQ ID NO:4, but wherein a mutation has been introduced in positions 4126-4133 of this sequence, such as in one embodiment the mutation CGGCGGAG to GCCGCCGC, for use as an adjuvant for modulating the immune response. The nucleic acid sequence of the replicase of the SFV may also consist of the sequence corresponding to SEQ ID NO:4, but wherein a mutation has been introduced in positions 4126-4133 of this sequence, such as in one embodiment the mutation CGGCGGAG to GCCGCCGC. This means that in the respective amino acid sequences, the wild type amino acid sequence has been altered from RRR to RDR and AAA, respectively, in positions 1185-1187 in SEQ ID NO:1. Said expression vector, mutated or not, may in a preferred embodiment be a DNA vector. Said vector may also be a viral expression vector, such as an adenoviral vector or a herpesvirus-based vector or any other usable viral expression vector. In one embodiment, the expression vector is a RNA-based vector. In yet another embodiment, the adjuvant is administered in the form of alphaviral replicase mRNA. In one embodiment, the invention relates to an alphaviral replicase plasmid DNA expression vector which is pRSV-AAA, essentially corresponding to the nucleic acid sequence disclosed in SEQ ID NO:5, wherein positions 5126-5133 have been mutated from CGGCGGAG to GCCGCCGC, for use as an adjuvant for modulating the immune system. In another embodiment, the invention relates to an alphaviral plasmid DNA expression vector which is pRSV-RDR, essentially corresponding to SEQ ID NO:5, wherein positions 5129-5131 have been mutated from CGG to GAC, for use as an adjuvant for modulating the immune system. The nucleic acid sequence of the replicase of the Semliki Forest Virus may also consist of the sequence corresponding to SEQ ID NO:5, or of the sequences corresponding to the mutant replicases mentioned in the above.

As is understood by the skilled person, an expression vector according to the invention encoding the replicase for use as an adjuvant for modulating the immune system may of course also comprise additional commonly used components aiding in the expression of the vector, such as various regulatory sequences in the form of promoters, enhancers, etc. The expression vector encoding a replicase as defined herein for use as an adjuvant for modulating the immune system may also comprise an origin of replication and/or a selection marker, such as an antibiotic selection marker or a selection system based upon the araD gene, as provided for in the applicants own application published as WO2005/026364. Such a selection system as disclosed in WO2005/026364 comprises a bacterial cell deficient of an araD gene into which a vector carrying an araD gene, preferably a bacterial araD gene, such as an araD gene from *E. coli*, a complementary sequence thereof, or a catalytically active fragment thereof has been added as a selection marker. The araD gene encodes a functional L-ribulose-5-phosphate 4-epimerase (EC 5.1. 3.4.).

As demonstrated in the experimental section, the expression of the mutated forms of the replicase, also acts as immune system modulating adjuvants. Moreover, the mutations can modulate the adjuvant activity of the replicase: the RDR mutant has enhanced ability of type I IFN induction compared to (wildtype) wt replicase expression (Example 2). The replicase with the RRR>AAA mutation acts as an immune system modulating adjuvant similarly to the wild-type replicase (Example 2). It is also demonstrated in the experimental section that transfection of the different human and mouse cells with replicase-based expression vectors alone induced activation of type I interferon production (Example 2)

The results described in the experimental section clearly demonstrate that the RNA-dependent RNA polymerase (RdRp) activity of the replicase is absolutely necessary for immune modulation activity. The signature GDD motif of viral RNA polymerases is located in the region of nsp4 of the alphaviral replicase wherein the RdRp enzymatic activity is located. The mutation GDD>GAA in this motif destroys the RdRp activity (Tomar et al. 2006). Introduction of the GDD>GAA mutation into the replicase completely abolishes the induction of the Type I interferon response (Example 2), thereby demonstrating the necessity of the RdRp activity for the immune system modulating effect.

Experimental data also showed that the expression of replicases with a functional RdRp activity but not the replicases with the GDD>GAA mutation resulted in the accumulation of the dsRNA in the cytoplasm of the transfected cells. Without wishing to be bound by theory, these results indicate that the immune system modulating activity of the replicase may at least partially be mediated by the dsRNA recognition pathway, wherein the replicase produces dsRNA from endogenous RNA in the cytoplasm. However, it is not excluded that other pathways (e.g. via recognition of uncapped RNA) are involved. In some cases, induction of the type I IFN response was observed without indication of dsRNA accumulation in cytoplasm (Example 3).

In addition, different kinetic patterns were observed when the IFN response was induced by the SFV replicase expression compared to induction by synthetic dsRNA (poly I:C) transfection. In the experiments with the replicase expression vector transfections, the IFN level was increased during the first days after transfection. In contrast, the IFN level showed the maximum value in the first time point (24 h) after transfection with synthetic dsRNA, and decreased thereafter (Example 2).

Figure 6:
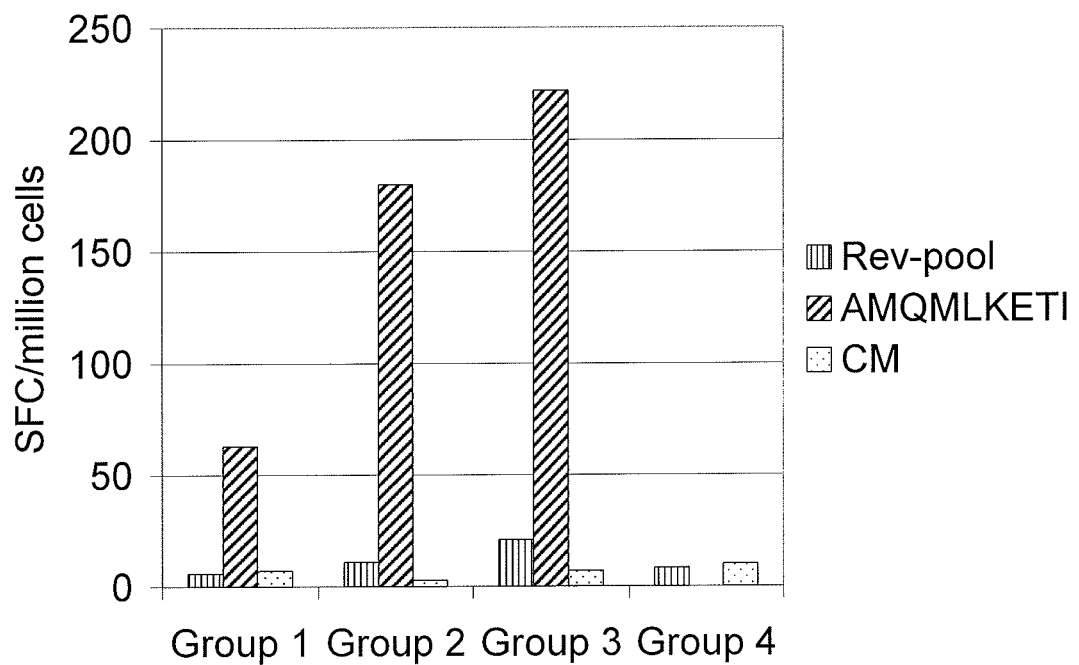

Immunological data presented in the experimental section clearly demonstrate that co-administration of the MultiHIV antigen DNA vaccine (Blazevic et al. 2006) together with the expression vector encoding the replicase, in this case the SFV replicase, significantly enhance quantitatively the cell-mediated immune response if compared with immunization with the DNA vaccine alone (measured by the ELISPOT assays) (FIG. 6). In addition, the values were clearly higher in the case with the replicase with the RRR>RDR mutation than the wildtype replicase (Example 4). Thus, the immunological data correlates with the results of IFN response induction: no positive effect to cell mediated immunity was observed if the replicase with destroyed RdRp activity (GDD>GAA) mutation was co-administered with the DNA vaccine. This clearly shows the importance of the RdRp activity for providing the adjuvant effect according to the invention.

The triggering of innate immunity responses, like type I IFN response by SFV infection, is well known in the art. It has also been shown that the immune modulation activity of the alphaviruses can be tuned by introducing mutations in the nsP2 region of the non-structural polypeptide of the replicase. The infection of primary mouse fibroblasts with SFV (Semliki Forest Virus) that had single point mutation RRR>RDR in nsP2 NLS, resulted in increased expression of type I IFN and the proinflammatory cytokine TNF-α in virus infected cells, if compared to wt SFV infection (Breakwell et al. 2007). It should however be pointed out that in Breakwell et al. the cells were infected with whole virus particles resulting in delivery, expression and replication of the whole viral genome, and, thereby generating the IFN response.

However, differently from prior art, the present invention have demonstrated that the induction of IFN response is not bound to viral infection and viral genome replication itself, but also can be obtained by the expression of the viral non-structural polyprotein, i.e. the replicase, alone without including the viral genome, viral particles or structural proteins. Moreover, it is demonstrated that the SFV replicase can be expressed from codon-optimised cDNA that have low homology with natural nucleic acids of SFV and still provide the adjuvant effect. An example of such a codon-optimized sequence is provided in SEQ ID NO:4. When expressed, SEQ ID NO:4 provides for the amino acid sequence as disclosed in SEQ ID NO:1.

It is to be understood that nucleic acid and amino acid sequences as referred to herein forming part of the present invention also comprise nucleic acid and amino acid sequences with approximately 90% identity to these sequences, such as 90, 91, 92, 93, 94, 95, 96, 97, 98, or 99% identity with the sequences. This means that the sequences may be shorter or longer or have the same length as the sequences disclosed herein, but wherein some positions in the nucleic acid sequence or the amino acid sequence have been altered in a suitable manner. However, when a mutated alphaviral replicase is used, the mutated sequence will always be present and hence be excluded when determining the identity of a sequence with the specific sequence disclosed herein. The sequence used in the present invention may hence be altered in any suitable manner for the intended purpose, such as by the introduction, change and/or removal of a specific nucleic acid in the nucleic acid sequence, or an amino acid in the amino acid sequence. It is important to note that even if the sequence is altered, the RNA dependent RNA polymerase activity of the replicase expressed from the expression vector remains.

In some embodiments of the present invention, said adjuvant as defined herein, for use as an adjuvant for modulating the immune system, is formulated together with a pharmaceutically acceptable excipient and/or constituent. Such a pharmaceutically acceptable excipient and/or constituent may be chosen from any suitable source. Examples of pharmaceutical excipients are liquids, such as water or an oil, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to an animal. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. A composition with the adjuvant can, if desired, also contain minor amounts of wetting or emulsifying agents, or pH buffering agents. The present compositions can also take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule. Other examples of suitable pharmaceutical excipients are described in Remington's Pharmaceutical Sciences 1447-1676 (Alfonso R. Gennaro ed., 19th ed. 1995). In one embodiment, the adjuvant according to the invention is formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Oral compositions can include standard excipients such as mannitol, lactose, starch, magnesium stearate, sodium saccharin, cellulose, and magnesium carbonate. In one embodiment, the excipients are of pharmaceutical grade. In another preferred embodiment, the adjuvant can be formulated for intravenous administration. Typically, compositions for intravenous administration comprise sterile isotonic aqueous buffer. Where necessary, the compositions can also include a solubilizing agent.

Methods of administration of the expression vector according to the invention comprise, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration can be left to the discretion of the practitioner. In an especially preferred embodiment, the adjuvant according to the invention, optionally in combination with a suitable vaccine, is administered to a patient in need thereof by a Gen Gun methodology (Klein et al 1992), by injections combined with electroporation ("electroporation-mediated DNA drug delivery"; intradermal or intramuscular), by topical administration onto mucosal surfaces (e.g. in the form of intranasal spray). The genetic adjuvant can be also combined with specific delivery adjuvants, which facilitate uptake of plasmid DNA by cells (e.g. polyethylenimide and other similar).

Electorporation (EP) utilizes the in vivo application of electrical fields to enhance the intracellular delivery of agents of interest in a targeted region of tissue. The EP delivery technique is dependent on the propagation of threshold level electrical fields throughout the target tissue site after the agent of interest has been distributed within the interstitial space of said tissue. This spatial and temporal "co-localization" of electrical fields and therapeutic agent in the target tissue is a critical requirement for achieving efficacious DNA delivery.

Electroporation has been demonstrated to be effective on both prokaryotic and eukaryotic cells and is capable of introducing DNA, large macromolecules (e.g., antibodies), proteins, dyes, metabolic precursors (e.g., 32P-ATP), and nonpermeant drugs and metabolites into cells with high efficiency. (De Lise et al, Developmental Biology Protocols; Jan. 21, 2000).

Figure 8:
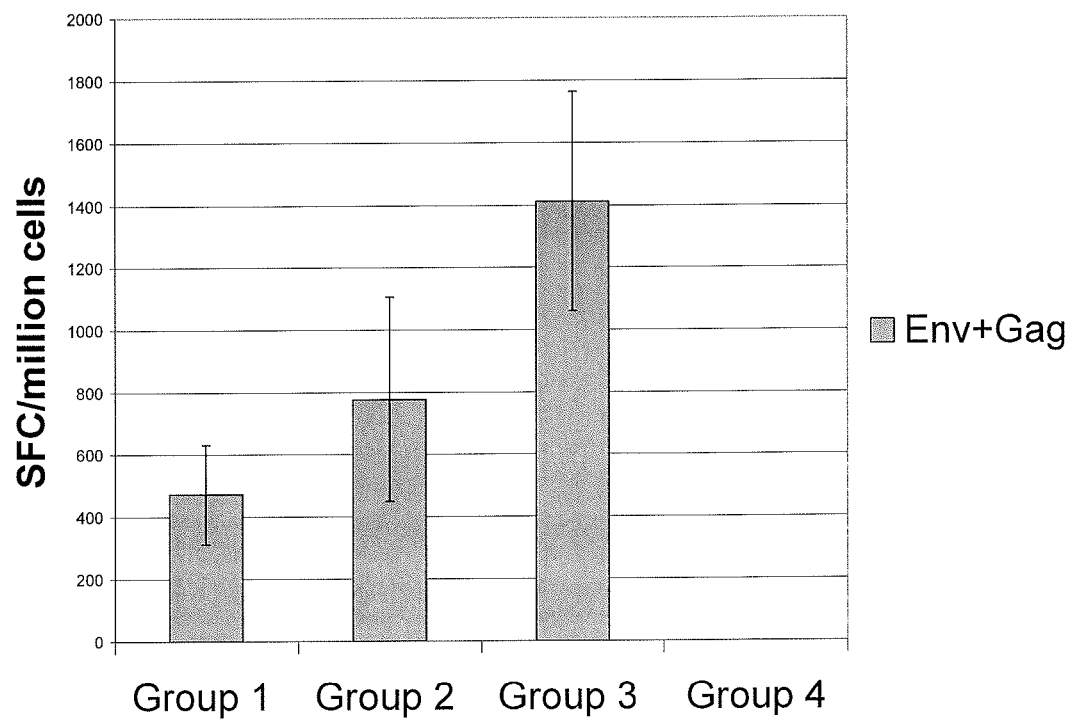
Figure 9:
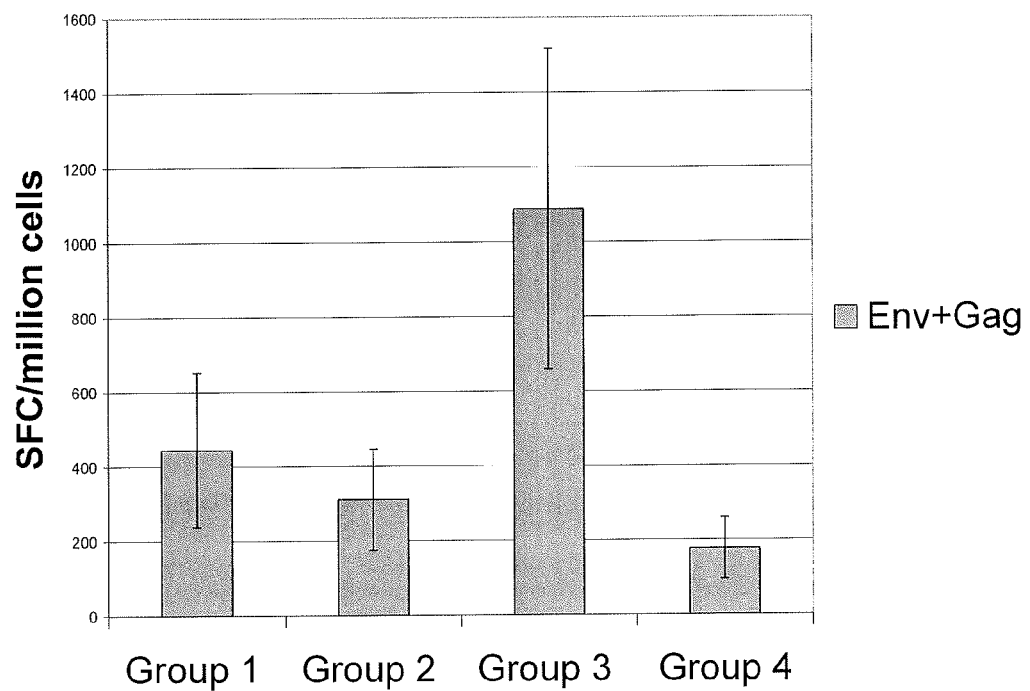

In one aspect of the present invention, the adjuvant may optionally be administered together with the vaccine of choice in a vaccine composition as a first immunization to the patient in need thereof. Some results provided by the present inventors have shown that such a mode of administration of the adjuvant may provide an improved immune response as compared to when the adjuvant is administered together with the vaccine in the second round of immunization (see FIGS. 8 and 9). Hence, in one aspect, the present invention relates to a method of administering a vaccine composition as defined herein, said vaccine composition comprising an adjuvant as defined herein, wherein said adjuvant is administered as part of the vaccine composition in the first immunization of the patient in need of said treatment. Optionally the co-administration of the adjuvant with the vaccine in a vaccine composition is only performed with the first immunization dose, i.e. no adjuvant is administered if additional doses of the vaccine are administered at a later stage to the individual in need thereof.

Hence, yet another aspect of the present invention relates to an alphaviral replicase, said replicase comprising an RNA dependent RNA polymerase, for use in a vaccine composition to be administered as a first immunization dose. Accordingly, in one aspect the present invention relates to a method of administering an adjuvant in a vaccine composition as defined herein, said adjuvant comprising an alphaviral replicase, said replicase comprising an RNA dependent RNA polymerase, wherein said administration of the adjuvant is performed with the first immunization dose of the vaccine composition to a patient in need thereof. In the present context, the "first immunization dose" refers to when the vaccine comprising one or more antigen(s) is administered to the patient in need thereof for the first time, thereafter triggering an immune response to the vaccine (i.e. the one or more antigen(s) administered therewith). In another aspect, the present invention relates to the use of an alphaviral replicase, said replicase comprising an RNA dependent RNA polymerase in the manufacture of a vaccine composition wherein said adjuvant is to be administered with the first immunization dose.

It should however be noted that the present invention is not limited to the mode of administration mentioned in the above, i.e. to be administered (optionally only) with the first immunization dose, and it may also well be so that the skilled practitioner will find additional alternative methods of administration which will function in a similar and equally preferred manner.

In another aspect, the invention relates to the use of an alphaviral replicase, or an expression vector encoding an alphaviral replicase, said replicase comprising an RNA dependent RNA polymerase, as an adjuvant for modulating the immune system. In one embodiment, said alpha virus is the Semliki Forest Virus. In yet another embodiment, said replicase used as an adjuvant for modulating the immune system corresponds to the amino acid sequence essentially as disclosed in SEQ ID NO:1. The amino acid sequence of the replicase of the Semliki Forest Virus may also consist of the sequence corresponding to SEQ ID NO:1, or of the sequences corresponding to the mutant replicases. In another preferred embodiment, the invention relates to the use of an alphaviral replicase, said replicase comprising an RNA dependent RNA polymerase, as an adjuvant for modulating the immune system, wherein the replicase is mutated in the nsP2 region generating the mutant RRR>RDR in positions 1185-1187 of SEQ ID NO:1, represented by SEQ ID NO:2. In another preferred embodiment, the replicase is mutated in the nsP2 region generating the mutant RRR>AAA in the positions 1185-1187 of SEQ ID NO:1, represented by SEQ ID NO:2. In some embodiments, the replicase as such defined is encoded by an expression vector, which in some embodiments is a DNA vector. Optionally, said replicase may be formulated together with a pharmaceutically acceptable excipient and/or constituent.

As demonstrated in example 5, the replicase with the mutation RRR>RDR also enhance the quantity of antibody response evoked by immunisation with DNA vaccine expressing the influenza antigens. The experimental data shows that the antibody levels were highest in the cases when the SFV replicase unit is co-administrated with influenza DNA vaccine, giving even higher values than well-defined adjuvant GM-CSF expression vector when co-administrated with the vaccine vector.

In yet another preferred aspect, the invention relates to the use of an alphaviral replicase, being either wildtype, codon-optimized or mutated, such as with an RDR or an AAA mutation as further defined herein, or an expression vector, such as a DNA vector, encoding an alphaviral replicase as defined herein, said replicase comprising an RNA dependent RNA polymerase, as an adjuvant for modulating the immune response when present in a vaccine composition, for the manufacture of a medicament for the prevention and/or treatment of an infectious disease. The present invention also relates to the use of an alphaviral replicase, as defined herein, as an adjuvant, in the manufacture of a vaccine composition. Said vaccine composition is preferably used for the prevention and/or treatment of an infectious disease. The present invention also relates to an alphaviral replicase, as defined herein being either wildtype, codon-optimized or mutated, such as with an RDR or an AAA mutation as further defined herein, or an expression vector encoding an alphaviral replicase, said replicase comprising an RNA dependent RNA polymerase, for use as an adjuvant for modulating the immune response when present in a vaccine composition, for the prevention and/or treatment of an infectious disease. As previously stated herein, the replicase may essentially correspond to the amino acid sequences as disclosed in SEQ ID NO:1, 2 or 3. Furthermore, the replicase may consist of the sequences as disclosed in SEQ ID NO:1, 2 or 3. In one embodiment, the vaccine composition, wherein the alphaviral replicase is present as an adjuvant, optionally encoded by an expression vector, is used for the prevention and/or treatment of an infectious disease. In one embodiment, the vaccine composition wherein the alphaviral replicase, optionally encoded by an expression vector, is present as an adjuvant is used for the prevention and/or treatment of a bacterial disease. In another embodiment, the vaccine composition wherein the alphaviral replicase, optionally encoded by an expression vector, is present as an adjuvant is used for the prevention and/or treatment of a viral disease, which viral disease preferably is caused by HIV (Human Immunodeficiency Virus; HIV-I, HIV-II), potentially leading to AIDS. In yet another embodiment, the vaccine composition wherein the alphaviral replicase is present, optionally encoded by an expression vector, as an adjuvant is used for the prevention and/or treatment of cancer. The vaccine which is administered in combination with the replicase providing the adjuvant properties of the composition may be any suitable vaccine for the present purpose. In some embodiments, the vaccine is protein-based, and in other embodiments the vaccine is an expression vector which encodes one or more antigen(s) or gene(s) of interest. The expression vector may be any suitable nucleic acid based expression vector encoding one or more genes of interest or antigens capable of inducing a specific immune response in a host to which the vaccine composition is administered. In one preferred embodiment, the vector of the vaccine composition is based upon an influenza virus.

Accordingly, in one aspect, the present invention relates to a vaccine composition comprising an alphaviral replicase as defined in any of the embodiments herein providing an adjuvant effect, and a vaccine of choice, also as defined herein. The vaccine may optionally be GTU-MultiHIV. (Blazevic V, et al. AIDS Res Hum Retroviruses. 2006 July; 22(7):667-77). Accordingly, the vaccine in the vaccine composition may in some aspects contain one or more structural or non-structural HIV protein(s) of choice, such as the antigens which are disclosed in the applicant's own publication WO02090558.

The replicase adjuvant and the antigen may in the context of the present invention be encoded by the same expression vector, wherein the replicase provides the adjuvant properties and the vaccine part of the vector is a separate independent part of the vector providing its function independently of the replicase. Despite thereof, the replicase may optionally be fused to any other coding sequence in any expression vector encoding an antigen. The expression vector encoding the adjuvant and/or the vaccine may in some embodiments be a DNA vector. As will be understood by the skilled person, the vaccine composition according to the invention may also comprise more than one vaccine unit, meaning that a cocktail of several vaccines may be administered to a subject in need thereof together with the adjuvant according to the invention.

In yet another aspect, the present invention relates to the use of an alphaviral replicase as defined herein in a vaccine composition as an adjuvant for modulating the immune response for the manufacture of a medicament for the prevention and/or treatment of an infectious disease or the use of an alphaviral replicase as defined herein as an adjuvant for the manufacture of a vaccine composition, wherein the vaccine comprising the one or more gene(s) of interest is an expression vector comprising:
  a. a DNA sequence encoding a nuclear-anchoring protein operatively linked to a heterologous promoter, said nuclear-anchoring protein comprising
    (i) a DNA binding domain which binds to a specific DNA sequence, and
    (ii) a functional domain that binds to a nuclear component, or a functional equivalent thereof; and
  b. a multimerized DNA binding sequence for the nuclear anchoring protein, wherein said vector lacks an origin of replication functional in mammalian cells.

Said vaccine composition as defined herein may be used in the treatment and/or prevention of an infectious disease, such as HIV infection, as well as in the treatment of a bacterial disease or cancer.

The present invention also relates to an alphaviral replicase as defined herein for use as an adjuvant for modulating the immune response in a vaccine composition for the prevention and/or treatment of an infectious disease, wherein the vaccine comprising the one or more gene(s) of interest is an expression vector comprising:
  a) a DNA sequence encoding a nuclear-anchoring protein operatively linked to a heterologous promoter, said nuclear-anchoring protein comprising
    (i) a DNA binding domain which binds to a specific DNA sequence, and
    (ii) a functional domain that binds to a nuclear component, or a functional equivalent thereof; and
  b) a multimerized DNA binding sequence for the nuclear anchoring protein, wherein said vector lacks an origin of replication functional in mammalian cells.

The term "nuclear-anchoring protein" refers to a protein, which binds to a specific DNA sequence and which is capable of providing a nuclear compartmentalization function to the vector, i.e., to a protein, which is capable of anchoring or attaching the vector to a specific nuclear compartment. In one embodiment, said nuclear-anchoring protein is the E2 protein from the Bovine Papilloma Virus Type 1. In another preferred embodiment, part i) and/or part ii), i.e. the DNA binding domain binding to a specific DNA sequence and/or the functional domain which binds to a nuclear component, is obtained from the E2 protein of the Bovine Papilloma Virus type 1. In one embodiment, said protein is a recombinant and/or a synthetic protein. A nuclear component may for example be mitotic chromatin, the nuclear matrix, nuclear domain 10 (ND10), or nuclear domain POD.

Such vectors which may form part of the vaccine compositions for use together with the replicase adjuvant according to the invention are further disclosed in applicants own application published as WO02090558, as well as in (Blazevic V, et al. AIDS Res Hum Retroviruses. 2006 July; 22(7):667-77). It should be noted that these vectors are however only examples of vectors that may be combined with the replicase for use as an adjuvant according to the present invention forming a vaccine composition as disclosed herein. Any suitable expression vector functioning as a vaccine may be formulated together with the replicase for use as an adjuvant therein according to the invention to produce a composition which will generate a stronger and more efficient immune response in the subject to which the vector is administered, than the administration of a vaccine alone. In one embodiment, the present invention relates to the use of an alphaviral replicase said replicase comprising an RNA dependent RNA polymerase for use as an adjuvant for modulating the immune system in a vaccine composition for the manufacture of a medicament for the prevention and/or treatment of an infectious disease.

Regarding vaccine compositions, wherein the replicase is used as an adjuvant, it should be noted that is it up to the skilled practitioner to determine the suitable dosage and the amounts of the adjuvant and/or the vaccine present in the vaccine composition for the subject in need of a treatment with the adjuvant as disclosed herein. In one preferred aspect, the replicase which is part of the vaccine composition is encoded by an expression vector, which preferably is a DNA vector. Said vaccine may also in some embodiments be an expression vector, such as a DNA vector, or it may be a protein-based vaccine.

In another aspect, the present invention relates to a method for preparing a vaccine composition as disclosed herein comprising therein an alphaviral replicase for use as an adjuvant, comprising mixing a suitable amount of the alphaviral replicase or an expression vector encoding an alphaviral replicase comprising a RNA dependent RNA polymerase with a suitable amount of the vaccine and optionally adding a pharmaceutically acceptable excipient and/or constituent. The suitable amounts of the respective ingredients may be determined by the skilled practitioner; however examples of some preferred doses are also given herein.

In yet another aspect, the present invention relates to a method comprising administering a suitable amount of a vaccine composition comprising therein an alphaviral replicase or an expression vector encoding an alphaviral replicase for use as an adjuvant according to the present invention to a subject in need thereof. The administration route for the vaccine composition may be any suitable route as determined by the skilled practitioner, examples of which are given herein. A subject in need thereof may be any mammal, such as a human being or an animal.

In yet another aspect, the invention relates to a method for administering an alphaviral replicase comprising RNA dependent RNA polymerase, optionally encoded by an expression vector, as an adjuvant for modulating the immune response to a subject in need thereof, said adjuvant being administered in combination with a vaccine in a suitable amount, when administered providing an increase in the immune response in the subject to whom the adjuvant and the vaccine is administered as compared to when the vaccine is administered on its own.

In yet another aspect, the invention relates to a protein essentially corresponding to the amino acid sequence disclosed in SEQ ID NO:3. The protein may also consist of the amino acid sequence as disclosed in SEQ ID NO:3. In yet another aspect, the invention relates to a protein essentially corresponding to SEQ ID NO:1, but wherein a mutation generating the change in amino acids from RRR to AAA has been performed in positions 1185-1187 of SEQ ID NO:1. The protein may also consist of the sequence corresponding to SEQ ID NO:1, but wherein a mutation generating the change in amino acids from RRR to AAA has been performed in positions 1185-1187 of SEQ ID NO:1. In yet another aspect, the invention relates to a protein essentially corresponding to the amino acid sequence as disclosed in SEQ ID NO:3, for use as a medicament. In yet another aspect, the invention relates to a protein consisting of the amino acid sequence as disclosed in SEQ ID NO:3, for use as a medicament. In yet another aspect, the present invention relates to a protein essentially corresponding to the amino acid sequence as disclosed in SEQ ID NO:3, for use as an adjuvant for modulating the immune response. In yet another aspect, the present invention relates to the use of a protein essentially corresponding to the amino acid sequence as disclosed in SEQ ID NO:3, for the manufacture of an adjuvant for modulating the immune response. In yet another aspect, the invention relates to a protein encoded by a nucleic acid sequence essentially corresponding to the sequence as disclosed in SEQ ID NO:4, but wherein a mutation has been introduced into positions 4126-4133 changing CGGCGGAG to GCCGCCGC. In yet another aspect, the invention relates to a protein encoded by a nucleic acid sequence consisting of the sequence as disclosed in SEQ ID NO:4, but wherein a mutation has been introduced into positions 4126-4133 changing CGGCGGAG to GCCGCCGC. In yet another aspect, the invention also relates to a nucleic acid sequence essentially corresponding to the sequence as disclosed in SEQ ID NO:4, but wherein a mutation has been introduced into positions 4126-4133 changing CGGCGGAG to GCCGCCGC. Furthermore, the invention also relates to a nucleic acid sequence consisting of the sequence as disclosed in SEQ ID NO:4, but wherein a mutation has been introduced into positions 4126-4133 changing CGGCGGAG to GCCGCCGC.

In yet another aspect, the invention relates to an expression vector comprising an expression cassette comprising a sequence essentially corresponding to the sequence as disclosed in SEQ ID NO:4, but wherein a mutation has been introduced into positions 4126-4133 of SEQ ID NO:4, generating when expressed the mutant RRR>AAA in positions 1185-1187 of SEQ ID NO:1 (SEQ ID NO:3). In yet another aspect, the invention relates to an expression vector comprising an expression cassette consisting of a sequence essentially corresponding to the sequence as disclosed in SEQ ID NO:4, but wherein a mutation has been introduced into positions 4126-4133 of SEQ ID NO:4, generating when expressed the mutant RRR>AAA in positions 1185-1187 of SEQ ID NO:1 (SEQ ID NO:3). In yet another aspect, the invention relates to an expression vector comprising an expression cassette comprising a sequence essentially corresponding to the sequence as disclosed in SEQ ID NO:4, wherein a mutation has been introduced into positions 4126-4133 of SEQ ID NO:4, generating when expressed the mutant RRR>AAA in positions 1185-1187 of SEQ ID NO:1, generating when mutated the amino acid sequence as disclosed in SEQ ID NO:3, for use as a medicament.

In yet another aspect, the present invention relates to the use of an alphaviral replicase, said replicase comprising an RNA dependent RNA polymerase, for the manufacture of an adjuvant for modulating the immune system. Said alpha virus may optionally be the Semliki Forest Virus. In some aspects, the amino acid sequence of the replicase essentially corresponds to SEQ ID NO:1. The amino acid sequence of the replicase may also consist of the sequence corresponding to SEQ ID NO:1, or of the mutated versions of the replicase mentioned herein. In other aspects, the replicase is mutated in the nsP2 region generating the mutant RRR>RDR in positions 1185-1187 of SEQ ID NO:1. In yet another aspect, the replicase is mutated in the nsP2 region generating the mutant RRR>AAA in the positions 1185-1187 of SEQ ID NO:1.

The present invention also relates to the use of an expression vector encoding an alphaviral replicase as defined herein, for the manufacture of an adjuvant for modulating the immune system. In some aspects, said expression vector is a DNA vector. Said replicase or said expression vector encoding said replicase may also be formulated together with a pharmaceutically acceptable excipient and/or constituent.

EXPERIMENTAL SECTION

Expression Vectors pRSV-Nsp1234 (SEQ ID NO:5) is a 10342 bp plasmid vector which expresses codon optimised SFV replicase (SEQ ID NO:4) from an RSV LTR promoter. Heterologous rabbit beta-globin gene derived intron is introduced into the replicase coding sequence.
Main Features:

| Start-End | Description |
| --- | --- |
| 9933-268 | pUCori |
| 437-963 | RSV LTR |
| 1001-8869 | SFV replicase coding sequence with intron (SEQ ID NO: 4) |
| 1213-1785 | intron |
| 8878-9090 | bgh pA |
| 9204-9899 | araD selection marker | pRSV-AAA is identical to pRSV-Nsp1234 (SEQ ID NO:5) but contains the RRR to AAA mutation in the aa 1185-1187 of SEQ ID NO:1: the nucleotide sequence in positions 5126-5133 is mutated from CGGCGGAG to GCCGCCGC.

pRSV-RDR is identical to pRSV-Nsp1234 (SEQ ID NO:5) but contains the RRR to RDR mutation in the aa 1185-1187 of SEQ ID NO:1: the nucleotide sequence in positions 5129-5131 is mutated from CGG to GAC.

pRSV-GAA is identical to pRSV-Nsp1234 (SEQ ID NO:5) but contains the GDD to GAA mutation in the aa 2283-2285 of SEQ ID NO:1: the nucleotide sequence in positions 8424-8427 is mutated from ACGA to CCGC.

pRSV-AAA-GAA is identical to pRSV-Nsp1234 (SEQ ID NO:5) but contains the RRR to AAA mutation in the aa 1185-1187 of SEQ ID NO:1: the nucleotide sequence in positions 5126-5133 is mutated CGGCGGAG to GCCGCCGC; and GDD to GAA mutation in the aa 2283-2285 of Nsp1234: the nucleotide sequence in positions 8424-8427 is mutated from ACGA to CCGC.

pRSV-RDR-GAA is identical to pRSV-Nsp1234 (SEQ ID NO:5) but contains the RRR to RDR mutation in the aa 1185-1187 of SEQ ID NO:1: the nucleotide sequence in positions 5129-5131 is mutated from CGG to GAC; and GDD to GAA mutation in the aa 2283-2285 of Nsp1234: the nucleotide sequence in positions 8424-8427 is mutated from ACGA to CCGC.

phelF4A1-Nsp1234 (SEQ ID NO:6) is a 10248 bp plasmid vector which expresses codon optimised SFV replicase (SEQ ID NO:4) from human elF4A1 promoter. Heterologous rabbit beta-globin gene derived intron is introduced into the replicase coding sequence.
Main Features:

| Start-End | Description |
| --- | --- |
| 9839-268 | pUCori |
| 367-894 | helF4A1 promoter |
| 907-8775 | SFV replicase coding sequence with intron (SEQ ID NO: 4) |
| 1119-1691 | intron |
| 8784-8996 | bgh pA |
| 9110-9805 | araD selection marker | phelF4A1-AAA is identical to phelF4A1-Nsp1234 (SEQ ID NO:6) but contains the RRR to AAA mutation in the aa 1185-1187 of SEQ ID NO:1: the nucleotide sequence in positions 5032-5039 is mutated from CGGCGGAG to GCCGCCGC.

phelF4A1-RDR is identical to phelF4A1-Nsp1234 (SEQ ID NO:6) but contains the RRR to RDR mutation in the aa 1185-1187 of SEQ ID NO:1: the nucleotide sequence in positions 5035-5037 is mutated from CGG to GAC.

phEF1aHTLV-Nsp1234 (SEQ ID NO:7) is 10258 bp plasmid vector expresses codon optimised SFV replicase (SEQ ID NO:4) from human EF1a promoter plus HTLV UTR. Heterologous rabbit beta-globin gene derived intron is introduced into the replicase coding sequence.
Main Features:

| Start-End | Description |
| --- | --- |
| 9849-268 | pUCori |
| 372-903 | hEF1a/HTLV |
| 917-8785 | SFV replicase coding sequence with intron (SEQ ID NO: 4) |
| 1129-1701 | intron |
| 8794-9006 | bgh pA |
| 9120 9815 | araD selection marker | phEF1aHTLV-AAA is identical to phEF1aHTLV-Nsp1234 (SEQ ID NO:7) but contains the RRR to AAA mutation in the aa 1185-1187 of SEQ ID NO:1: the nucleotide sequence in positions 5042-5049 is mutated from CGGCGGAG to GCCGCCGC.

phEF1aHTLV-RDR is identical to phEF1aHTLV-Nsp1234 (SEQ ID NO:7) but contains the RRR to RDR mutation in the aa 1185-1187 of SEQ ID NO:1: the nucleotide sequence in positions 5045-5047 is mutated from CGG to GAC.

phEF1aHTLV-GAA is identical to phEF1aHTLV-Nsp1234 (SEQ ID NO:7) but contains the GDD to GAA mutation in the aa 2283-2285 of SEQ ID NO:1: the nucleotide sequence in positions 8340-8343 is mutated from ACGA to CCGC.

EXAMPLE 1

Figure 5:
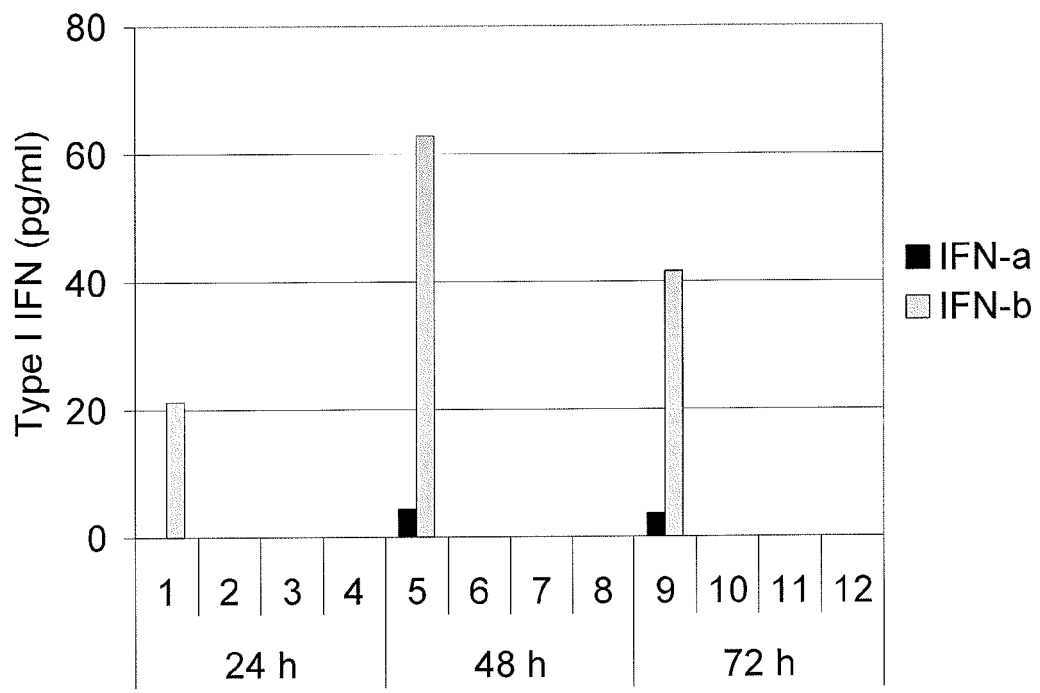

Construction of the DNA Plasmids Expressing the SFV Replicase with Mutation RRR>RDR in nsP2 Region Previously, the SFV replicase protein sequence (non-structural polypeptide nsP1234) (SEQ ID NO: 1) was back-translated and codon-optimised synthetic cDNA with heterologous rabbit beta-globin gene derived intron (introduced into the coding sequence) was synthesised (SEQ ID NO: 4). The cDNA was inserted into the expression plasmids so that different heterologous Pol II promoter and UTR elements were used for expression of SFV replicase from the codon-optimised coding sequence (FIG. 5). Particularly, Rous sarcoma virus 5'LTR, human elF4A1 promoter and chimeric promoter consisting of human EF1a promoter plus HTLV UTR were (SEQ ID NO:1) were named pRSV-Nsp1234 (SEQ ID NO 5), phelF4A1-Nsp1234 (SEQ ID NO 6), and phEF1aHTLV-Nsp1234 (SEQ ID NO 7). In addition, mutations in amino acids 1185-1187 RRR>AAA, in the nsP2 NLS region, were introduced into the vectors pRSV-Nsp1234, phelF4A1-Nsp1234, and phEF1aHTLV-Nsp1234. The plasmids were named pRSV-AAA, phelF4A1-AAA, and phEF1aHTLV-AAA, respectively.

It is known by literature data that a particular mutation in aa 1185-1187, RRR>RDR, of the gene encoding the wild-type SFV replicase significantly enhances the induction of IFN response in virus infected cells compared to cells infected with wt virus (Breakwell et al. 2007). Thus, mutation RRR>RDR was introduced into the vectors pRSV-Nsp1234, phelF4A1-Nsp1234, and phEF1aHTLV-Nsp1234. The plasmids were named pRSV-RDR, phelF4A1-RDR, and phEF1aHTLV-RDR, respectively.

It is known by literature data that the mutation GDD>GAA in the highly conserved GDD motif of the alphavirus nsP4 (aa 2283-2285 of the SFV Nsp1234) protein completely abolishes the RNA dependent RNA polymerase activity (Tomar et al. 2006). Previously, the GDD>GAA mutation was introduced into the replicase encoded by the vectors pRSV-Nsp1234, and pRSV-AAA. The cloned vectors were named as pRSV-GAA, and pRSV-AAA-GAA, respectively. In addition, the GDD>GAA mutation was introduced into the context of the plasmid pEF1aHTLV-Nsp1234, resulting in the vector pEF1aHTLV-GAA. With the intention to construct the control vector with the RRR>RDR mutation in the nsP2 region, the GDD>GAA mutation was introduced into the vector pRSV-RDR resulting in the plasmid pRSV-RDR-GAA.

EXAMPLE 2

Induction of Type I Interferon Response by RdRp Expression

We used Cop5 mouse fibroblast cell line (ATCC number CRL-1804) as a model cell line to discriminate between different replicase constructs for their ability to induce type I interferon expression. Cop-5 cells were propagated in Iscove's Modified Dulbecco's Medium (IMDM) supplemented with 10% fetal calf serum, 2 mM L-Glutamine, and streptomycin-penicillin. Two other human cell lines were also used comparatively—HEK293 and HACAT. Cells were propagated at 37° C. under 5% $CO_2$ and grown to 50 to 70% confluency.

Transfections

Electroporation was carried out with a Bio-Rad Gene Pulser. Three plasmid DNA concentrations were used for transfections with 10 ng, 200 ng and 1000 ng and equimolar amounts of control plasmids. All five different constructs were assayed for their ability to induce interferon response: pRSV-Nsp1234, pRSV-RDR, pRSV-AAA, pRSV-RDR-GAA, and pRSV-AAA-GAA. Cells were treated with trypsine, harvested by centrifugation and suspended in growth medium and supplemented with 5 mM NaBes. Electroporation was performed in 0.4 mm cuvettes in the presence of 50 ug of carrier DNA (salmon sperm DNA) and left in the cuvette for 15 minutes, washed with growth medium, and seeded on 6-well plates.

Interferon-β Assay

Cell culture supernatants were harvested 24 h, 48 h, and 72 h after transfection and frozen at −20° C. until further analysis using interferon-α and -β kits (PBL Biomedical Laboratories). Cell culture supernatants were appropriately diluted and used in the enzyme-linked immunosorbent assay according to manufacturer's instructions (PBL Biomedical Laboratories).

Results

Levels of interferon-β were quantified from collected supernatants by enzyme-linked immunosorbent assay (ELISA) (PBL Biomedical Laboratories) according to the manufacturer's instructions.

Conclusions

The generation of interferon response is due to the RNA-dependent RNA-polymerase (RdRp) activity in the compartmentalized RdRp complex. The RdRp effect was completely revoked when the enzymatic activity of RdRp was cancelled out by introducing a GAA mutation into the active centre of the polymerase unit (FIG. 2). The interferon expression profile measured from cell culture supernatants after transfection with constructs containing GAA mutation was similar to construct which does not encode any enzymatic activity (FIG. 1, lane paraDMgB).

On the basis of cell culture experiments, the mutant where the nuclear localization signal (NLS) has been modified in the Nsp2 region by introducing a RDR mutation was chosen as the most promising adjuvant candidate. The mutant with other modifications (AAA) in the same position of the NLS or wild type RdRp was also assayed for their ability to induce type I interferon response, but with substantially lower effects (FIG. 1). We also compared the replicase expression vector pRSV-Nsp1234 (SEQ ID NO:5) with the vector pRSV-SFV-Rluc that express both the replicase as well as specific viral cis-sequences containing template RNA. The latter acts as specific substrate for the replicase. The results of In IFN response induction assay showed that the existence of specific template RNA was not the crucial factor in inducing the interferon response (FIG. 3). In human cell lines HEK293 and HACAT we were also able to show specific interferon-β, and to a lesser extent, interferon-α induction by pRSV-RDR (FIGS. 4 and 5).

EXAMPLE 3

Accumulation of dsRNA in Cytoplasm of Replicase Expressing Cells

It is known that dsRNA intermediates are produced during the replication cycle of the SFV genome or the replicase template RNA. The presence of the dsRNA in the cytoplasmatic compartment signalling the viral infection to the cell and may lead of the antiviral response cascade, including the type I interferon response.

As is documented above (Example 2), the SFV replicase expression alone induce the type I interferon response in transfected cells. In addition, it was determined that RdRp activity of the replicase is critical for the IFN response, because no IFN response was observed after transfection with the expression vectors bearing GDD>GAA mutation that abolish the RdRp activity (Example 2).

Thus, the presence and localization of dsRNA in cells transfected with the replicase expression vectors alone was studied. For this purpose IF analysis using anti-dsRNA monoclonal antibody J2 (Scicons, Hungary) was utilised. This approach was previously used for detection of dsRNA in the cells after infection with +strand RNA viruses (Weber et al 2006). Briefly, the cells were transfected with replicase expression vectors and the next day after transfection the immunofluorescence analysis of paraformaldehyde fixed cells was performed with anti-Nsp1 and anti-dsRNA antibodies (mixed). For signal detection by fluorescence microscopy, secondary antibodies labelled with fluorochromes Alexa488 and Alexa568 and staining the nuclei by DAPI were used.

Experiment 1.

The RD cells were transfected by PEI-DNA complex with 0.5 ug of phEF1aHTLV-Nsp1234 or with 0.5 ug of phEF1 aHTLV-GAA. The results clearly demonstrated that the Nsp1 signal was observed in both cultures. The cytoplasmic dsRNA signal that co-localize with the anti-nsP1 stained spheric patterns was detected in the cells transfected with the phEF1aHTLV-Nsp1234 but not in cells transfected with phEF1 aHTLV-Nsp1234-GAA.

Experiment 2.

The Cop5 cells were transfected by electroporation with 1 ug of pRSV-Nsp1234, pRSV-GAA, pRSV-RDR or with pRSV-RDR-GAA. The results shown that although the Nsp1 signal was observed in all cultures, the replicase colocalized cytoplasmic dsRNA was detectable in cells transfected with pRSV-Nsp1234 or pRSV-RDR, but not in cells transfected with the plasmids pRSV-GAA or with pRSV-RDR-GAA.

Experiment 3.

The RD cells were transfected by PEI-DNA complex with 0.5 or 1 ug of pRSV-Nsp1234, pRSV-AAA or with pRSV-RDR. The results demonstrated that the Nsp1 signal was seen in all cultures. The cytoplasmic dsRNA signal that co-localize with the anti-nsP1 stained spheric patterns was detected in the cells transfected with the pRSV-Nsp1234 or pRSV-RDR but not in cells transfected with pRSV-AAA.

CONCLUSION

It was demonstrated that expression of the wt SFV replicase or the replicase with the mutation RRR>RDR in the nsP2 region, as previously defined herein, induce clear dsRNA accumulation in the cytoplasm of transfected cells that co-localize with the nsp1 positive spheric patterns. In contrast, no such dsRNA accumulation was detected if the cells which were transfected with replicase bearing the GDD>GAA mutation that abolish their RdRp activity.

Thus, these results show correlation between dsRNA accumulation and type I IFN induction by the different replicase mutants. However, no dsRNA accumulation was detected after transfection with the RRR>AAA mutant of the replicase, but induction of type I IFN response was still observed. This may indicate that the induced IFN response is not triggered only by dsRNA signalling, but also by other pathways related to the RdRp activity of the replicase. However, it cannot be excluded that smaller amounts of dsRNA is produced by the replicase mutant RRR>AAA that is not detectable by the used assay conditions.

EXAMPLE 4

Adjuvant Effect of the Expression of the SFV Replicase on the Cell Mediated Immune Response Three different groups of mice (Balb/c) 5 mice per group) were immunized with gene gun 2 times with 2 week intervals. One microgram plasmid DNA was administrated with both immunizations. The plasmid vector GTU-Multi-HIV (encoding selected genes from HIV-1) is an experimental DNA vaccine for HIV-1. When GTU-MultiHIV plasmid was co-administrated with the adjuvants pRSV-Nsp1234 or pRSV-RDR then 0.8 µg GTU-MultiHIV and 0.2 µg adjuvant plasmid were mixed together. For those mice receiving GTU-MultiHIV vector alone, 1 µg plasmid DNA was used. Mice were sacrificed 10 days later. Interferon γ ELISPOT analysis was performed with freshly isolated splenocytes. For stimulating cells one single peptide derived from p24 protein of HIV-1 (AMQMLKETI) was used, which is known to be presented by MHC class I molecules of Balb/c mice. Another stimulant was a pool of overlapping peptides covering the Rev-protein of HIV-1, another component encoded by the DNA-vaccine.

The results indicate that when a DNA vaccine was co-administrated with the vector encoding replicase from SFV, the augmentation of cellular immune response up to 3-fold was observed (FIG. 6).

EXAMPLE 5

Effect of the SFV Replicase Expression on the Induction of the Humoral Immune Response Against the Avian Influenza Virus Three different groups of mice (5 mice per group) were immunized with the plasmid vector pETB-12m-1, encoding HA- and NA-antigens from influenza virus. Mice were immunized in the similar way as in the previous example (1 µg plasmid DNA per immunization, when plasmid was co-administrated with the genetic adjuvant then the ratio 4:1 was used—800 ng immunizing vector and 200 ng adjuvant vector). Blood samples were analysed for the presence of specific antibodies in ELISA test 2 weeks after the $2^{nd}$ immunization. In this experiment another genetic adjuvant, the vector encoding cytokine GM-CSF, known to boost humoral immune response, was used for comparison.

Figure 7:
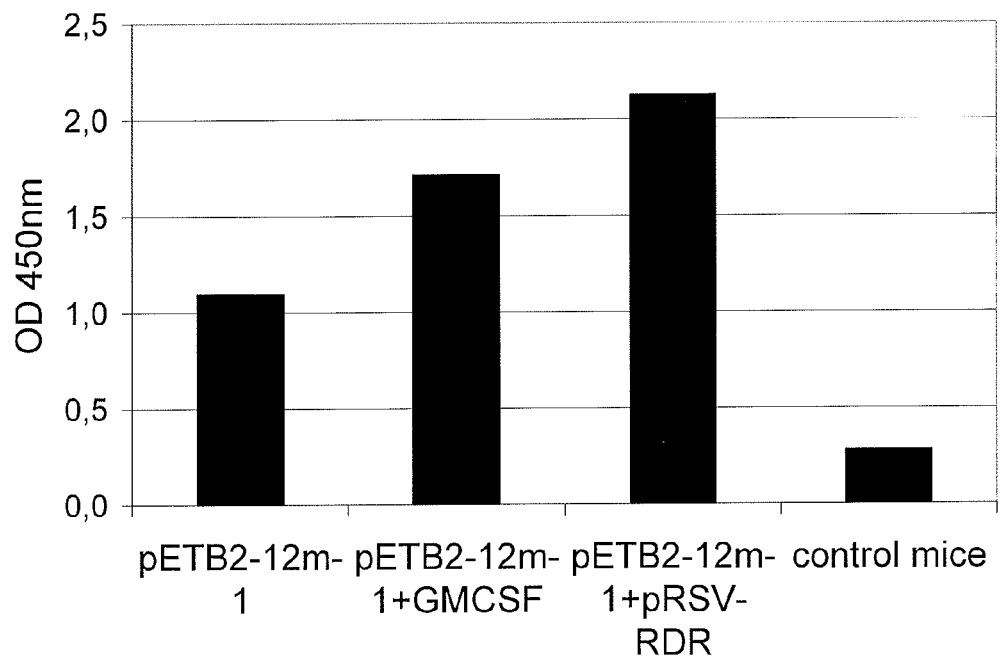

The results indicate that after two immunizations the best titers were detected in the group where genetic adjuvant pRSV-RDR was mixed with the antigen encoding plasmid. (FIG. 7)

EXAMPLE 6

Adjuvant Effect of the Expression of the SFV Replicase on the Cell Mediated Immune Response in Mice Three different groups of mice (Balb/c) 4 or 5 mice per group were immunized with gene gun 2 times with 4 week intervals. One microgram of plasmid DNA was administrated with both immunizations. The plasmid vector GTU-MultiHIV (encoding selected genes from HIV-1) is an experimental DNA vaccine for HIV-1. When GTU-MultiHIV plasmid was co-administrated with the adjuvant pRSV-RDR either on the first or the second immunization then 0.8 µg of GTU-MultiHIV and 0.2 µg of adjuvant plasmid were mixed together. For those mice receiving GTU-MultiHIV vector alone, 1 µg of plasmid DNA was used. Mice were sacrificed 10 days after the second immunization. Interferon γ and granzyme B ELISPOT analysis was performed with freshly isolated splenocytes. For stimulating cells one single peptide derived from p24 protein of HIV-1 (AMQMLKETI) and one from Env protein of HIV-1 (RGPGRAFVTI) was used, which are known to be presented by MHC class I molecules of Balb/c mice.

The results indicate that the time of co-administration of the adjuvant SFV replicase has a complex effect on the cellular immune response. Adding adjuvant to the immunization mixture increases interferon gamma response compared to animals who received only GTU-MultiHIV. Different functional capabilities of the cells are revealed after granzyme B expression analysis. Adjuvant augments granzyme B response nearly 3 fold when administered to mice with the first immunization.

```
Tyr Pro Thr Tyr Ala Thr Asn Trp Ala Asp Glu Gln Val Leu Gln Ala
    195                 200                 205

Arg Asn Ile Gly Leu Cys Ala Ala Ser Leu Thr Glu Gly Arg Leu Gly
    210                 215                 220

Lys Leu Ser Ile Leu Arg Lys Lys Gln Leu Lys Pro Cys Asp Thr Val
225                 230                 235                 240

Met Phe Ser Val Gly Ser Thr Leu Tyr Thr Glu Ser Arg Lys Leu Leu
                245                 250                 255

Arg Ser Trp His Leu Pro Ser Val Phe His Leu Lys Gly Lys Gln Ser
                260                 265                 270

Phe Thr Cys Arg Cys Asp Thr Ile Val Ser Cys Glu Gly Tyr Val Val
            275                 280                 285

Lys Lys Ile Thr Met Cys Pro Gly Leu Tyr Gly Lys Thr Val Gly Tyr
        290                 295                 300

Ala Val Thr Tyr His Ala Glu Gly Phe Leu Val Cys Lys Thr Thr Asp
305                 310                 315                 320

Thr Val Lys Gly Glu Arg Val Ser Phe Pro Val Cys Thr Tyr Val Pro
                325                 330                 335

Ser Thr Ile Cys Asp Gln Met Thr Gly Ile Leu Ala Thr Asp Val Thr
                340                 345                 350

Pro Glu Asp Ala Gln Lys Leu Leu Val Gly Leu Asn Gln Arg Ile Val
            355                 360                 365

Val Asn Gly Arg Thr Gln Arg Asn Thr Asn Thr Met Lys Asn Tyr Leu
    370                 375                 380

Leu Pro Ile Val Ala Val Ala Phe Ser Lys Trp Ala Arg Glu Tyr Lys
385                 390                 395                 400

Ala Asp Leu Asp Asp Glu Lys Pro Leu Gly Val Arg Glu Arg Ser Leu
                405                 410                 415

Thr Cys Cys Cys Leu Trp Ala Phe Lys Thr Arg Lys Met His Thr Met
                420                 425                 430

Tyr Lys Lys Pro Asp Thr Gln Thr Ile Val Lys Val Pro Ser Glu Phe
            435                 440                 445

Asn Ser Phe Val Ile Pro Ser Leu Trp Ser Thr Gly Leu Ala Ile Pro
    450                 455                 460

Val Arg Ser Arg Ile Lys Met Leu Leu Ala Lys Lys Thr Lys Arg Glu
465                 470                 475                 480

Leu Ile Pro Val Leu Asp Ala Ser Ser Ala Arg Asp Ala Glu Gln Glu
                485                 490                 495

Glu Lys Glu Arg Leu Glu Ala Glu Leu Thr Arg Glu Ala Leu Pro Pro
                500                 505                 510

Leu Val Pro Ile Ala Pro Ala Glu Thr Gly Val Val Asp Val Asp Val
            515                 520                 525

Glu Glu Leu Glu Tyr His Ala Gly Ala Gly Val Val Glu Thr Pro Arg
    530                 535                 540

Ser Ala Leu Lys Val Thr Ala Gln Pro Asn Asp Val Leu Leu Gly Asn
545                 550                 555                 560

Tyr Val Val Leu Ser Pro Gln Thr Val Leu Lys Ser Ser Lys Leu Ala
                565                 570                 575

Pro Val His Pro Leu Ala Glu Gln Val Lys Ile Ile Thr His Asn Gly
            580                 585                 590

Arg Ala Gly Arg Tyr Gln Val Asp Gly Tyr Asp Gly Arg Val Leu Leu
    595                 600                 605
```

-continued

Pro Cys Gly Ser Ala Ile Pro Val Pro Glu Phe Gln Ala Leu Ser Glu
610                 615                 620

Ser Ala Thr Met Val Tyr Asn Glu Arg Glu Phe Val Asn Arg Lys Leu
625                 630                 635                 640

Tyr His Ile Ala Val His Gly Pro Ser Leu Asn Thr Asp Glu Asn
        645                 650                 655

Tyr Glu Lys Val Arg Ala Glu Arg Thr Asp Ala Glu Tyr Val Phe Asp
        660                 665                 670

Val Asp Lys Cys Cys Val Lys Arg Glu Glu Ala Ser Gly Leu Val
        675                 680                 685

Leu Val Gly Glu Leu Thr Asn Pro Pro Phe His Glu Phe Ala Tyr Glu
690                 695                 700

Gly Leu Lys Ile Arg Pro Ser Ala Pro Tyr Lys Thr Thr Val Gly
705                 710                 715                 720

Val Phe Gly Val Pro Gly Ser Gly Lys Ser Ala Ile Ile Lys Ser Leu
                725                 730                 735

Val Thr Lys His Asp Leu Val Thr Ser Gly Lys Lys Glu Asn Cys Gln
        740                 745                 750

Glu Ile Val Asn Asp Val Lys Lys His Arg Gly Leu Asp Ile Gln Ala
        755                 760                 765

Lys Thr Val Asp Ser Ile Leu Leu Asn Gly Cys Arg Arg Ala Val Asp
770                 775                 780

Ile Leu Tyr Val Asp Glu Ala Phe Ala Cys His Ser Gly Thr Leu Leu
785                 790                 795                 800

Ala Leu Ile Ala Leu Val Lys Pro Arg Ser Lys Val Val Leu Cys Gly
                805                 810                 815

Asp Pro Lys Gln Cys Gly Phe Phe Asn Met Met Gln Leu Lys Val Asn
        820                 825                 830

Phe Asn His Asn Ile Cys Thr Glu Val Cys His Lys Ser Ile Ser Arg
        835                 840                 845

Arg Cys Thr Arg Pro Val Thr Ala Ile Val Ser Thr Leu His Tyr Gly
        850                 855                 860

Gly Lys Met Arg Thr Thr Asn Pro Cys Asn Lys Pro Ile Ile Ile Asp
865                 870                 875                 880

Thr Thr Gly Gln Thr Lys Pro Lys Pro Gly Asp Ile Val Leu Thr Cys
                885                 890                 895

Phe Arg Gly Trp Val Lys Gln Leu Gln Leu Asp Tyr Arg Gly His Glu
        900                 905                 910

Val Met Thr Ala Ala Ser Gln Gly Leu Thr Arg Lys Gly Val Tyr
        915                 920                 925

Ala Val Arg Gln Lys Val Asn Glu Asn Pro Leu Tyr Ala Pro Ala Ser
930                 935                 940

Glu His Val Asn Val Leu Leu Thr Arg Thr Glu Asp Arg Leu Val Trp
945                 950                 955                 960

Lys Thr Leu Ala Gly Asp Pro Trp Ile Lys Val Leu Ser Asn Ile Pro
                965                 970                 975

Gln Gly Asn Phe Thr Ala Thr Leu Glu Glu Trp Gln Glu Glu His Asp
        980                 985                 990

Lys Ile Met Lys Val Ile Glu Gly Pro Ala Ala Pro Val Asp Ala Phe
        995                 1000                1005

Gln Asn Lys Ala Asn Val Cys Trp Ala Lys Ser Leu Val Pro Val
    1010                1015                1020

Leu Asp Thr Ala Gly Ile Arg Leu Thr Ala Glu Glu Trp Ser Thr

-continued

```
            1025                1030                1035
Ile Ile Thr Ala Phe Lys Glu Asp Arg Ala Tyr Ser Pro Val Val
    1040                1045                1050
Ala Leu Asn Glu Ile Cys Thr Lys Tyr Tyr Gly Val Asp Leu Asp
    1055                1060                1065
Ser Gly Leu Phe Ser Ala Pro Lys Val Ser Leu Tyr Tyr Glu Asn
    1070                1075                1080
Asn His Trp Asp Asn Arg Pro Gly Gly Arg Met Tyr Gly Phe Asn
    1085                1090                1095
Ala Ala Thr Ala Ala Arg Leu Glu Ala Arg His Thr Phe Leu Lys
    1100                1105                1110
Gly Gln Trp His Thr Gly Lys Gln Ala Val Ile Ala Glu Arg Lys
    1115                1120                1125
Ile Gln Pro Leu Ser Val Leu Asp Asn Val Ile Pro Ile Asn Arg
    1130                1135                1140
Arg Leu Pro His Ala Leu Val Ala Glu Tyr Lys Thr Val Lys Gly
    1145                1150                1155
Ser Arg Val Glu Trp Leu Val Asn Lys Val Arg Gly Tyr His Val
    1160                1165                1170
Leu Leu Val Ser Glu Tyr Asn Leu Ala Leu Pro Arg Arg Arg Val
    1175                1180                1185
Thr Trp Leu Ser Pro Leu Asn Val Thr Gly Ala Asp Arg Cys Tyr
    1190                1195                1200
Asp Leu Ser Leu Gly Leu Pro Ala Asp Ala Gly Arg Phe Asp Leu
    1205                1210                1215
Val Phe Val Asn Ile His Thr Glu Phe Arg Ile His His Tyr Gln
    1220                1225                1230
Gln Cys Val Asp His Ala Met Lys Leu Gln Met Leu Gly Gly Asp
    1235                1240                1245
Ala Leu Arg Leu Leu Lys Pro Gly Gly Ser Leu Leu Met Arg Ala
    1250                1255                1260
Tyr Gly Tyr Ala Asp Lys Ile Ser Glu Ala Val Val Ser Ser Leu
    1265                1270                1275
Ser Arg Lys Phe Ser Ser Ala Arg Val Leu Arg Pro Asp Cys Val
    1280                1285                1290
Thr Ser Asn Thr Glu Val Phe Leu Leu Phe Ser Asn Phe Asp Asn
    1295                1300                1305
Gly Lys Arg Pro Ser Thr Leu His Gln Met Asn Thr Lys Leu Ser
    1310                1315                1320
Ala Val Tyr Ala Gly Glu Ala Met His Thr Ala Gly Cys Ala Pro
    1325                1330                1335
Ser Tyr Arg Val Lys Arg Ala Asp Ile Ala Thr Cys Thr Glu Ala
    1340                1345                1350
Ala Val Val Asn Ala Ala Asn Ala Arg Gly Thr Val Gly Asp Gly
    1355                1360                1365
Val Cys Arg Ala Val Ala Lys Lys Trp Pro Ser Ala Phe Lys Gly
    1370                1375                1380
Glu Ala Thr Pro Val Gly Thr Ile Lys Thr Val Met Cys Gly Ser
    1385                1390                1395
Tyr Pro Val Ile His Ala Val Ala Pro Asn Phe Ser Ala Thr Thr
    1400                1405                1410
Glu Ala Glu Gly Asp Arg Glu Leu Ala Ala Val Tyr Arg Ala Val
    1415                1420                1425
```

```
Ala Ala Glu Val Asn Arg Leu Ser Leu Ser Val Ala Ile Pro
1430                1435                 1440

Leu Leu Ser Thr Gly Val Phe Ser Gly Gly Arg Asp Arg Leu Gln
1445                1450                 1455

Gln Ser Leu Asn His Leu Phe Thr Ala Met Asp Ala Thr Asp Ala
1460                1465                 1470

Asp Val Thr Ile Tyr Cys Arg Asp Lys Ser Trp Glu Lys Lys Ile
1475                1480                 1485

Gln Glu Ala Ile Asp Met Arg Thr Ala Val Glu Leu Leu Asn Asp
1490                1495                 1500

Asp Val Glu Leu Thr Thr Asp Leu Val Arg Val His Pro Asp Ser
1505                1510                 1515

Ser Leu Val Gly Arg Lys Gly Tyr Ser Thr Thr Asp Gly Ser Leu
1520                1525                 1530

Tyr Ser Tyr Phe Glu Gly Thr Lys Phe Asn Gln Ala Ala Ile Asp
1535                1540                 1545

Met Ala Glu Ile Leu Thr Leu Trp Pro Arg Leu Gln Glu Ala Asn
1550                1555                 1560

Glu Gln Ile Cys Leu Tyr Ala Leu Gly Glu Thr Met Asp Asn Ile
1565                1570                 1575

Arg Ser Lys Cys Pro Val Asn Asp Ser Asp Ser Ser Thr Pro Pro
1580                1585                 1590

Arg Thr Val Pro Cys Leu Cys Arg Tyr Ala Met Thr Ala Glu Arg
1595                1600                 1605

Ile Ala Arg Leu Arg Ser His Gln Val Lys Ser Met Val Val Cys
1610                1615                 1620

Ser Ser Phe Pro Leu Pro Lys Tyr His Val Asp Gly Val Gln Lys
1625                1630                 1635

Val Lys Cys Glu Lys Val Leu Leu Phe Asp Pro Thr Val Pro Ser
1640                1645                 1650

Val Val Ser Pro Arg Lys Tyr Ala Ala Ser Thr Thr Asp His Ser
1655                1660                 1665

Asp Arg Ser Leu Arg Gly Phe Asp Leu Asp Trp Thr Thr Asp Ser
1670                1675                 1680

Ser Ser Thr Ala Ser Asp Thr Met Ser Leu Pro Ser Leu Gln Ser
1685                1690                 1695

Cys Asp Ile Asp Ser Ile Tyr Glu Pro Met Ala Pro Ile Val Val
1700                1705                 1710

Thr Ala Asp Val His Pro Glu Pro Ala Gly Ile Ala Asp Leu Ala
1715                1720                 1725

Ala Asp Val His Pro Glu Pro Ala Asp His Val Asp Leu Glu Asn
1730                1735                 1740

Pro Ile Pro Pro Pro Arg Pro Lys Arg Ala Ala Tyr Leu Ala Ser
1745                1750                 1755

Arg Ala Ala Glu Arg Pro Val Pro Ala Pro Arg Lys Pro Thr Pro
1760                1765                 1770

Ala Pro Arg Thr Ala Phe Arg Asn Lys Leu Pro Leu Thr Phe Gly
1775                1780                 1785

Asp Phe Asp Glu His Glu Val Asp Ala Leu Ala Ser Gly Ile Thr
1790                1795                 1800

Phe Gly Asp Phe Asp Asp Val Leu Arg Leu Gly Arg Ala Gly Ala
1805                1810                 1815
```

```
Tyr Ile Phe Ser Ser Asp Thr Gly Ser Gly His Leu Gln Gln Lys
    1820            1825            1830

Ser Val Arg Gln His Asn Leu Gln Cys Ala Gln Leu Asp Ala Val
    1835            1840            1845

Glu Glu Glu Lys Met Tyr Pro Pro Lys Leu Asp Thr Glu Arg Glu
    1850            1855            1860

Lys Leu Leu Leu Leu Lys Met Gln Met His Pro Ser Glu Ala Asn
    1865            1870            1875

Lys Ser Arg Tyr Gln Ser Arg Lys Val Glu Asn Met Lys Ala Thr
    1880            1885            1890

Val Val Asp Arg Leu Thr Ser Gly Ala Arg Leu Tyr Thr Gly Ala
    1895            1900            1905

Asp Val Gly Arg Ile Pro Thr Tyr Ala Val Arg Tyr Pro Arg Pro
    1910            1915            1920

Val Tyr Ser Pro Thr Val Ile Glu Arg Phe Ser Ser Pro Asp Val
    1925            1930            1935

Ala Ile Ala Ala Cys Asn Glu Tyr Leu Ser Arg Asn Tyr Pro Thr
    1940            1945            1950

Val Ala Ser Tyr Gln Ile Thr Asp Glu Tyr Asp Ala Tyr Leu Asp
    1955            1960            1965

Met Val Asp Gly Ser Asp Ser Cys Leu Asp Arg Ala Thr Phe Cys
    1970            1975            1980

Pro Ala Lys Leu Arg Cys Tyr Pro Lys His His Ala Tyr His Gln
    1985            1990            1995

Pro Thr Val Arg Ser Ala Val Pro Ser Pro Phe Gln Asn Thr Leu
    2000            2005            2010

Gln Asn Val Leu Ala Ala Ala Thr Lys Arg Asn Cys Asn Val Thr
    2015            2020            2025

Gln Met Arg Glu Leu Pro Thr Met Asp Ser Ala Val Phe Asn Val
    2030            2035            2040

Glu Cys Phe Lys Arg Tyr Ala Cys Ser Gly Glu Tyr Trp Glu Glu
    2045            2050            2055

Tyr Ala Lys Gln Pro Ile Arg Ile Thr Thr Glu Asn Ile Thr Thr
    2060            2065            2070

Tyr Val Thr Lys Leu Lys Gly Pro Lys Ala Ala Ala Leu Phe Ala
    2075            2080            2085

Lys Thr His Asn Leu Val Pro Leu Gln Glu Val Pro Met Asp Arg
    2090            2095            2100

Phe Thr Val Asp Met Lys Arg Asp Val Lys Val Thr Pro Gly Thr
    2105            2110            2115

Lys His Thr Glu Glu Arg Pro Lys Val Gln Val Ile Gln Ala Ala
    2120            2125            2130

Glu Pro Leu Ala Thr Ala Tyr Leu Cys Gly Ile His Arg Glu Leu
    2135            2140            2145

Val Arg Arg Leu Asn Ala Val Leu Arg Pro Asn Val His Thr Leu
    2150            2155            2160

Phe Asp Met Ser Ala Glu Asp Phe Asp Ala Ile Ile Ala Ser His
    2165            2170            2175

Phe His Pro Gly Asp Pro Val Leu Glu Thr Asp Ile Ala Ser Phe
    2180            2185            2190

Asp Lys Ser Gln Asp Asp Ser Leu Ala Leu Thr Gly Leu Met Ile
    2195            2200            2205

Leu Glu Asp Leu Gly Val Asp Gln Tyr Leu Leu Asp Leu Ile Glu
```

```
                    2210                2215                2220

Ala  Ala  Phe  Gly  Glu  Ile  Ser  Ser  Cys  His  Leu  Pro  Thr  Gly  Thr
               2225                2230                2235

Arg  Phe  Lys  Phe  Gly  Ala  Met  Met  Lys  Ser  Gly  Met  Phe  Leu  Thr
          2240                2245                2250

Leu  Phe  Ile  Asn  Thr  Val  Leu  Asn  Ile  Thr  Ile  Ala  Ser  Arg  Val
     2255                2260                2265

Leu  Glu  Gln  Arg  Leu  Thr  Asp  Ser  Ala  Cys  Ala  Ala  Phe  Ile  Gly
2270                2275                2280

Asp  Asp  Asn  Ile  Val  His  Gly  Val  Ile  Ser  Asp  Lys  Leu  Met  Ala
               2285                2290                2295

Glu  Arg  Cys  Ala  Ser  Trp  Val  Asn  Met  Glu  Val  Lys  Ile  Ile  Asp
          2300                2305                2310

Ala  Val  Met  Gly  Glu  Lys  Pro  Pro  Tyr  Phe  Cys  Gly  Gly  Phe  Ile
     2315                2320                2325

Val  Phe  Asp  Ser  Val  Thr  Gln  Thr  Ala  Cys  Arg  Val  Ser  Asp  Pro
2330                2335                2340

Leu  Lys  Arg  Leu  Phe  Lys  Leu  Gly  Lys  Pro  Leu  Thr  Ala  Glu  Asp
               2345                2350                2355

Lys  Gln  Asp  Glu  Asp  Arg  Arg  Arg  Ala  Leu  Ser  Asp  Glu  Val  Ser
          2360                2365                2370

Lys  Trp  Phe  Arg  Thr  Gly  Leu  Gly  Ala  Glu  Leu  Glu  Val  Ala  Leu
     2375                2380                2385

Thr  Ser  Arg  Tyr  Glu  Val  Glu  Gly  Cys  Lys  Ser  Ile  Leu  Ile  Ala
2390                2395                2400

Met  Ala  Thr  Leu  Ala  Arg  Asp  Ile  Lys  Ala  Phe  Lys  Lys  Leu  Arg
               2405                2410                2415

Gly  Pro  Val  Ile  His  Leu  Tyr  Gly  Gly  Pro  Arg  Leu  Val  Arg
          2420                2425                2430

<210> SEQ ID NO 2
<211> LENGTH: 2432
<212> TYPE: PRT
<213> ORGANISM: Artificial
<220> FEATURE:
<223> OTHER INFORMATION: Amino acid sequence of the SFV replicase with
      the RDR mutation in positions 1185-1187

<400> SEQUENCE: 2

Met  Ala  Ala  Lys  Val  His  Val  Asp  Ile  Glu  Ala  Asp  Ser  Pro  Phe  Ile
1                   5                   10                  15

Lys  Ser  Leu  Gln  Lys  Ala  Phe  Pro  Ser  Phe  Glu  Val  Glu  Ser  Leu  Gln
               20                  25                  30

Val  Thr  Pro  Asn  Asp  His  Ala  Asn  Ala  Arg  Ala  Phe  Ser  His  Leu  Ala
          35                  40                  45

Thr  Lys  Leu  Ile  Glu  Gln  Glu  Thr  Asp  Lys  Asp  Thr  Leu  Ile  Leu  Asp
     50                  55                  60

Ile  Gly  Ser  Ala  Pro  Ser  Arg  Arg  Met  Met  Ser  Thr  His  Lys  Tyr  His
65                  70                  75                  80

Cys  Val  Cys  Pro  Met  Arg  Ser  Ala  Glu  Asp  Pro  Glu  Arg  Leu  Val  Cys
                    85                  90                  95

Tyr  Ala  Lys  Lys  Leu  Ala  Ala  Ala  Ser  Gly  Lys  Val  Leu  Asp  Arg  Glu
               100                 105                 110

Ile  Ala  Gly  Lys  Ile  Thr  Asp  Leu  Gln  Thr  Val  Met  Ala  Thr  Pro  Asp
          115                 120                 125
```

-continued

```
Ala Glu Ser Pro Thr Phe Cys Leu His Thr Asp Val Thr Cys Arg Thr
130                 135                 140

Ala Ala Glu Val Ala Val Tyr Gln Asp Val Tyr Ala Val His Ala Pro
145                 150                 155                 160

Thr Ser Leu Tyr His Gln Ala Met Lys Gly Val Arg Thr Ala Tyr Trp
            165                 170                 175

Ile Gly Phe Asp Thr Thr Pro Phe Met Phe Asp Ala Leu Ala Gly Ala
            180                 185                 190

Tyr Pro Thr Tyr Ala Thr Asn Trp Ala Asp Glu Gln Val Leu Gln Ala
            195                 200                 205

Arg Asn Ile Gly Leu Cys Ala Ala Ser Leu Thr Glu Gly Arg Leu Gly
210                 215                 220

Lys Leu Ser Ile Leu Arg Lys Lys Gln Leu Lys Pro Cys Asp Thr Val
225                 230                 235                 240

Met Phe Ser Val Gly Ser Thr Leu Tyr Thr Glu Ser Arg Lys Leu Leu
            245                 250                 255

Arg Ser Trp His Leu Pro Ser Val Phe His Leu Lys Gly Lys Gln Ser
            260                 265                 270

Phe Thr Cys Arg Cys Asp Thr Ile Val Ser Cys Glu Gly Tyr Val Val
            275                 280                 285

Lys Lys Ile Thr Met Cys Pro Gly Leu Tyr Gly Lys Thr Val Gly Tyr
290                 295                 300

Ala Val Thr Tyr His Ala Glu Gly Phe Leu Val Cys Lys Thr Thr Asp
305                 310                 315                 320

Thr Val Lys Gly Glu Arg Val Ser Phe Pro Val Cys Thr Tyr Val Pro
            325                 330                 335

Ser Thr Ile Cys Asp Gln Met Thr Gly Ile Leu Ala Thr Asp Val Thr
            340                 345                 350

Pro Glu Asp Ala Gln Lys Leu Leu Val Gly Leu Asn Gln Arg Ile Val
            355                 360                 365

Val Asn Gly Arg Thr Gln Arg Asn Thr Asn Thr Met Lys Asn Tyr Leu
370                 375                 380

Leu Pro Ile Val Ala Val Ala Phe Ser Lys Trp Ala Arg Glu Tyr Lys
385                 390                 395                 400

Ala Asp Leu Asp Asp Glu Lys Pro Leu Gly Val Arg Glu Arg Ser Leu
            405                 410                 415

Thr Cys Cys Cys Leu Trp Ala Phe Lys Thr Arg Lys Met His Thr Met
            420                 425                 430

Tyr Lys Lys Pro Asp Thr Gln Thr Ile Val Lys Val Pro Ser Glu Phe
            435                 440                 445

Asn Ser Phe Val Ile Pro Ser Leu Trp Ser Thr Gly Leu Ala Ile Pro
450                 455                 460

Val Arg Ser Arg Ile Lys Met Leu Leu Ala Lys Lys Thr Lys Arg Glu
465                 470                 475                 480

Leu Ile Pro Val Leu Asp Ala Ser Ser Ala Arg Asp Ala Glu Gln Glu
            485                 490                 495

Glu Lys Glu Arg Leu Glu Ala Glu Leu Thr Arg Glu Ala Leu Pro Pro
            500                 505                 510

Leu Val Pro Ile Ala Pro Ala Glu Thr Gly Val Val Asp Val Asp Val
            515                 520                 525

Glu Glu Leu Glu Tyr His Ala Gly Ala Gly Val Glu Thr Pro Arg
530                 535                 540

Ser Ala Leu Lys Val Thr Ala Gln Pro Asn Asp Val Leu Leu Gly Asn
```

-continued

```
        545                 550                 555                 560
Tyr Val Val Leu Ser Pro Gln Thr Val Leu Lys Ser Ser Lys Leu Ala
                565                 570                 575
Pro Val His Pro Leu Ala Glu Gln Val Lys Ile Ile Thr His Asn Gly
                580                 585                 590
Arg Ala Gly Arg Tyr Gln Val Asp Gly Tyr Asp Gly Arg Val Leu Leu
                595                 600                 605
Pro Cys Gly Ser Ala Ile Pro Val Pro Glu Phe Gln Ala Leu Ser Glu
                610                 615                 620
Ser Ala Thr Met Val Tyr Asn Glu Arg Glu Phe Val Asn Arg Lys Leu
625                 630                 635                 640
Tyr His Ile Ala Val His Gly Pro Ser Leu Asn Thr Asp Glu Glu Asn
                645                 650                 655
Tyr Glu Lys Val Arg Ala Glu Arg Thr Asp Ala Glu Tyr Val Phe Asp
                660                 665                 670
Val Asp Lys Lys Cys Cys Val Lys Arg Glu Ala Ser Gly Leu Val
                675                 680                 685
Leu Val Gly Glu Leu Thr Asn Pro Pro Phe His Glu Phe Ala Tyr Glu
                690                 695                 700
Gly Leu Lys Ile Arg Pro Ser Ala Pro Tyr Lys Thr Thr Val Val Gly
705                 710                 715                 720
Val Phe Gly Val Pro Gly Ser Gly Lys Ser Ala Ile Ile Lys Ser Leu
                725                 730                 735
Val Thr Lys His Asp Leu Val Thr Ser Gly Lys Lys Glu Asn Cys Gln
                740                 745                 750
Glu Ile Val Asn Asp Val Lys Lys His Arg Gly Leu Asp Ile Gln Ala
                755                 760                 765
Lys Thr Val Asp Ser Ile Leu Leu Asn Gly Cys Arg Arg Ala Val Asp
                770                 775                 780
Ile Leu Tyr Val Asp Glu Ala Phe Ala Cys His Ser Gly Thr Leu Leu
785                 790                 795                 800
Ala Leu Ile Ala Leu Val Lys Pro Arg Ser Lys Val Val Leu Cys Gly
                805                 810                 815
Asp Pro Lys Gln Cys Gly Phe Phe Asn Met Met Gln Leu Lys Val Asn
                820                 825                 830
Phe Asn His Asn Ile Cys Thr Glu Val Cys His Lys Ser Ile Ser Arg
                835                 840                 845
Arg Cys Thr Arg Pro Val Thr Ala Ile Val Ser Thr Leu His Tyr Gly
                850                 855                 860
Gly Lys Met Arg Thr Thr Asn Pro Cys Asn Lys Pro Ile Ile Ile Asp
865                 870                 875                 880
Thr Thr Gly Gln Thr Lys Pro Lys Pro Gly Asp Ile Val Leu Thr Cys
                885                 890                 895
Phe Arg Gly Trp Val Lys Gln Leu Gln Leu Asp Tyr Arg Gly His Glu
                900                 905                 910
Val Met Thr Ala Ala Ala Ser Gln Gly Leu Thr Arg Lys Gly Val Tyr
                915                 920                 925
Ala Val Arg Gln Lys Val Asn Glu Asn Pro Leu Tyr Ala Pro Ala Ser
                930                 935                 940
Glu His Val Asn Val Leu Leu Thr Arg Thr Glu Asp Arg Leu Val Trp
945                 950                 955                 960
Lys Thr Leu Ala Gly Asp Pro Trp Ile Lys Val Leu Ser Asn Ile Pro
                965                 970                 975
```

-continued

```
Gln Gly Asn Phe Thr Ala Thr Leu Glu Glu Trp Gln Glu His Asp
            980                 985                 990

Lys Ile Met Lys Val Ile Glu Gly Pro Ala Ala Pro Val Asp Ala Phe
        995                1000                1005

Gln Asn Lys Ala Asn Val Cys Trp Ala Lys Ser Leu Val Pro Val
    1010                1015                1020

Leu Asp Thr Ala Gly Ile Arg Leu Thr Ala Glu Glu Trp Ser Thr
    1025                1030                1035

Ile Ile Thr Ala Phe Lys Glu Asp Arg Ala Tyr Ser Pro Val Val
    1040                1045                1050

Ala Leu Asn Glu Ile Cys Thr Lys Tyr Tyr Gly Val Asp Leu Asp
    1055                1060                1065

Ser Gly Leu Phe Ser Ala Pro Lys Val Ser Leu Tyr Tyr Glu Asn
    1070                1075                1080

Asn His Trp Asp Asn Arg Pro Gly Gly Arg Met Tyr Gly Phe Asn
    1085                1090                1095

Ala Ala Thr Ala Ala Arg Leu Glu Ala Arg His Thr Phe Leu Lys
    1100                1105                1110

Gly Gln Trp His Thr Gly Lys Gln Ala Val Ile Ala Glu Arg Lys
    1115                1120                1125

Ile Gln Pro Leu Ser Val Leu Asp Asn Val Ile Pro Ile Asn Arg
    1130                1135                1140

Arg Leu Pro His Ala Leu Val Ala Glu Tyr Lys Thr Val Lys Gly
    1145                1150                1155

Ser Arg Val Glu Trp Leu Val Asn Lys Val Arg Gly Tyr His Val
    1160                1165                1170

Leu Leu Val Ser Glu Tyr Asn Leu Ala Leu Pro Arg Asp Arg Val
    1175                1180                1185

Thr Trp Leu Ser Pro Leu Asn Val Thr Gly Ala Asp Arg Cys Tyr
    1190                1195                1200

Asp Leu Ser Leu Gly Leu Pro Ala Asp Ala Gly Arg Phe Asp Leu
    1205                1210                1215

Val Phe Val Asn Ile His Thr Glu Phe Arg Ile His His Tyr Gln
    1220                1225                1230

Gln Cys Val Asp His Ala Met Lys Leu Gln Met Leu Gly Gly Asp
    1235                1240                1245

Ala Leu Arg Leu Leu Lys Pro Gly Gly Ser Leu Leu Met Arg Ala
    1250                1255                1260

Tyr Gly Tyr Ala Asp Lys Ile Ser Glu Ala Val Val Ser Ser Leu
    1265                1270                1275

Ser Arg Lys Phe Ser Ser Ala Arg Val Leu Arg Pro Asp Cys Val
    1280                1285                1290

Thr Ser Asn Thr Glu Val Phe Leu Leu Phe Ser Asn Phe Asp Asn
    1295                1300                1305

Gly Lys Arg Pro Ser Thr Leu His Gln Met Asn Thr Lys Leu Ser
    1310                1315                1320

Ala Val Tyr Ala Gly Glu Ala Met His Thr Ala Gly Cys Ala Pro
    1325                1330                1335

Ser Tyr Arg Val Lys Arg Ala Asp Ile Ala Thr Cys Thr Glu Ala
    1340                1345                1350

Ala Val Val Asn Ala Ala Asn Ala Arg Gly Thr Val Gly Asp Gly
    1355                1360                1365
```

| | | | | | | | | | | | |
|---|---|---|---|---|---|---|---|---|---|---|---|
|Val|Cys|Arg|Ala|Val|Ala|Lys|Lys|Trp|Pro|Ser|Ala|Phe|Lys|Gly|
|1370| | | | |1375| | | | |1380| | | | |

Glu Ala Thr Pro Val Gly Thr Ile Lys Thr Val Met Cys Gly Ser
1385 1390 1395

Tyr Pro Val Ile His Ala Val Ala Pro Asn Phe Ser Ala Thr Thr
1400 1405 1410

Glu Ala Glu Gly Asp Arg Glu Leu Ala Ala Val Tyr Arg Ala Val
1415 1420 1425

Ala Ala Glu Val Asn Arg Leu Ser Leu Ser Ser Val Ala Ile Pro
1430 1435 1440

Leu Leu Ser Thr Gly Val Phe Ser Gly Gly Arg Asp Arg Leu Gln
1445 1450 1455

Gln Ser Leu Asn His Leu Phe Thr Ala Met Asp Ala Thr Asp Ala
1460 1465 1470

Asp Val Thr Ile Tyr Cys Arg Asp Lys Ser Trp Glu Lys Lys Ile
1475 1480 1485

Gln Glu Ala Ile Asp Met Arg Thr Ala Val Glu Leu Leu Asn Asp
1490 1495 1500

Asp Val Glu Leu Thr Thr Asp Leu Val Arg Val His Pro Asp Ser
1505 1510 1515

Ser Leu Val Gly Arg Lys Gly Tyr Ser Thr Thr Asp Gly Ser Leu
1520 1525 1530

Tyr Ser Tyr Phe Glu Gly Thr Lys Phe Asn Gln Ala Ala Ile Asp
1535 1540 1545

Met Ala Glu Ile Leu Thr Leu Trp Pro Arg Leu Gln Glu Ala Asn
1550 1555 1560

Glu Gln Ile Cys Leu Tyr Ala Leu Gly Glu Thr Met Asp Asn Ile
1565 1570 1575

Arg Ser Lys Cys Pro Val Asn Asp Ser Asp Ser Thr Pro Pro
1580 1585 1590

Arg Thr Val Pro Cys Leu Cys Arg Tyr Ala Met Thr Ala Glu Arg
1595 1600 1605

Ile Ala Arg Leu Arg Ser His Gln Val Lys Ser Met Val Val Cys
1610 1615 1620

Ser Ser Phe Pro Leu Pro Lys Tyr His Val Asp Gly Val Gln Lys
1625 1630 1635

Val Lys Cys Glu Lys Val Leu Leu Phe Asp Pro Thr Val Pro Ser
1640 1645 1650

Val Val Ser Pro Arg Lys Tyr Ala Ala Ser Thr Thr Asp His Ser
1655 1660 1665

Asp Arg Ser Leu Arg Gly Phe Asp Leu Asp Trp Thr Thr Asp Ser
1670 1675 1680

Ser Ser Thr Ala Ser Asp Thr Met Ser Leu Pro Ser Leu Gln Ser
1685 1690 1695

Cys Asp Ile Asp Ser Ile Tyr Glu Pro Met Ala Pro Ile Val Val
1700 1705 1710

Thr Ala Asp Val His Pro Glu Pro Ala Gly Ile Ala Asp Leu Ala
1715 1720 1725

Ala Asp Val His Pro Glu Pro Ala Asp His Val Asp Leu Glu Asn
1730 1735 1740

Pro Ile Pro Pro Pro Arg Pro Lys Arg Ala Ala Tyr Leu Ala Ser
1745 1750 1755

Arg Ala Ala Glu Arg Pro Val Pro Ala Pro Arg Lys Pro Thr Pro

-continued

```
            1760                1765                1770
Ala Pro Arg Thr Ala Phe Arg Asn Lys Leu Pro Leu Thr Phe Gly
    1775                1780                1785
Asp Phe Asp Glu His Glu Val Asp Ala Leu Ala Ser Gly Ile Thr
    1790                1795                1800
Phe Gly Asp Phe Asp Asp Val Leu Arg Leu Gly Arg Ala Gly Ala
    1805                1810                1815
Tyr Ile Phe Ser Ser Asp Thr Gly Ser Gly His Leu Gln Gln Lys
    1820                1825                1830
Ser Val Arg Gln His Asn Leu Gln Cys Ala Gln Leu Asp Ala Val
    1835                1840                1845
Glu Glu Glu Lys Met Tyr Pro Pro Lys Leu Asp Thr Glu Arg Glu
    1850                1855                1860
Lys Leu Leu Leu Leu Lys Met Gln Met His Pro Ser Glu Ala Asn
    1865                1870                1875
Lys Ser Arg Tyr Gln Ser Arg Lys Val Glu Asn Met Lys Ala Thr
    1880                1885                1890
Val Val Asp Arg Leu Thr Ser Gly Ala Arg Leu Tyr Thr Gly Ala
    1895                1900                1905
Asp Val Gly Arg Ile Pro Thr Tyr Ala Val Arg Tyr Pro Arg Pro
    1910                1915                1920
Val Tyr Ser Pro Thr Val Ile Glu Arg Phe Ser Ser Pro Asp Val
    1925                1930                1935
Ala Ile Ala Ala Cys Asn Glu Tyr Leu Ser Arg Asn Tyr Pro Thr
    1940                1945                1950
Val Ala Ser Tyr Gln Ile Thr Asp Glu Tyr Asp Ala Tyr Leu Asp
    1955                1960                1965
Met Val Asp Gly Ser Asp Ser Cys Leu Asp Arg Ala Thr Phe Cys
    1970                1975                1980
Pro Ala Lys Leu Arg Cys Tyr Pro Lys His His Ala Tyr His Gln
    1985                1990                1995
Pro Thr Val Arg Ser Ala Val Pro Ser Pro Phe Gln Asn Thr Leu
    2000                2005                2010
Gln Asn Val Leu Ala Ala Ala Thr Lys Arg Asn Cys Asn Val Thr
    2015                2020                2025
Gln Met Arg Glu Leu Pro Thr Met Asp Ser Ala Val Phe Asn Val
    2030                2035                2040
Glu Cys Phe Lys Arg Tyr Ala Cys Ser Gly Glu Tyr Trp Glu Glu
    2045                2050                2055
Tyr Ala Lys Gln Pro Ile Arg Ile Thr Thr Glu Asn Ile Thr Thr
    2060                2065                2070
Tyr Val Thr Lys Leu Lys Gly Pro Lys Ala Ala Ala Leu Phe Ala
    2075                2080                2085
Lys Thr His Asn Leu Val Pro Leu Gln Glu Val Pro Met Asp Arg
    2090                2095                2100
Phe Thr Val Asp Met Lys Arg Asp Val Lys Val Thr Pro Gly Thr
    2105                2110                2115
Lys His Thr Glu Glu Arg Pro Lys Val Gln Val Ile Gln Ala Ala
    2120                2125                2130
Glu Pro Leu Ala Thr Ala Tyr Leu Cys Gly Ile His Arg Glu Leu
    2135                2140                2145
Val Arg Arg Leu Asn Ala Val Leu Arg Pro Asn Val His Thr Leu
    2150                2155                2160
```

```
Phe Asp Met Ser Ala Glu Asp Phe Asp Ala Ile Ile Ala Ser His
    2165                2170                2175

Phe His Pro Gly Asp Pro Val Leu Glu Thr Asp Ile Ala Ser Phe
    2180                2185                2190

Asp Lys Ser Gln Asp Ser Leu Ala Leu Thr Gly Leu Met Ile
    2195                2200                2205

Leu Glu Asp Leu Gly Val Asp Gln Tyr Leu Leu Asp Leu Ile Glu
    2210                2215                2220

Ala Ala Phe Gly Glu Ile Ser Ser Cys His Leu Pro Thr Gly Thr
    2225                2230                2235

Arg Phe Lys Phe Gly Ala Met Met Lys Ser Gly Met Phe Leu Thr
    2240                2245                2250

Leu Phe Ile Asn Thr Val Leu Asn Ile Thr Ile Ala Ser Arg Val
    2255                2260                2265

Leu Glu Gln Arg Leu Thr Asp Ser Ala Cys Ala Ala Phe Ile Gly
    2270                2275                2280

Asp Asp Asn Ile Val His Gly Val Ile Ser Asp Lys Leu Met Ala
    2285                2290                2295

Glu Arg Cys Ala Ser Trp Val Asn Met Glu Val Lys Ile Ile Asp
    2300                2305                2310

Ala Val Met Gly Glu Lys Pro Pro Tyr Phe Cys Gly Gly Phe Ile
    2315                2320                2325

Val Phe Asp Ser Val Thr Gln Thr Ala Cys Arg Val Ser Asp Pro
    2330                2335                2340

Leu Lys Arg Leu Phe Lys Leu Gly Lys Pro Leu Thr Ala Glu Asp
    2345                2350                2355

Lys Gln Asp Glu Asp Arg Arg Arg Ala Leu Ser Asp Glu Val Ser
    2360                2365                2370

Lys Trp Phe Arg Thr Gly Leu Gly Ala Glu Leu Glu Val Ala Leu
    2375                2380                2385

Thr Ser Arg Tyr Glu Val Glu Gly Cys Lys Ser Ile Leu Ile Ala
    2390                2395                2400

Met Ala Thr Leu Ala Arg Asp Ile Lys Ala Phe Lys Lys Leu Arg
    2405                2410                2415

Gly Pro Val Ile His Leu Tyr Gly Gly Pro Arg Leu Val Arg
    2420                2425                2430

<210> SEQ ID NO 3
<211> LENGTH: 2432
<212> TYPE: PRT
<213> ORGANISM: Artificial
<220> FEATURE:
<223> OTHER INFORMATION: Amino acid sequence of the SFV replicase with
      the AAA mutation in positions 1185-1187

<400> SEQUENCE: 3

Met Ala Ala Lys Val His Val Asp Ile Glu Ala Asp Ser Pro Phe Ile
1               5                   10                  15

Lys Ser Leu Gln Lys Ala Phe Pro Ser Phe Glu Val Glu Ser Leu Gln
            20                  25                  30

Val Thr Pro Asn Asp His Ala Asn Ala Arg Ala Phe Ser His Leu Ala
        35                  40                  45

Thr Lys Leu Ile Glu Gln Glu Thr Asp Lys Asp Thr Leu Ile Leu Asp
    50                  55                  60

Ile Gly Ser Ala Pro Ser Arg Arg Met Met Ser Thr His Lys Tyr His
```

-continued

```
             65                  70                  75                  80
Cys Val Cys Pro Met Arg Ser Ala Glu Asp Pro Glu Arg Leu Val Cys
                 85                  90                  95
Tyr Ala Lys Lys Leu Ala Ala Ser Gly Lys Val Leu Asp Arg Glu
            100                 105                 110
Ile Ala Gly Lys Ile Thr Asp Leu Gln Thr Val Met Ala Thr Pro Asp
            115                 120                 125
Ala Glu Ser Pro Thr Phe Cys Leu His Thr Asp Val Thr Cys Arg Thr
            130                 135                 140
Ala Ala Glu Val Ala Val Tyr Gln Asp Val Tyr Ala Val His Ala Pro
145                 150                 155                 160
Thr Ser Leu Tyr His Gln Ala Met Lys Gly Val Arg Thr Ala Tyr Trp
                165                 170                 175
Ile Gly Phe Asp Thr Thr Pro Phe Met Phe Asp Ala Leu Ala Gly Ala
            180                 185                 190
Tyr Pro Thr Tyr Ala Thr Asn Trp Ala Asp Glu Gln Val Leu Gln Ala
                195                 200                 205
Arg Asn Ile Gly Leu Cys Ala Ala Ser Leu Thr Glu Gly Arg Leu Gly
210                 215                 220
Lys Leu Ser Ile Leu Arg Lys Lys Gln Leu Lys Pro Cys Asp Thr Val
225                 230                 235                 240
Met Phe Ser Val Gly Ser Thr Leu Tyr Thr Glu Ser Arg Lys Leu Leu
                245                 250                 255
Arg Ser Trp His Leu Pro Ser Val Phe His Leu Lys Gly Lys Gln Ser
                260                 265                 270
Phe Thr Cys Arg Cys Asp Thr Ile Val Ser Cys Glu Gly Tyr Val Val
            275                 280                 285
Lys Lys Ile Thr Met Cys Pro Gly Leu Tyr Gly Lys Thr Val Gly Tyr
            290                 295                 300
Ala Val Thr Tyr His Ala Glu Gly Phe Leu Val Cys Lys Thr Thr Asp
305                 310                 315                 320
Thr Val Lys Gly Glu Arg Val Ser Phe Pro Val Cys Thr Tyr Val Pro
                325                 330                 335
Ser Thr Ile Cys Asp Gln Met Thr Gly Ile Leu Ala Thr Asp Val Thr
            340                 345                 350
Pro Glu Asp Ala Gln Lys Leu Leu Val Gly Leu Asn Gln Arg Ile Val
            355                 360                 365
Val Asn Gly Arg Thr Gln Arg Asn Thr Asn Thr Met Lys Asn Tyr Leu
370                 375                 380
Leu Pro Ile Val Ala Val Ala Phe Ser Lys Trp Ala Arg Glu Tyr Lys
385                 390                 395                 400
Ala Asp Leu Asp Asp Glu Lys Pro Leu Gly Val Arg Glu Arg Ser Leu
                405                 410                 415
Thr Cys Cys Cys Leu Trp Ala Phe Lys Thr Arg Lys Met His Thr Met
                420                 425                 430
Tyr Lys Lys Pro Asp Thr Gln Thr Ile Val Lys Val Pro Ser Glu Phe
            435                 440                 445
Asn Ser Phe Val Ile Pro Ser Leu Trp Ser Thr Gly Leu Ala Ile Pro
            450                 455                 460
Val Arg Ser Arg Ile Lys Met Leu Leu Ala Lys Lys Thr Lys Arg Glu
465                 470                 475                 480
Leu Ile Pro Val Leu Asp Ala Ser Ser Ala Arg Asp Ala Glu Gln Glu
                485                 490                 495
```

```
Glu Lys Glu Arg Leu Glu Ala Glu Leu Thr Arg Glu Ala Leu Pro Pro
                500                 505                 510

Leu Val Pro Ile Ala Pro Ala Glu Thr Gly Val Val Asp Val Asp Val
            515                 520                 525

Glu Glu Leu Glu Tyr His Ala Gly Ala Gly Val Val Glu Thr Pro Arg
530                 535                 540

Ser Ala Leu Lys Val Thr Ala Gln Pro Asn Asp Val Leu Leu Gly Asn
545                 550                 555                 560

Tyr Val Val Leu Ser Pro Gln Thr Val Leu Lys Ser Ser Lys Leu Ala
                565                 570                 575

Pro Val His Pro Leu Ala Glu Gln Val Lys Ile Ile Thr His Asn Gly
            580                 585                 590

Arg Ala Gly Arg Tyr Gln Val Asp Gly Tyr Asp Gly Arg Val Leu Leu
        595                 600                 605

Pro Cys Gly Ser Ala Ile Pro Val Pro Glu Phe Gln Ala Leu Ser Glu
    610                 615                 620

Ser Ala Thr Met Val Tyr Asn Glu Arg Glu Phe Val Asn Arg Lys Leu
625                 630                 635                 640

Tyr His Ile Ala Val His Gly Pro Ser Leu Asn Thr Asp Glu Glu Asn
                645                 650                 655

Tyr Glu Lys Val Arg Ala Glu Arg Thr Asp Ala Glu Tyr Val Phe Asp
            660                 665                 670

Val Asp Lys Lys Cys Cys Val Lys Arg Glu Glu Ala Ser Gly Leu Val
        675                 680                 685

Leu Val Gly Glu Leu Thr Asn Pro Pro Phe His Glu Phe Ala Tyr Glu
    690                 695                 700

Gly Leu Lys Ile Arg Pro Ser Ala Pro Tyr Lys Thr Thr Val Val Gly
705                 710                 715                 720

Val Phe Gly Val Pro Gly Ser Gly Lys Ser Ala Ile Ile Lys Ser Leu
                725                 730                 735

Val Thr Lys His Asp Leu Val Thr Ser Gly Lys Lys Glu Asn Cys Gln
            740                 745                 750

Glu Ile Val Asn Asp Val Lys Lys His Arg Gly Leu Asp Ile Gln Ala
        755                 760                 765

Lys Thr Val Asp Ser Ile Leu Leu Asn Gly Cys Arg Arg Ala Val Asp
    770                 775                 780

Ile Leu Tyr Val Asp Glu Ala Phe Ala Cys His Ser Gly Thr Leu Leu
785                 790                 795                 800

Ala Leu Ile Ala Leu Val Lys Pro Arg Ser Lys Val Val Leu Cys Gly
                805                 810                 815

Asp Pro Lys Gln Cys Gly Phe Phe Asn Met Met Gln Leu Lys Val Asn
            820                 825                 830

Phe Asn His Asn Ile Cys Thr Glu Val Cys His Lys Ser Ile Ser Arg
        835                 840                 845

Arg Cys Thr Arg Pro Val Thr Ala Ile Val Ser Thr Leu His Tyr Gly
    850                 855                 860

Gly Lys Met Arg Thr Thr Asn Pro Cys Asn Lys Pro Ile Ile Ile Asp
865                 870                 875                 880

Thr Thr Gly Gln Thr Lys Pro Lys Pro Gly Asp Ile Val Leu Thr Cys
                885                 890                 895

Phe Arg Gly Trp Val Lys Gln Leu Gln Leu Asp Tyr Arg Gly His Glu
            900                 905                 910
```

```
Val Met Thr Ala Ala Ala Ser Gln Gly Leu Thr Arg Lys Gly Val Tyr
        915                 920                 925

Ala Val Arg Gln Lys Val Asn Glu Asn Pro Leu Tyr Ala Pro Ala Ser
930                 935                 940

Glu His Val Asn Val Leu Leu Thr Arg Thr Glu Asp Arg Leu Val Trp
945                 950                 955                 960

Lys Thr Leu Ala Gly Asp Pro Trp Ile Lys Val Leu Ser Asn Ile Pro
        965                 970                 975

Gln Gly Asn Phe Thr Ala Thr Leu Glu Glu Trp Gln Glu Glu His Asp
            980                 985                 990

Lys Ile Met Lys Val Ile Glu Gly Pro Ala Ala Pro Val Asp Ala Phe
        995                 1000                1005

Gln Asn Lys Ala Asn Val Cys Trp Ala Lys Ser Leu Val Pro Val
    1010                1015                1020

Leu Asp Thr Ala Gly Ile Arg Leu Thr Ala Glu Glu Trp Ser Thr
    1025                1030                1035

Ile Ile Thr Ala Phe Lys Glu Asp Arg Ala Tyr Ser Pro Val Val
    1040                1045                1050

Ala Leu Asn Glu Ile Cys Thr Lys Tyr Tyr Gly Val Asp Leu Asp
    1055                1060                1065

Ser Gly Leu Phe Ser Ala Pro Lys Val Ser Leu Tyr Tyr Glu Asn
    1070                1075                1080

Asn His Trp Asp Asn Arg Pro Gly Gly Arg Met Tyr Gly Phe Asn
    1085                1090                1095

Ala Ala Thr Ala Ala Arg Leu Glu Ala Arg His Thr Phe Leu Lys
    1100                1105                1110

Gly Gln Trp His Thr Gly Lys Gln Ala Val Ile Ala Glu Arg Lys
    1115                1120                1125

Ile Gln Pro Leu Ser Val Leu Asp Asn Val Ile Pro Ile Asn Arg
    1130                1135                1140

Arg Leu Pro His Ala Leu Val Ala Glu Tyr Lys Thr Val Lys Gly
    1145                1150                1155

Ser Arg Val Glu Trp Leu Val Asn Lys Val Arg Gly Tyr His Val
    1160                1165                1170

Leu Leu Val Ser Glu Tyr Asn Leu Ala Leu Pro Ala Ala Ala Val
    1175                1180                1185

Thr Trp Leu Ser Pro Leu Asn Val Thr Gly Ala Asp Arg Cys Tyr
    1190                1195                1200

Asp Leu Ser Leu Gly Leu Pro Ala Asp Ala Gly Arg Phe Asp Leu
    1205                1210                1215

Val Phe Val Asn Ile His Thr Glu Phe Arg Ile His His Tyr Gln
    1220                1225                1230

Gln Cys Val Asp His Ala Met Lys Leu Gln Met Leu Gly Gly Asp
    1235                1240                1245

Ala Leu Arg Leu Leu Lys Pro Gly Gly Ser Leu Leu Met Arg Ala
    1250                1255                1260

Tyr Gly Tyr Ala Asp Lys Ile Ser Glu Ala Val Val Ser Ser Leu
    1265                1270                1275

Ser Arg Lys Phe Ser Ser Ala Arg Val Leu Arg Pro Asp Cys Val
    1280                1285                1290

Thr Ser Asn Thr Glu Val Phe Leu Leu Phe Ser Asn Phe Asp Asn
    1295                1300                1305

Gly Lys Arg Pro Ser Thr Leu His Gln Met Asn Thr Lys Leu Ser
```

-continued

```
            1310                1315                1320

Ala Val Tyr Ala Gly Glu Ala Met His Thr Ala Gly Cys Ala Pro
    1325                1330                1335

Ser Tyr Arg Val Lys Arg Ala Asp Ile Ala Thr Cys Thr Glu Ala
    1340                1345                1350

Ala Val Val Asn Ala Ala Asn Ala Arg Gly Thr Val Gly Asp Gly
    1355                1360                1365

Val Cys Arg Ala Val Ala Lys Lys Trp Pro Ser Ala Phe Lys Gly
    1370                1375                1380

Glu Ala Thr Pro Val Gly Thr Ile Lys Thr Val Met Cys Gly Ser
    1385                1390                1395

Tyr Pro Val Ile His Ala Val Ala Pro Asn Phe Ser Ala Thr Thr
    1400                1405                1410

Glu Ala Glu Gly Asp Arg Glu Leu Ala Ala Val Tyr Arg Ala Val
    1415                1420                1425

Ala Ala Glu Val Asn Arg Leu Ser Leu Ser Ser Val Ala Ile Pro
    1430                1435                1440

Leu Leu Ser Thr Gly Val Phe Ser Gly Gly Arg Asp Arg Leu Gln
    1445                1450                1455

Gln Ser Leu Asn His Leu Phe Thr Ala Met Asp Ala Thr Asp Ala
    1460                1465                1470

Asp Val Thr Ile Tyr Cys Arg Asp Lys Ser Trp Glu Lys Lys Ile
    1475                1480                1485

Gln Glu Ala Ile Asp Met Arg Thr Ala Val Glu Leu Leu Asn Asp
    1490                1495                1500

Asp Val Glu Leu Thr Thr Asp Leu Val Arg Val His Pro Asp Ser
    1505                1510                1515

Ser Leu Val Gly Arg Lys Gly Tyr Ser Thr Thr Asp Gly Ser Leu
    1520                1525                1530

Tyr Ser Tyr Phe Glu Gly Thr Lys Phe Asn Gln Ala Ala Ile Asp
    1535                1540                1545

Met Ala Glu Ile Leu Thr Leu Trp Pro Arg Leu Gln Glu Ala Asn
    1550                1555                1560

Glu Gln Ile Cys Leu Tyr Ala Leu Gly Glu Thr Met Asp Asn Ile
    1565                1570                1575

Arg Ser Lys Cys Pro Val Asn Asp Ser Asp Ser Ser Thr Pro Pro
    1580                1585                1590

Arg Thr Val Pro Cys Leu Cys Arg Tyr Ala Met Thr Ala Glu Arg
    1595                1600                1605

Ile Ala Arg Leu Arg Ser His Gln Val Lys Ser Met Val Val Cys
    1610                1615                1620

Ser Ser Phe Pro Leu Pro Lys Tyr His Val Asp Gly Val Gln Lys
    1625                1630                1635

Val Lys Cys Glu Lys Val Leu Leu Phe Asp Pro Thr Val Pro Ser
    1640                1645                1650

Val Val Ser Pro Arg Lys Tyr Ala Ala Ser Thr Thr Asp His Ser
    1655                1660                1665

Asp Arg Ser Leu Arg Gly Phe Asp Leu Asp Trp Thr Thr Asp Ser
    1670                1675                1680

Ser Ser Thr Ala Ser Asp Thr Met Ser Leu Pro Ser Leu Gln Ser
    1685                1690                1695

Cys Asp Ile Asp Ser Ile Tyr Glu Pro Met Ala Pro Ile Val Val
    1700                1705                1710
```

```
Thr Ala Asp Val His Pro Glu Pro Ala Gly Ile Ala Asp Leu Ala
1715                1720                1725

Ala Asp Val His Pro Glu Pro Ala Asp His Val Asp Leu Glu Asn
    1730                1735                1740

Pro Ile Pro Pro Pro Arg Pro Lys Arg Ala Ala Tyr Leu Ala Ser
1745                1750                1755

Arg Ala Ala Glu Arg Pro Val Pro Ala Pro Arg Lys Pro Thr Pro
    1760                1765                1770

Ala Pro Arg Thr Ala Phe Arg Asn Lys Leu Pro Leu Thr Phe Gly
1775                1780                1785

Asp Phe Asp Glu His Glu Val Asp Ala Leu Ala Ser Gly Ile Thr
    1790                1795                1800

Phe Gly Asp Phe Asp Asp Val Leu Arg Leu Gly Arg Ala Gly Ala
1805                1810                1815

Tyr Ile Phe Ser Ser Asp Thr Gly Ser Gly His Leu Gln Gln Lys
1820                1825                1830

Ser Val Arg Gln His Asn Leu Gln Cys Ala Gln Leu Asp Ala Val
1835                1840                1845

Glu Glu Glu Lys Met Tyr Pro Pro Lys Leu Asp Thr Glu Arg Glu
1850                1855                1860

Lys Leu Leu Leu Leu Lys Met Gln Met His Pro Ser Glu Ala Asn
1865                1870                1875

Lys Ser Arg Tyr Gln Ser Arg Lys Val Glu Asn Met Lys Ala Thr
1880                1885                1890

Val Val Asp Arg Leu Thr Ser Gly Ala Arg Leu Tyr Thr Gly Ala
1895                1900                1905

Asp Val Gly Arg Ile Pro Thr Tyr Ala Val Arg Tyr Pro Arg Pro
1910                1915                1920

Val Tyr Ser Pro Thr Val Ile Glu Arg Phe Ser Ser Pro Asp Val
1925                1930                1935

Ala Ile Ala Ala Cys Asn Glu Tyr Leu Ser Arg Asn Tyr Pro Thr
1940                1945                1950

Val Ala Ser Tyr Gln Ile Thr Asp Glu Tyr Asp Ala Tyr Leu Asp
1955                1960                1965

Met Val Asp Gly Ser Asp Ser Cys Leu Asp Arg Ala Thr Phe Cys
1970                1975                1980

Pro Ala Lys Leu Arg Cys Tyr Pro Lys His His Ala Tyr His Gln
1985                1990                1995

Pro Thr Val Arg Ser Ala Val Pro Ser Pro Phe Gln Asn Thr Leu
2000                2005                2010

Gln Asn Val Leu Ala Ala Ala Thr Lys Arg Asn Cys Asn Val Thr
2015                2020                2025

Gln Met Arg Glu Leu Pro Thr Met Asp Ser Ala Val Phe Asn Val
2030                2035                2040

Glu Cys Phe Lys Arg Tyr Ala Cys Ser Gly Glu Tyr Trp Glu Glu
2045                2050                2055

Tyr Ala Lys Gln Pro Ile Arg Ile Thr Thr Glu Asn Ile Thr Thr
2060                2065                2070

Tyr Val Thr Lys Leu Lys Gly Pro Lys Ala Ala Ala Leu Phe Ala
2075                2080                2085

Lys Thr His Asn Leu Val Pro Leu Gln Glu Val Pro Met Asp Arg
2090                2095                2100
```

| | | | | | | | | | | |
|---|---|---|---|---|---|---|---|---|---|---|
| Phe | Thr | Val | Asp | Met | Lys | Arg | Asp | Val | Lys | Val | Thr | Pro | Gly | Thr |
| | 2105 | | | | 2110 | | | | 2115 | |
| Lys | His | Thr | Glu | Glu | Arg | Pro | Lys | Val | Gln | Val | Ile | Gln | Ala | Ala |
| | 2120 | | | | 2125 | | | | 2130 | |
| Glu | Pro | Leu | Ala | Thr | Ala | Tyr | Leu | Cys | Gly | Ile | His | Arg | Glu | Leu |
| | 2135 | | | | 2140 | | | | 2145 | |
| Val | Arg | Arg | Leu | Asn | Ala | Val | Leu | Arg | Pro | Asn | Val | His | Thr | Leu |
| | 2150 | | | | 2155 | | | | 2160 | |
| Phe | Asp | Met | Ser | Ala | Glu | Asp | Phe | Asp | Ala | Ile | Ile | Ala | Ser | His |
| | 2165 | | | | 2170 | | | | 2175 | |
| Phe | His | Pro | Gly | Asp | Pro | Val | Leu | Glu | Thr | Asp | Ile | Ala | Ser | Phe |
| | 2180 | | | | 2185 | | | | 2190 | |
| Asp | Lys | Ser | Gln | Asp | Asp | Ser | Leu | Ala | Leu | Thr | Gly | Leu | Met | Ile |
| | 2195 | | | | 2200 | | | | 2205 | |
| Leu | Glu | Asp | Leu | Gly | Val | Asp | Gln | Tyr | Leu | Leu | Asp | Leu | Ile | Glu |
| | 2210 | | | | 2215 | | | | 2220 | |
| Ala | Ala | Phe | Gly | Glu | Ile | Ser | Ser | Cys | His | Leu | Pro | Thr | Gly | Thr |
| | 2225 | | | | 2230 | | | | 2235 | |
| Arg | Phe | Lys | Phe | Gly | Ala | Met | Met | Lys | Ser | Gly | Met | Phe | Leu | Thr |
| | 2240 | | | | 2245 | | | | 2250 | |
| Leu | Phe | Ile | Asn | Thr | Val | Leu | Asn | Ile | Thr | Ile | Ala | Ser | Arg | Val |
| | 2255 | | | | 2260 | | | | 2265 | |
| Leu | Glu | Gln | Arg | Leu | Thr | Asp | Ser | Ala | Cys | Ala | Ala | Phe | Ile | Gly |
| | 2270 | | | | 2275 | | | | 2280 | |
| Asp | Asp | Asn | Ile | Val | His | Gly | Val | Ile | Ser | Asp | Lys | Leu | Met | Ala |
| | 2285 | | | | 2290 | | | | 2295 | |
| Glu | Arg | Cys | Ala | Ser | Trp | Val | Asn | Met | Glu | Val | Lys | Ile | Ile | Asp |
| | 2300 | | | | 2305 | | | | 2310 | |
| Ala | Val | Met | Gly | Glu | Lys | Pro | Pro | Tyr | Phe | Cys | Gly | Gly | Phe | Ile |
| | 2315 | | | | 2320 | | | | 2325 | |
| Val | Phe | Asp | Ser | Val | Thr | Gln | Thr | Ala | Cys | Arg | Val | Ser | Asp | Pro |
| | 2330 | | | | 2335 | | | | 2340 | |
| Leu | Lys | Arg | Leu | Phe | Lys | Leu | Gly | Lys | Pro | Leu | Thr | Ala | Glu | Asp |
| | 2345 | | | | 2350 | | | | 2355 | |
| Lys | Gln | Asp | Glu | Asp | Arg | Arg | Ala | Leu | Ser | Asp | Glu | Val | Ser |
| | 2360 | | | | 2365 | | | | 2370 | |
| Lys | Trp | Phe | Arg | Thr | Gly | Leu | Gly | Ala | Glu | Leu | Glu | Val | Ala | Leu |
| | 2375 | | | | 2380 | | | | 2385 | |
| Thr | Ser | Arg | Tyr | Glu | Val | Glu | Gly | Cys | Lys | Ser | Ile | Leu | Ile | Ala |
| | 2390 | | | | 2395 | | | | 2400 | |
| Met | Ala | Thr | Leu | Ala | Arg | Asp | Ile | Lys | Ala | Phe | Lys | Lys | Leu | Arg |
| | 2405 | | | | 2410 | | | | 2415 | |
| Gly | Pro | Val | Ile | His | Leu | Tyr | Gly | Gly | Pro | Arg | Leu | Val | Arg |
| | 2420 | | | | 2425 | | | | 2430 | |

<210> SEQ ID NO 4
<211> LENGTH: 7872
<212> TYPE: DNA
<213> ORGANISM: Artificial
<220> FEATURE:
<223> OTHER INFORMATION: Nucleic acid sequence of resynthesized sequence
    of SFV replicase with inserted heterologous intron which when
    expressed correspond to SEQ ID NO:1

<400> SEQUENCE: 4
atggccgcca aggtgcacgt ggacatcgag gccgacagcc ccttcatcaa gagcctgcag     60

```
aaggccttcc ccagcttcga ggtggagtcc ctgcaggtga cccccaacga ccacgccaac      120
gccagggcct tcagccacct ggccaccaag ctgatcgagc aggaaaccga caaggacacc      180
ctgatcctgg acatcggcag cgcccccctca aggtgagttt ggggacccct gattgttctt     240 tcttttcgc tattgtaaaa ttcatgttat atggagggg caaagttttc agggtgttgt        300
ttagaatggg aagatgtccc ttgtatcact atggaccctc atgataattt tgtttctttc      360
actttctact ctgttgacaa ccattgtctc ctcttatttt cttttcattt tctgtaactt      420
tttcgttaaa ctttagcttg catttgtaac gaatttttaa attcacttt gtttatttgt       480 cagattgtaa gtactttctc taatcacttt tttttcaagg caatcagggt atattatatt      540
gtacttcagc acagttttag agaacaattg ttataattaa atgataaggt agaatatttc      600
tgcatataaa ttctggctgg cgtggaaata ttcttattgg tagaaacaac tacaccctgg      660
tcatcatcct gcctttctct ttatggttac aatgatatac actgtttgag atgaggataa      720
aatactctga gtccaaaccg ggcccctctg ctaaccatgt tcatgccttc ttcttttcc       780 tacaggcgga tgatgagcac ccacaagtac cactgcgtgt gccccatgcg gagcgccgag      840
gaccccgagc ggctggtgtg ctacgccaag aagctggccg ccgccagcgg caaggtgctg      900
gaccgggaga tcgccggcaa gatcaccgac ctgcagaccg tgatggccac ccccgacgcc      960
gagagcccca ccttctgcct gcacaccgac gtgacctgcc ggacagccgc cgaggtggcc     1020
gtgtaccagg acgtgtacgc cgtgcacgcc cccacctccc tgtaccacca ggccatgaag     1080
ggcgtgcgga ccgcctactg gatcggcttc gacaccaccc ccttcatgtt cgacgccctg     1140
gccggagcct accccaccta cgccaccaac tgggccgacg agcaggtgct gcaggccgg      1200 aacatcggcc tgtgcgccgc cagcctgacc gagggccggc tggcaagct gtccatcctg      1260 cggaagaagc agctgaagcc ctgcgacacc gtgatgttca gcgtgggcag cacactgtac     1320
accgagagcc ggaagctgct gcggagctgg cacctgccca gcgtgttcca cctgaagggc     1380
aagcagagct tcacctgcag atgcgacacc atcgtgagct gcagggcta cgtggtgaag      1440 aaaatcacca tgtgccctgg cctgtacggc aagaccgtgg gctacgccgt gacctaccac     1500
gccgagggct ttctggtgtg caagaccacc gataccgtga agggcgagag agtgagcttc     1560
cccgtctgca cctacgtgcc cagcaccatc tgcgaccaga tgaccggtat cctggccacc     1620
gatgtgaccc ccgaggacgc ccagaaactg ctggtcggcc tgaaccagcg gatcgtggtg     1680
aacggccgga cccagcggaa caccaacacc atgaagaact acctgctgcc catcgtggcc     1740
gtggccttca gcaagtgggc cagagagtac aaggccgacc tggacgacga aagcccctg      1800 ggcgtgcggg agcggagcct gacctgctgc tgcctgtggg ccttcaagac ccggaagatg     1860
cacaccatgt acaagaagcc cgacacccag accatcgtga aggtgcccag cgagttcaac     1920
agcttcgtga tccccagcct gtggagcacc ggcctggcca tccccgtgcg agccggatc      1980 aagatgctgc tggccaagaa aaccaagcgg gagctgatcc ccgtgctgga cgccagcagc     2040
gccagggacg ccgagcagga agagaaagag cggctggaag ccgagctgac ccgggaggcc     2100
ctgccccccc tggtgcctat cgccctgcc gagaccggcg tggtggacgt ggatgtggag      2160
gaactggaat accacgccgg agccggggtg gtggagaccc ccagatccgc cctgaaggtg     2220
acagcccagc ccaacgacgt gctgctgggc aactacgtgg tgctgtcccc ccagaccgtg     2280
ctgaagagca gcaagctggc ccccgtgcac cctctggccg agcaggtgaa gatcatcacc     2340
cacaacggca gggccggcag ataccaggtc gacggctacg acggccgggt gctgctgcca     2400
```

-continued

```
tgcggctccg ccatccctgt gcccgagttc caggccctga gcgagagcgc cacaatggtg    2460
tacaacgagc gggagttcgt gaaccggaag ctgtaccaca ttgccgtgca cggccctagc    2520
ctgaacaccg atgaggaaaa ctacgagaaa gtgcgggccg agcggaccga tgccgagtac    2580
gtgttcgacg tggacaagaa atgctgcgtg aagcgggagg aagccagcgg gctggtgctg    2640
gtcggggagc tgaccaaccc cccttccac gagttcgcct acgagggcct gaagatccgg    2700
ccctccgccc cctacaagac cacagtggtg ggcgtgttcg gcgtgcccgg cagcggcaag    2760
agcgccatca tcaagtccct ggtgaccaag cacgacctgg tgacctccgg caagaaagag    2820
aactgccagg aaatcgtcaa cgacgtcaag aagcaccggg gcctggacat ccaggccaag    2880
acagtggaca gcatcctgct gaacggctgc agacgggccg tggatatcct gtacgtggac    2940
gaggccttcg cctgccacag cggcaccctg ctggccctga tcgccctggt gaagccccgg    3000
tccaaggtgg tgctgtgcgg cgaccccaag cagtgcggct tcttcaacat gatgcagctg    3060
aaggtgaact tcaaccacaa catctgcacc gaagtgtgcc acaagagcat cagccggcgg    3120
tgcaccagac ccgtgaccgc catcgtgtcc accctgcact acgcggcaa gatgcggacc    3180 accaacccct gcaacaagcc catcatcatc gataccaccg ccagaccaa gcccaagccc    3240 ggcgacatcg tgctgacctg cttccgcggc tgggtgaagc agctgcagct ggactaccgg    3300
ggccacgagg tgatgaccgc cgccgcctcc cagggcctga ccagaaaggg cgtgtatgcc    3360
gtgcggcaga aggtgaacga gaacccctg tacgcccctg ccagcgagca cgtgaatgtg    3420
ctgctgaccc ggaccgagga caggctggtg tggaaaaccc tggccggcga ccctggatc    3480 aaggtgctgt ccaacatccc ccagggcaac ttcaccgcca ccctggaaga gtggcaggaa    3540
gagcacgaca agatcatgaa ggtgatcgag ggccctgccg ccccagtgga cgccttccag    3600
aacaaggcca acgtgtgctg ggccaagagc ctggtgcctg tgctggacac cgccggcatc    3660
cggctgaccg ccgaagagtg gagcaccatc atcaccgcct tcaaagagga ccgggcctac    3720
agccccgtgg tggccctgaa cgagatctgc accaagtact acggcgtgga cctggacagc    3780
ggcctgttca gcgcccccaa ggtgtccctg tactacgaga caaccactg gacaaccgg    3840 ccaggcggca ggatgtacgg cttcaacgcc gccaccgccg ccagactgga agcccggcac    3900
accttcctga agggccagtg gcacaccggc aagcaggccg tgatcgccga gagaaagatc    3960
cagcccctgt ccgtgctgga taacgtgatc cctatcaacc ggcggctgcc ccacgccctg    4020
gtggccgagt acaagacagt gaagggcagc cgggtggagt ggctggtgaa caaagtgcgg    4080
ggctaccacg tgctgctggt gtctgagtac aacctggccc tgcctcggcg gagggtgacc    4140
tggctgtccc ctctgaacgt gacaggcgcc gacaggtgct acgacctgag cctgggcctg    4200
cctgccgacg ccggcagatt cgacctggtg ttcgtgaaca tccacaccga gttcagaatc    4260
caccactacc agcagtgcgt ggaccacgcc atgaagctgc agatgctggg cggcgacgcc    4320
ctgaggctgc tgaagcctgg cggcagcctg ctgatgcggg cctacggcta cgccgacaag    4380
atctccgagg ccgtggtgtc cagcctgagc cggaagttca gctccgccag ggtgctgaga    4440
cccgactgcg tgaccagcaa cacagaagtg tttctgctgt cagcaacttc gacaacggc    4500 aagcggccca gcaccctgca ccagatgaac accaagctgt ccgccgtgta cgccggcgag    4560
gccatgcaca ccgccggatg cgcccccagc tacgggtga agcgggccga catcgccacc    4620
tgcaccgagg ccgccgtggt gaatgccgcc aatgccaggg gcaccgtggg cgacggcgtg    4680
tgcagggccg tggccaaaaa gtggcccagc gccttcaagg gcgaggccac ccctgtgggc    4740
accatcaaaa ccgtgatgtg cggcagctac cccgtgatcc acgccgtggc ccccaatttc    4800
```

-continued

```
agcgccacca cagaggccga gggcgaccgg gaactggccg ccgtgtatag agccgtggcc    4860
gccgaagtga acagactgag cctgagcagc gtggccatcc ctctgctgtc caccggcgtg    4920
ttcagcggcg gcagggaccg gctgcagcag agcctgaacc acctgttcac cgctatggac    4980
gccaccgacc ccgacgtgac aatctactgc cgggacaaga gctgggagaa gaagatccag    5040
gaagccatcg acatgaggac cgccgtggag ctgctgaacg acgacgtgga gctgacaacc    5100
gacctggtgc gcgtgcaccc cgacagcagc ctggtgggcc ggaagggcta cagcaccacc    5160
gacggctccc tgtacagcta cttcgagggc accaagttca accaggccgc catcgatatg    5220
gccgagatcc tgaccctgtg gcccaggctg caggaagcca acgagcagat ctgtctgtac    5280
gccctgggcg agacaatgga caacatccgg tccaagtgcc ccgtgaacga cagcgacagc    5340 agcaccccc ctcggaccgt gccctgcctg tgcagatacg ccatgaccgc cgagcggatc    5400
gcccggctgc ggagccacca ggtgaagagc atggtggtgt gcagcagctt cccctgccc    5460 aagtaccacg tggatggcgt gcagaaagtg aagtgcgaga aggtgctgct gttcgacccc    5520
accgtgccta gcgtggtgtc cccccggaag tacgccgcct ccaccaccga ccacagcgac    5580
agaagcctgc ggggcttcga cctggactgg accaccgact ccagcagcac cgccagcgac    5640
accatgagcc tgcccagcct gcagagctgc gacatcgaca gcatctacga gcctatggcc    5700
cccatcgtgg tgaccgccga cgtgcaccct gagccagccg catcgccga cctggccgcc    5760 gatgtgcacc cagaacccgc cgaccacgtg gatctggaaa accccatccc ccctcccaga    5820
cccaagaggg ccgcctacct ggccagcaga gccgccgaga ggcccgtgcc tgcccccaga    5880
aagcccaccc cagccccag aaccgccttc aggaacaagc tgcccctgac cttcggcgac    5940
ttcgacgagc acgaggtgga cgccctggcc agcggcatca ccttcggcga ttttgatgac    6000
gtgctgcggc tgggcagagc cggagcctat atcttcagca gcgacaccgg ctccggccac    6060
ctgcagcaga aaagcgtgag acagcacaac ctgcagtgcg cccagctgga cgccgtggaa    6120
gaggaaaaga tgtacccccc caagctggat accgagcggg aaaagctgct gctgctgaaa    6180
atgcagatgc cccccagcga ggccaacaag agccgctacc agtctaggaa ggtggagaac    6240
atgaaggcca ccgtggtgga ccggctgacc agcgcgcca ggctgtacac aggggccgac    6300
gtgggcagaa tccctaccta cgccgtgcgc taccccaggc ccgtgtacag ccccaccgtg    6360
atcgagcggt tcagcagccc cgacgtggcc atcgccgcct gcaatgagta cctgtctagg    6420
aactacccaa ccgtggccag ctaccagatc accgatgagt acgatgccta cctggacatg    6480
gtggacggca gcgacagctg cctggaccgg gccaccttct gtcccgccaa gctgcggtgc    6540
taccccaagc accacgccta tcaccagccc accgtgagaa gcgccgtgcc cagcccttc    6600 cagaataccc tgcagaatgt gctggccgcc gccaccaagc ggaactgcaa cgtgacccag    6660
atgagagaac tgcccacaat ggacagcgcc gtgtttaacg tggagtgctt caagagatac    6720
gcctgcagcg gcgagtactg ggaggaatac gccaagcagc ccatccggat caccaccgag    6780
aacatcacca cctacgtgac caagctgaag gccccaagg ccgccgccct gttcgccaag    6840
acccacaacc tggtgcccct gcaggaagtg cctatggaca ggttcaccgt ggacatgaag    6900
cgggacgtga aggtgacccc tggcaccaag cacaccgagg aacggcccaa ggtgcaggtg    6960
atccaggccg ccgagcctct ggccaccgcc tatctgtgcg gcatccaccg ggagctggtg    7020
cggcggctga acgccgtgct gaggcccaac gtgcacaccc tgttcgacat gtccgccgag    7080
gacttcgacg ccatcatcgc cagccacttc caccccggcg acccagtgct ggaaaccgat    7140
```

| | |
|---|---:|
| atcgccagct tcgacaagag ccaggacgac agcctggccc tgaccggcct gatgatcctg | 7200 |
| gaagatctgg gcgtggacca gtacctgctg gatctgatcg aggccgcctt cggcgagatc | 7260 |
| agcagctgcc acctgcctac cggcacccgg ttcaagttcg gcgccatgat gaagagcggc | 7320 |
| atgtttctga ccctgttcat caacacagtg ctgaatatca ccatcgccag cagggtgctg | 7380 |
| gaacagcggc tgaccgacag cgcctgcgcc gccttcatcg gcgacgacaa catcgtgcac | 7440 |
| ggcgtgatca gcgacaagct gatggccgag cggtgcgcca gctgggtgaa catgaagtg | 7500 |
| aagattatcg acgccgtgat gggcgaaaag ccccccctact tctgcggcgg cttcatcgtg | 7560 |
| ttcgacagcg tgacacagac cgcctgcaga gtgagcgacc ccctgaagcg gctgttcaag | 7620 |
| ctgggcaaac tctgacagc cgaggacaag caggacgagg accggcggag ggccctgtcc | 7680 |
| gacgaggtgt ccaagtggtt ccggaccggc tgggcgccg agctggaagt ggccctgaca | 7740 |
| agccgctacg aggtggaggg ctgcaagagc atcctgatcg ctatggccac cctggcccgg | 7800 |
| gacatcaagg cctttaagaa gctgagaggc cctgtcatcc acctgtacgg cggaccccgg | 7860 |
| ctggtgcggt ga | 7872 |

<210> SEQ ID NO 5
<211> LENGTH: 10342
<212> TYPE: DNA
<213> ORGANISM: Artificial
<220> FEATURE:
<223> OTHER INFORMATION: Plasmid pRSV-Nsp1234

<400> SEQUENCE: 5

| | |
|---|---:|
| cacagcccag cttggagcga acgacctaca ccgaactgag atacctacag cgtgagctat | 60 |
| gagaaagcgc cacgcttccc gaagggagaa aggcggacag gtatccggta agcggcaggg | 120 |
| tcggaacagg agagcgcacg agggagcttc caggggggaaa cgcctggtat ctttatagtc | 180 |
| ctgtcgggtt tcgccaccte tgacttgagc gtcgattttt gtgatgctcg tcaggggggc | 240 |
| ggagcctatg gaaaaacgcc agcaacgcat cgataaaata aaagattta tttagtctcc | 300 |
| agaaaaaggg gggaatgaaa gaccccacct gtaggtttgg caagctagcg tataccctcg | 360 |
| acctgcaggt cgatcgactc tagtatggtg cactctcagt acaatctgct ctgatgccgc | 420 |
| atagttaagc cagtatctgc tccctgcttg tgtgttggag gtcgctgagt agtgcgcgag | 480 |
| caaaatttaa gctacaacaa ggcaaggctt gaccgacaat tgcatgaaga atctgcttag | 540 |
| ggttaggcgt tttgcgctgc ttcgcgatgt acgggccaga tatacgcgta tctgagggga | 600 |
| ctagggtgtg tttaggcgaa agcggggct tcggttgtac gcggttagga gtcccctcag | 660 |
| gatatagtag tttcgctttt gcatagggag ggggaaatgt agtcttatgc aatactcttg | 720 |
| tagtcttgca acatggtaac gatgagttag caacatgcct tacaaggaga gaaaaagcac | 780 |
| cgtgcatgcc gattggtgga agtaaggtgg tacgatcgtg ccttattagg aaggcaacag | 840 |
| acgggtctga catggattgg acgaaccact gaattccgca ttgcagagat attgtattta | 900 |
| agtgcctagc tcgatacaat aaacgccatt tgaccattca ccacattggt gtgcacctcc | 960 |
| aagctggtag aggatcggtc gatcgactct agacgccacc atggccgcca aggtgcacgt | 1020 |
| ggacatcgag gccgacagcc ccttcatcaa gagcctgcag aaggccttcc ccagcttcga | 1080 |
| ggtggagtcc ctgcaggtga ccccccaacga ccacgccaac gccagggcct tcagccacct | 1140 |
| ggccaccaag ctgatcgagc aggaaaaccga caaggacacc ctgatcctgg acatcggcag | 1200 |
| cgccccctca aggtgagttt ggggaccctt gattgttctt tctttttcgc tattgtaaaa | 1260 |
| ttcatgttat atggaggggg caaagttttc agggtgttgt ttagaatggg aagatgtccc | 1320 |

```
ttgtatcact atggaccctc atgataattt tgtttctttc actttctact ctgttgacaa   1380
ccattgtctc ctcttatttt cttttcattt tctgtaactt tttcgttaaa ctttagcttg   1440
catttgtaac gaattttaa attcacttt gtttatttgt cagattgtaa gtactttctc   1500
taatcactt tttttcaagg caatcagggt atattatatt gtacttcagc acagttttag   1560
agaacaattg ttataattaa atgataaggt agaatatttc tgcatataaa ttctggctgg   1620
cgtggaaata ttcttattgg tagaaacaac tacaccctgg tcatcatcct gcctttctct   1680
ttatggttac aatgatatac actgtttgag atgaggataa aatactctga gtccaaaccg   1740
ggcccctctg ctaaccatgt tcatgccttc ttcttttttcc tacaggcgga tgatgagcac   1800
ccacaagtac cactgcgtgt gccccatgcg gagcgccgag gaccccgagc ggctggtgtg   1860
ctacgccaag aagctggccg ccgccagcgg caaggtgctg gaccgggaga tcgccggcaa   1920
gatcaccgac ctgcagaccg tgatggccac ccccgacgcc gagagcccca ccttctgcct   1980
gcacaccgac gtgacctgcc ggacagccgc cgaggtggcc gtgtaccagg acgtgtacgc   2040
cgtgcacgcc cccacctccc tgtaccacca ggccatgaag ggcgtgcgga ccgcctactg   2100
gatcggcttc gacaccaccc ccttcatgtt cgacgccctg gccggagcct accccaccta   2160
cgccaccaac tgggccgacg agcaggtgct gcaggcccgg aacatcggcc tgtgcgccgc   2220
cagcctgacc gagggccggc tgggcaagct gtccatcctg cggaagaagc agctgaagcc   2280
ctgcgacacc gtgatgttca gcgtgggcag cacactgtac accgagagcc ggaagctgct   2340
gcggagctgg cacctgccca gcgtgttcca cctgaagggc aagcagagct tcacctgcag   2400
atgcgacacc atcgtgagct gcgagggcta cgtggtgaag aaaatcacca tgtgccctgg   2460
cctgtacggc aagaccgtgg gctacgccgt gacctaccac gccgagggct ttctggtgtg   2520
caagaccacc gataccgtga agggcgagag agtgagcttc cccgtctgca cctacgtgcc   2580
cagcaccatc tgcgaccaga tgaccggtat cctggccacc gatgtgaccc ccgaggacgc   2640
ccagaaactg ctggtcggcc tgaaccagcg gatcgtggtg aacggccgga cccagcggaa   2700
caccaacacc atgaagaact acctgctgcc catcgtggcc gtggccttca gcaagtgggc   2760
cagagagtac aaggccgacc tggacgacga gaagcccctg ggcgtgcggg agcggagcct   2820
gacctgctgc tgcctgtggg ccttcaagac ccggaagatg cacaccatgt acaagaagcc   2880
cgacacccag accatcgtga aggtgcccag cgagttcaac agcttcgtga tccccagcct   2940
gtggagcacc ggcctggcca tccccgtgcg gagccggatc aagatgctgc tggccaagaa   3000
aaccaagcgg gagctgatcc ccgtgctgga cgccagcagc gccagggacg ccgagcagga   3060
agagaaagag cggctggaag ccgagctgac ccgggaggcc ctgcccccc tggtgcctat   3120
cgcccctgcc gagaccggcg tggtggacgt ggatgtggag gaactggaat accacgccgg   3180
agccggggtg gtggagaccc ccagatccgc cctgaaggtg acagcccagc caacgacgt   3240
gctgctggga aactacgtgg tgctgtcccc ccagaccgtg ctgaagagca gcaagctggc   3300
ccccgtgcac cctctggccg agcaggtgaa gatcatcacc cacaacggca gggccggcag   3360
ataccaggtc gacggctacg acggccgggt gctgctgcca tgcggctccg ccatccctgt   3420
gcccgagttc caggccctga gcgagagcgc cacaatggta tacaacgagc gggagttcgt   3480
gaaccggaag ctgtaccaca ttgccgtgca cggccctagc ctgaacaccg atgaggaaaa   3540
ctacgagaaa gtgcgggccg agcggaccga tgccgagtac gtgttcgacg tggacaagaa   3600
atgctgcgtg aagcgggagg aagccagcgg gctggtgctg gtcggggagc tgaccaaccc   3660
```

```
cccttccac gagttcgcct acgagggcct gaagatccgg ccctccgccc cctacaagac    3720
cacagtggtg ggcgtgttcg gcgtgccgg cagcggcaag agcgccatca tcaagtccct    3780
ggtgaccaag cacgacctgg tgacctccgg caagaaagag aactgccagg aaatcgtcaa    3840
cgacgtcaag aagcaccggg gcctggacat ccaggccaag acagtggaca gcatcctgct    3900
gaacggctgc agacgggccg tggatatcct gtacgtggac gaggccttcg cctgccacag    3960
cggcaccctg ctggccctga tcgccctggt gaagccccgg tccaaggtgg tgctgtgcgg    4020
cgaccccaag cagtgcggct tcttcaacat gatgcagctg aaggtgaact tcaaccacaa    4080
catctgcacc gaagtgtgcc acaagagcat cagccggcgg tgcaccagac ccgtgaccgc    4140
catcgtgtcc accctgcact acggcggcaa gatgcggacc accaacccct gcaacaagcc    4200
catcatcatc gataccaccg ccagaccaa gcccaagccc ggcgacatcg tgctgacctg    4260
cttccgcggc tgggtgaagc agctgcagct ggactaccgg ggccacgagg tgatgaccgc    4320
cgccgcctcc cagggcctga ccagaaaggg cgtgtatgcc gtgcggcaga aggtgaacga    4380 gaacccctg tacgccctg ccagcgagca cgtgaatgtg ctgctgaccc ggaccgagga    4440
caggctggtg tggaaaaccc tggccggcga ccctggatc aaggtgctgt ccaacatccc    4500
ccagggcaac ttcaccgcca ccctggaaga gtggcaggaa gagcacgaca agatcatgaa    4560
ggtgatcgag ggccctgccg ccccagtgga cgccttccag aacaaggcca acgtgtgctg    4620
ggccaagagc ctggtgcctg tgctggacac cgccggcatc cggctgaccg ccgaagagtg    4680
gagcaccatc atcaccgcct caaagagga ccgggcctac agcccgtgg tggccctgaa    4740 cgagatctgc accaagtact acggcgtgga cctggacagc ggcctgttca cgcccccaa    4800 ggtgtccctg tactacgaga caaccactg gacaaccgg ccaggcggca ggatgtacgg    4860
cttcaacgcc gccaccgccg ccagactgga agcccgcac accttctga agggccagtg    4920 gcacaccggc aagcaggccg tgatcgccga gagaaagatc cagcccctgt ccgtgctgga    4980
taacgtgatc cctatcaacc ggcggctgcc ccacgccctg gtggccgagt acaagacagt    5040
gaagggcagc cgggtggagt ggctggtgaa caaagtgcgg ggctaccacg tgctgctggt    5100
gtctgagtac aacctggccc tgcctcggcg gaggtgacc tggctgtccc ctctgaacgt    5160
gacaggcgcc gacaggtgct acgacctgag cctgggcctg cctgccgacg ccggcagatt    5220
cgacctggtg ttcgtgaaca tccacaccga gttcagaatc caccactacc agcagtgcgt    5280
ggaccacgcc atgaagctgc agatgctggg cggcgacgcc ctgaggctgc tgaagcctgg    5340
cggcagcctg ctgatgcggg cctacggcta cgccgacaag atctccgagg ccgtggtgtc    5400
cagcctgagc cggaagttca gctccgccag ggtgctgaga cccgactgcg tgaccagcaa    5460
cacagaagtg tttctgctgt tcagcaactt cgacaacggc aagcggccca gcaccctgca    5520
ccagatgaac accaagctgt ccgccgtgta cgccggcgag gccatgcaca ccgccggatg    5580 cgccccagc taccgggtga agcgggccga catcgccacc tgcaccgagg ccgccgtggt    5640
gaatgccgcc aatgccaggg gcaccgtggg cgacggcgtg tgcagggccg tggccaaaaa    5700
gtggcccagc gccttcaagg gcgaggccac ccctgtgggc accatcaaaa ccgtgatgtg    5760
cggcagctac cccgtgatcc acgccgtggc ccccaatttc agcgccacca cagaggccga    5820
gggcgaccgg gaactggccg ccgtgtatag agccgtggcc gccgaagtga acagactgag    5880
cctgagcagc gtggccatcc ctctgctgtc caccggcgtg ttcagcggcg gcagggaccg    5940
gctgcagcag agcctgaacc acctgttcac cgctatggac gccaccgacg ccgacgtgac    6000
aatctactgc cgggacaaga gctgggagaa gaagatccag gaagccatcg acatgaggac    6060
```

```
cgccgtggag ctgctgaacg acgacgtgga gctgacaacc gacctggtgc gcgtgcaccc    6120
cgacagcagc ctggtgggcc ggaagggcta cagcaccacc gacggctccc tgtacagcta    6180
cttcgagggc accaagttca accaggccgc catcgatatg gccgagatcc tgaccctgtg    6240
gcccaggctg caggaagcca acgagcagat ctgtctgtac gccctgggcg agacaatgga    6300
caacatccgg tccaagtgcc ccgtgaacga cagcgacagc agcaccccce ctcggaccgt    6360 gccctgcctg tgcagatacg ccatgaccgc cgagcggatc gcccggctgc ggagccacca    6420
ggtgaagagc atggtggtgt gcagcagctt ccccctgccc aagtaccacg tggatggcgt    6480
gcagaaagtg aagtgcgaga aggtgctgct gttcgacccc accgtgccta gcgtggtgtc    6540
cccccggaag tacgccgcct ccaccaccga ccacagcgac agaagcctgc ggggcttcga    6600
cctggactgg accaccgact ccagcagcac cgccagcgac accatgagcc tgcccagcct    6660
gcagagctgc gacatcgaca gcatctacga gcctatggcc cccatcgtgg tgaccgccga    6720
cgtgcaccct gagccagccg gcatccgcga cctggccgcc gatgtgcacc cagaacccgc    6780
cgaccacgtg gatctggaaa accccatccc ccctcccaga cccaagaggg ccgcctacct    6840
ggccagcaga gccgccgaga ggcccgtgcc tgccccccaga aagcccaccc cagcccccag    6900
aaccgccttc aggaacaagc tgcccctgac cttcggcgac ttcgacgagc acgaggtgga    6960
cgccctggcc agcggcatca ccttcggcga ttttgatgac gtgctgcggc tgggcagagc    7020
cggagcctat atcttcagca gcgacaccgg ctccggccac ctgcagcaga aaagcgtgag    7080
acagcacaac ctgcagtgcg cccagctgga cgccgtggaa gaggaaaaga tgtaccccccc    7140 caagctggat accgagcggg aaaagctgct gctgctgaaa atgcagatgc accccagcga    7200
ggccaacaag agccgctacc agtctaggaa ggtggagaac atgaaggcca ccgtggtgga    7260
ccggctgacc agcggcgcca ggctgtacac aggggccgac gtgggcagaa tccctaccta    7320
cgccgtgcgc taccccaggc ccgtgtacag ccccaccgtg atcgagcggt tcagcagccc    7380
cgacgtggcc atcgccgcct gcaatgagta cctgtctagg aactacccaa ccgtgggccag    7440 ctaccagatc accgatgagt acgatgccta cctggacatg gtggacggca gcgacagctg    7500
cctggaccgg gccaccttct gtcccgccaa gctgcggtgc tacccccaagc accacgccta    7560 tcaccagccc accgtgagaa gcgccgtgcc cagcccctcc cagaatacce tgcagaatgt    7620 gctggccgcc gccaccaagc ggaactgcaa cgtgacccag atgagagaac tgcccacaat    7680
ggacagcgcc gtgtttaacg tggagtgctt caagagatac gcctgcagcg gcgagtactg    7740
ggaggaatac gccaagcagc ccatccggat caccaccgag aacatcacca cctacgtgac    7800
caagctgaag ggccccaagg ccgccgccct gttcgccaag acccacaacc tggtgcccct    7860
gcaggaagtg cctatggaca ggttcaccgt ggacatgaag cggacgtga aggtgacccc    7920 tggcaccaag cacaccgagg aacggcccaa ggtgcaggtg atccaggccg ccgagcctct    7980
ggccaccgcc tatctgtgcg gcatccaccg ggagctggtg cggcggctga acgccgtgct    8040
gaggcccaac gtgcacaccc tgttcgacat gtccgccgag gacttcgacg ccatcatcgc    8100
cagccacttc cacccggcg acccagtgct ggaaaccgat atcgccagct tcgacaagag    8160
ccaggacgac agcctggccc tgaccggcct gatgatcctg gaagatctgg gcgtggacca    8220
gtacctgctg gatctgatcg aggccgcctt cggcgagatc agcagctgcc acctgcctac    8280
cggcacccgt ttcaagttcg cgccatgat gaagagcggc atgtttctga ccctgttcat    8340
caacacagtg ctgaatatca ccatcgccag cagggtgctg aacagcggc tgaccgacag    8400
```

```
cgcctgcgcc gccttcatcg gcgacgacaa catcgtgcac ggcgtgatca gcgacaagct    8460
gatggccgag cggtgcgcca gctgggtgaa catggaagtg aagattatcg acgccgtgat    8520
gggcgaaaag ccccccctact tctgcggcgg cttcatcgtg ttcgacagcg tgacacagac    8580
cgcctgcaga gtgagcgacc ccctgaagcg gctgttcaag ctgggcaaac tctctgacagc    8640
cgaggacaag caggacgagg accggcggag ggccctgtcc gacgaggtgt ccaagtggtt    8700
ccggaccggc ctgggcgccg agctggaagt ggccctgaca agccgctacg aggtggaggg    8760
ctgcaagagc atcctgatcg ctatggccac cctggcccgg gacatcaagg cctttaagaa    8820
gctgagaggc cctgtcatcc acctgtacgg cggaccccgg ctggtgcggt gagagctcgc    8880
tgatcagcct cgactgtgcc ttctagttgc cagccatctg ttgtttgccc ctcccccgtg    8940
ccttccttga ccctggaagg tgccactccc actgtccttt cctaataaaa tgaggaaatt    9000
gcatcgcatt gtctgagtag gtgtcattct attctggggg gtggggtggg gcaggacagc    9060
aaggggagg attgggaaga caatagcagg catgcttaat taacaggcct tggcgcgccg    9120
ggtctgggta agctctagtt ctcatgtttg acagcttatc atcgataagc tttaatgcgg    9180
tagtttagca cgaaggagtc aacatgttag aagatctcaa acgctaggta ttagaagcca    9240
acctggcgct gccaaaacac aacctggtca cgctcacatg gggcaacgtc agcgccgttg    9300
atcgcgagcg cggcgtcttt gtgatcaaac cttccggcgt cgattacagc gtcatgaccg    9360
ctgacgatat ggtcgtggtt agcatcgaaa ccggtgaagt ggttgaaggt acgaaaaagc    9420
cctcctccga cacgccaact caccggctgc tctatcaggc attcccctcc attggcggca    9480
ttgtgcatac gcactcgcgc cacgccacca tctgggcgca ggcgggtcag tcgattccag    9540
caaccggcac cacccacgcc gactatttct acggcaccat tccctgcacc cgcaaaatga    9600
ccgacgcaga aatcaacggc gaatatgagt gggaaaccgg taacgtcatc gtagaaacct    9660
ttgaaaaaca gggtatcgat gcagcgcaaa tgcccggcgt tctggtccat tcccacggcc    9720
cgtttgcatg gggcaaaaat gccgaagatg cggtgcataa cgccatcgtg ctggaagagg    9780
tcgcttatat ggggatattc tgccgtcagt tagcgccgca gttaccggat atgcagcaaa    9840
cgctgctgga taaacactat ctgcgtaagc atggcgcgaa ggcatattac gggcagtaat    9900
gacagcccgc ctaatgagcg ggcttttttt tccatgacca aaatccctta acgtgagttt    9960
tcgttccact gagcgtcaga cccgtagaa aagatcaaag gatcttcttg agatcctttt    10020
tttctgcgcg taatctgctg cttgcaaaca aaaaaccac cgctaccagc ggtggtttgt    10080
ttgccggatc aagagctacc aactcttttt ccgaaggtaa ctggcttcag cagagcgcag    10140
ataccaaata ctgtccttct agtgtagccg tagttaggcc accacttcaa gaactctgta    10200
gcaccgccta catacctcgc tctgctaatc ctgttaccag tggctgctgc cagtggcgat    10260
aagtcgtgtc ttaccgggtt ggactcaaga cgatagttac cggataaggc gcagcggtcg    10320
ggctgaacgg ggggttcgtg ca                                             10342
```

<210> SEQ ID NO 6
<211> LENGTH: 10248
<212> TYPE: DNA
<213> ORGANISM: Artificial
<220> FEATURE:
<223> OTHER INFORMATION: Plasmid pheIF4A1-Nsp1234

<400> SEQUENCE: 6

```
cacagcccag cttggagcga acgacctaca ccgaactgag atacctacag cgtgagctat      60
gagaaagcgc cacgcttccc gaagggagaa aggcggacag gtatccggta agcggcaggg     120
```

| | |
|---|---|
| tcggaacagg agagcgcacg agggagcttc caggggggaaa cgcctggtat ctttatagtc | 180 |
| ctgtcgggtt tcgccacctc tgacttgagc gtcgattttt gtgatgctcg tcagggggggc | 240 |
| ggagcctatg gaaaaacgcc agcaacgcat cgataaaata aaagatttta tttagtctcc | 300 |
| agaaaaaggg gggaatgaaa gaccccacct gtaggtttgg caagctagcg tatacggatc | 360 |
| ctctagctag atgatttcct tcatccctgg cacacgtcca ggcagtgtcg aatccatctc | 420 |
| tgctacaggg gaaaacaaat aacatttgag tccagtggag accgggagca gaagtaaagg | 480 |
| gaagtgataa cccccagagc ccggaagcct ctggaggctg agacctcgcc ccccttgcgt | 540 |
| gatagggcct acgagccac atgaccaagg cactgtcgcc tccgcacgtg tgagagtgca | 600 |
| gggcccccaag atggctgcca ggcctcgagg cctgactctt ctatgtcact tccgtaccgg | 660 |
| cgagaaaggc gggcccctcca gccaatgagg ctgcggggcg ggccttcacc ttgataggca | 720 |
| ctcgagttat ccaatggtgc ctgcgggccg gagcgactag gaactaacgt catgccgagt | 780 |
| tgctgagcgc cggcaggcgg ggccggggcg gccaaaccaa tgcgatggcc ggggcggagt | 840 |
| cgggcgctct ataagttgtc gataggcggg cactccgccc tagtttctaa ggaaccggtc | 900 |
| gccaccatgg ccgccaaggt gcacgtggac atcgaggccg acagccccctt catcaagagc | 960 |
| ctgcagaagg ccttccccag cttcgaggtg gagtccctgc aggtgacccc caacgaccac | 1020 |
| gccaacgcca gggccttcag ccacctggcc accaagctga tcgagcagga aaccgacaag | 1080 |
| gacacccctga tcctggacat cggcagcgcc ccctcaaggt gagtttgggg acccttgatt | 1140 |
| gttctttctt tttcgctatt gtaaaattca tgttatatgg aggggggcaaa gttttcaggg | 1200 |
| tgttgtttag aatgggaaga tgtcccttgt atcactatgg accctcatga taattttgtt | 1260 |
| tctttcactt tctactctgt tgacaaccat tgtctcctct tatttttcttt tcattttctg | 1320 |
| taacttttc gttaaacttt agcttgcatt tgtaacgaat ttttaaattc acttttgttt | 1380 |
| atttgtcaga ttgtaagtac tttctctaat cactttttttt tcaaggcaat cagggtatat | 1440 |
| tatattgtac ttcagcacag ttttagagaa caattgttat aattaaatga taaggtagaa | 1500 |
| tatttctgca tataaaattct ggctggcgtg gaaatattct tattggtaga aacaactaca | 1560 |
| ccctggtcat catcctgcct ttctctttat ggttacaatg atatacactg tttgagatga | 1620 |
| ggataaaaata ctctgagtcc aaaccggggcc cctctgctaa ccatgttcat gccttcttct | 1680 |
| ttttcctaca ggcggatgat gagcacccac aagtaccact cgtgtgccc catgcggagc | 1740 |
| gccgaggacc ccgagcggct ggtgtgctac gccaagaagc tggccgccgc cagcggcaag | 1800 |
| gtgctggacc gggagatcgc cggcaagatc accgacctgc agaccgtgat ggccaccccc | 1860 |
| gacgccgaga gccccacctt ctgcctgcac accgacgtga cctgccggac agccgccgag | 1920 |
| gtggccgtgt accaggacgt gtacgccgtg cacgccccca cctccctgta ccaccaggcc | 1980 |
| atgaagggcg tgcggaccgc ctactggatc ggcttcgaca ccaccccctt catgttcgac | 2040 |
| gccctggccg gagcctaccc cacctacgcc accaactggg ccgacgagca ggtgctgcag | 2100 |
| gccccggaaca tcggcctgtg cgccgccagc ctgaccgagg gccggctggg caagctgtcc | 2160 |
| atcctgcgga gaagcagct gaagccctgc gacaccgtga tgttcagcgt gggcagcaca | 2220 |
| ctgtacaccg agagccggaa gctgctgcgg agctggcacc tgcccagcgt gttccacctg | 2280 |
| aagggcaagc agagcttcac ctgcagatgc gacaccatcg tgagctgcga gggctacgtg | 2340 |
| gtgaagaaaa tcaccatgtg ccctggcctg tacggcaaga ccgtgggcta cgccgtgacc | 2400 |
| taccacgccg agggctttct ggtgtgcaag accaccgata ccgtgaaggg cgagagagtg | 2460 |

| | |
|---|---|
| agcttccccg tctgcaccta cgtgcccagc accatctgcg accagatgac cggtatcctg | 2520 |
| gccaccgatg tgaccccga ggacgcccag aaactgctgg tcggcctgaa ccagcggatc | 2580 |
| gtggtgaacg ccggaccca gcggaacacc aacaccatga agaactacct gctgcccatc | 2640 |
| gtggccgtgg ccttcagcaa gtgggccaga gagtacaagg ccgacctgga cgacgagaag | 2700 |
| cccctgggcg tgcgggagcg gagcctgacc tgctgctgcc tgtgggcctt caagacccgg | 2760 |
| aagatgcaca ccatgtacaa gaagcccgac acccagacca tcgtgaaggt gcccagcgag | 2820 |
| ttcaacagct tcgtgatccc cagcctgtgg agcaccggcc tggccatccc cgtgcggagc | 2880 |
| cggatcaaga tgctgctggc caagaaaacc aagcgggagc tgatccccgt gctggacgcc | 2940 |
| agcagcgcca gggacgccga gcaggaagag aaagagcggc tggaagccga gctgacccgg | 3000 |
| gaggccctgc cccccctggt gcctatcgcc cctgccgaga ccggcgtggt ggacgtggat | 3060 |
| gtggaggaac tggaatacca cgccggagcc ggggtggtgg agacccccag atccgccctg | 3120 |
| aaggtgacag cccagcccaa cgacgtgctg ctgggcaact acgtggtgct gtcccccag | 3180 |
| accgtgctga agagcagcaa gctggccccc gtgcaccctc tggccgagca ggtgaagatc | 3240 |
| atcacccaca cggcagggc cggcagatac caggtcgacg gctacgacgg ccgggtgctg | 3300 |
| ctgccatgcg gctccgccat ccctgtgccc gagttccagg ccctgagcga gagcgccaca | 3360 |
| atggtgtaca acgagcggga gttcgtgaac cggaagctgt accacattgc cgtgcacggc | 3420 |
| cctagcctga acaccgatga ggaaaactac agaaagtgc gggccgagcg gaccgatgcc | 3480 |
| gagtacgtgt cgacgtgga caagaaatgc tgcgtgaagc gggaggaagc cagcgggctg | 3540 |
| gtgctggtcg gggagctgac caaccccccc ttccacgagt tcgcctacga gggcctgaag | 3600 |
| atccggccct ccgcccccta caagaccaca gtggtgggcg tgttcggcgt gcccggcagc | 3660 |
| ggcaagagcg ccatcatcaa gtccctggtg accaagcacg acctggtgac ctccggcaag | 3720 |
| aaagagaact gccaggaaat cgtcaacgac gtcaagaagc accggggcct ggacatccag | 3780 |
| gccaagacag tggacagcat cctgctgaac ggctgcagac gggccgtgga tatcctgtac | 3840 |
| gtggacgagg ccttcgcctg ccacagcggc accctgctgg ccctgatcgc cctggtgaag | 3900 |
| ccccggtcca aggtggtgct gtgcggcgac cccaagcagt gcggcttctt caacatgatg | 3960 |
| cagctgaagg tgaacttcaa ccacaacatc tgcaccgaag tgtgccacaa gagcatcagc | 4020 |
| cggcggtgca ccagacccgt gaccgccatc gtgtccaccc tgcactacgg cggcaagatg | 4080 |
| cggaccacca ccccctgcaa caagcccatc atcatcgata ccaccggcca gaccaagccc | 4140 |
| aagcccggcg acatcgtgct gacctgcttc cgcggctggg tgaagcagct gcagctggac | 4200 |
| taccggggcc acgaggtgat gaccgccgcc gcctcccagg gcctgaccag aaagggcgtg | 4260 |
| tatgccgtgc ggcagaaggt gaacgagaac cccctgtacg cccctgccag cgagcacgtg | 4320 |
| aatgtgctgc tgacccggac cgaggacagg ctggtgtgga aaaccctggc cggcgacccc | 4380 |
| tggatcaagg tgctgtccaa catcccccag ggcaacttca ccgccaccct ggaagagtgg | 4440 |
| caggaagagc acgacaagat catgaaggtg atcgagggcc ctgccgcccc agtggacgcc | 4500 |
| ttccagaaca aggccaacgt gtgctggccc aagagcctgg tgcctgtgct ggacaccgcc | 4560 |
| ggcatccggt gaccgccga agagtggagc accatcatca ccgccttcaa agaggaccgg | 4620 |
| gcctacagcc ccgtggtggc cctgaacgag atctgcacca agtactacgg cgtggacctg | 4680 |
| gacagcggcc tgttcagcgc ccccaaggtg tccctgtact acgagaacaa ccactgggac | 4740 |
| aaccggccag cgcaggat gtacggcttc aacgccgcca ccgccgccag actgaagcc | 4800 |
| cggcacacct ttctgaaggg ccagtggcac accggcaagc aggccgtgat cgccgagaga | 4860 |

```
aagatccagc ccctgtccgt gctggataac gtgatccta tcaaccggcg gctgccccac    4920
gccctggtgg ccgagtacaa gacagtgaag ggcagccggg tggagtggct ggtgaacaaa    4980
gtgcggggct accacgtgct gctggtgtct gagtacaacc tggccctgcc tcggcggagg    5040
gtgacctggc tgtccctct gaacgtgaca ggcgccgaca ggtgctacga cctgagcctg     5100
ggcctgcctg ccgacgccgg cagattcgac ctggtgttcg tgaacatcca caccgagttc    5160
agaatccacc actaccagca gtgcgtggac cacgccatga agctgcagat gctgggcggc    5220
gacgccctga ggctgctgaa gcctggcggc agcctgctga tgcgggccta cggctacgcc    5280
gacaagatct ccgaggccgt ggtgtccagc ctgagccgga agttcagctc cgccagggtg    5340
ctgagacccg actgcgtgac cagcaacaca gaagtgtttc tgctgttcag caacttcgac    5400
aacggcaagc ggcccagcac cctgcaccag atgaacacca gctgtccgc cgtgtacgcc     5460
ggcgaggcca tgcacaccgc cggatgcgcc ccagctaccc gggtgaagcg ggccgacatc    5520
gccacctgca ccgaggccgc cgtggtgaat gccgccaatg ccaggggcac cgtgggcgac    5580
ggcgtgtgca gggccgtggc caaaaagtgg cccagcgcct tcaagggcga ggccacccct    5640
gtgggcacca tcaaaaccgt gatgtgcggc agctaccccg tgatccacgc cgtggccccc    5700
aatttcagcg ccaccacaga ggccgagggc gaccgggaac tggccgccgt gtatagagcc    5760
gtggccgccg aagtgaacag actgagcctg agcagcgtgg ccatccctct gctgtccacc    5820
ggcgtgttca gcggcggcag ggaccggctg cagcagagcc tgaaccacct gttcaccgct    5880
atggacgcca ccgacgccga cgtgacaatc tactgccggg acaagagctg ggagaagaag    5940
atccaggaag ccatcgacat gaggaccgcc gtggagctgc tgaacgacga cgtggagctg    6000
acaaccgacc tggtgcgcgt gcaccccgac agcagcctgg tgggccggaa gggctacagc    6060
accaccgacg gctccctgta cagctacttc gagggcacca agttcaacca ggccgccatc    6120
gatatggccg agatcctgac cctgtggccc aggctgcagg aagccaacga gcagatctgt    6180
ctgtacgccc tgggcgagac aatggacaac atccggtcca gtgcccgt gaacgacagc      6240
gacagcagca cccccctcg gaccgtgccc tgcctgtgca gatacgccat gaccgccgag    6300
cggatcgccc ggctgcggag ccaccaggtg aagagcatgg tggtgtgcag cagcttcccc    6360
ctgcccaagt accacgtgga tggcgtgcag aaagtgaagt gcgagaaggt gctgctgttc    6420
gacccaccg tgcctagcgt ggtgtccccc cggaagtacg ccgcctccac caccgaccac     6480
agcgacagaa gcctgcgggg cttcgacctg gactggacca ccgactccag cagcaccgcc    6540
agcgacacca tgagcctgcc cagcctgcag agctgcgaca tcgacagcat ctacgagcct    6600
atggccccca tcgtggtgac cgccgacgtg cacctgagc cagccggcat cgccgacctg     6660
gccgccgatg tgcacccaga acccgccgac cacgtggatc tggaaaaccc catccccct    6720
cccagaccca agagggccgc ctacctggcc agcagagccg ccgagaggcc cgtgcctgcc    6780
cccagaaagc ccaccccagc ccccagaacc gccttcagga acaagctgcc cctgaccttc    6840
ggcgacttcg acgagcacga ggtggacgcc ctggccagcg gcatcacctt cggcgatttt    6900
gatgacgtgc tgcggctggg cagagccgga gcctatatct tcagcagcga caccggctcc    6960
ggccacctgc agcagaaaag cgtgagacag cacaacctgc agtgcgccca gctggacgcc    7020
gtggaagagg aaaagatgta cccccccaag ctggataccg agcgggaaaa gctgctgctg    7080
ctgaaaatgc agatgcaccc cagcgaggcc aacaagagcc gctaccagtc taggaaggtg    7140
gagaacatga aggccaccgt ggtggaccgg ctgaccagcg gcgccaggct gtacacaggg    7200
```

```
gccgacgtgg gcagaatccc tacctacgcc gtgcgctacc ccaggcccgt gtacagcccc    7260
accgtgatcg agcggttcag cagccccgac gtggccatcg ccgcctgcaa tgagtacctg    7320
tctaggaact acccaaccgt ggccagctac cagatcaccg atgagtacga tgcctacctg    7380
gacatggtgg acggcagcga cagctgcctg gaccgggcca ccttctgtcc cgccaagctg    7440
cggtgctacc ccaagcacca cgcctatcac cagcccaccg tgagaagcgc cgtgcccagc    7500
cccttccaga atacccctgca gaatgtgctg ccgccgcca ccaagcggaa ctgcaacgtg    7560
acccagatga gagaactgcc cacaatggac agcgccgtgt taacgtgga gtgcttcaag    7620 agatacgcct gcagcggcga gtactgggag gaatacgcca agcagcccat ccggatcacc    7680
accgagaaca tcaccaccta cgtgaccaag ctgaagggcc caaggccgc cgccctgttc    7740 gccaagaccc acaacctggt gcccctgcag gaagtgccta tggacaggtt caccgtggac    7800
atgaagcggg acgtgaaggt gacccctggc accaagcaca ccgaggaacg gcccaaggtg    7860
caggtgatcc aggccgccga gcctctggcc accgcctatc tgtgcggcat ccaccgggag    7920
ctggtgcggc ggctgaacgc cgtgctgagg cccaacgtgc acaccctgtt cgacatgtcc    7980
gccgaggact tcgacgccat catcgccagc cacttccacc ccggcgaccc agtgctggaa    8040
accgatatcg ccagcttcga caagagccag gacgacagcc tggccctgac cggcctgatg    8100
atcctggaag atctgggcgt ggaccagtac ctgctggatc tgatcgaggc cgccttcggc    8160
gagatcagca gctgccacct gcctaccggc acccggttca gttcggcgc catgatgaag    8220 agcggcatgt ttctgaccct gttcatcaac acagtgctga atatcaccat cgccagcagg    8280
gtgctggaac agcggctgac cgacagcgcc tgcgccgcct tcatcggcga cgacaacatc    8340
gtgcacggcg tgatcagcga caagctgatg gccgagcggt gcgccagctg ggtgaacatg    8400
gaagtgaaga ttatcgacgc cgtgatgggc gaaaagcccc cctacttctg cggcggcttc    8460
atcgtgttcg acagcgtgac acagaccgcc tgcagagtga gcgacccccct gaagcggctg    8520 ttcaagctgg gcaaacctct gacagccgag gacaagcagg acgaggaccg gcggagggcc    8580
ctgtccgacg aggtgtccaa gtggttccgg accggcctgg gcgccgagct ggaagtggcc    8640
ctgacaagcc gctacgaggt ggagggctgc aagagcatcc tgatcgctat ggccaccctg    8700
gcccgggaca tcaaggcctt taagaagctg agaggccctg tcatccacct gtacggcgga    8760
ccccggctgt gcggtgaga gctgctgat cagcctcgac tgtgccttct agttgccagc    8820
catctgttgt ttgcccctcc ccgtgccttt ccttgaccct ggaaggtgcc actcccactg    8880
tcctttccta ataaaatgag gaaattgcat cgcattgtct gagtaggtgt cattctattc    8940
tggggggtgg ggtggggcag gacagcaagg gggaggattg gaagacaat agcaggcatg    9000 cttaattaac aggccttggc gcgccgggtc tgggtaagct ctagttctca tgtttgacag    9060
cttatcatcg ataagcttta atgcggtagt ttagcacgaa ggagtcaaca tgttagaaga    9120
tctcaaacgc taggtattag aagccaacct ggcgctgcca aaacacaacc tggtcacgct    9180
cacatggggc aacgtcagcg ccgttgatcg cgagcgcggc gtctttgtga tcaaaccttc    9240
cggcgtcgat tacagcgtca tgaccgctga cgatatggtc gtggttagca tcgaaaccgg    9300
tgaagtggtt gaaggtacga aaaagcccctc ctccgacacg ccaactcacc ggctgctcta    9360
tcaggcattc ccctccattg gcggcattgt gcatacgcac tcgcgccacg ccaccatctg    9420
ggcgcaggcg gtcagtcga ttccagcaac cggcaccacc cacgccgact atttctacgg    9480
caccattccc tgcacccgca aaatgaccga cgcagaaatc aacggcgaat atgagtggga    9540
aaccggtaac gtcatcgtag aaacctttga aaaacagggt atcgatgcag cgcaaatgcc    9600
```

| | | | | |
|---|---|---|---|---|
| cggcgttctg | gtccattccc | acggcccgtt | tgcatggggc | aaaaatgccg aagatgcggt | 9660 |
| gcataacgcc | atcgtgctgg | aagaggtcgc | ttatatgggg | atattctgcc gtcagttagc | 9720 |
| gccgcagtta | ccggatatgc | agcaaacgct | gctggataaa | cactatctgc gtaagcatgg | 9780 |
| cgcgaaggca | tattacgggc | agtaatgaca | gcccgcctaa | tgagcgggct ttttttttcca | 9840 |
| tgaccaaaat | cccttaacgt | gagttttcgt | tccactgagc | gtcagacccc gtagaaaaga | 9900 |
| tcaaaggatc | ttcttgagat | cctttttttc | tgcgcgtaat | ctgctgcttg caaacaaaaa | 9960 |
| aaccaccgct | accagcggtg | gtttgtttgc | cggatcaaga | gctaccaact cttttttccga | 10020 |
| aggtaactgg | cttcagcaga | gcgcagatac | caaatactgt | ccttctagtg tagccgtagt | 10080 |
| taggccacca | cttcaagaac | tctgtagcac | cgcctacata | cctcgctctg ctaatcctgt | 10140 |
| taccagtggc | tgctgccagt | ggcgataagt | cgtgtcttac | cgggttggac tcaagacgat | 10200 |
| agttaccgga | taaggcgcag | cggtcgggct | gaacggggg | ttcgtgca | 10248 |

<210> SEQ ID NO 7
<211> LENGTH: 10258
<212> TYPE: DNA
<213> ORGANISM: Artificial
<220> FEATURE:
<223> OTHER INFORMATION: Plasmid phEF1aHTLV-Nsp1234

<400> SEQUENCE: 7

| | | | | |
|---|---|---|---|---|
| cacagcccag | cttggagcga | acgacctaca | ccgaactgag | atacctacag cgtgagctat | 60 |
| gagaaagcgc | cacgcttccc | gaagggagaa | aggcggacag | gtatccggta agcggcaggg | 120 |
| tcggaacagg | agagcgcacg | agggagcttc | caggggggaaa | cgcctggtat ctttatagtc | 180 |
| ctgtcgggtt | tcgccacctc | tgacttgagc | gtcgatttt | gtgatgctcg tcagggggc | 240 |
| ggagcctatg | gaaaaacgcc | agcaacgcat | cgataaaata | aagattttta tttagtctcc | 300 |
| agaaaaaggg | gggaatgaaa | gaccccacct | gtaggtttgg | caagctagcg tatacggatc | 360 |
| ctctagctag | agctccggtg | cccgtcagtg | ggcagagcgc | acatcgccca cagtccccga | 420 |
| gaagttgggg | ggaggggtcg | gcaattgaac | cggtgcctag | agaaggtggc gcggggtaaa | 480 |
| ctgggaaagt | gatgtcgtgt | actggctccg | ccttttttccc | gagggtgggg gagaaccgta | 540 |
| tataagtgca | gtagtcgccg | tgaacgttct | ttttcgcaac | gggtttgccg ccagaacaca | 600 |
| gctgaagctt | cgaggggctc | gcatctctcc | ttcacgcgcc | cgccgcccta cctgaggccg | 660 |
| ccatccacgc | cggttgagtc | gcgttctgcc | gcctcccgcc | tgtggtgcct cctgaactgc | 720 |
| gtccgccgtc | taggtaagtt | taaagctcag | gtcgagaccg | gcctttgtc cggcgctccc | 780 |
| ttggagccta | cctagactca | gccggctctc | cacgctttgc | ctgaccctgc ttgctcaact | 840 |
| ctacgtcttt | gtttcgtttt | ctgttctgcg | ccgttacaga | tccaagctgt gaccggcgcc | 900 |
| tactccggtc | gccaccatgg | ccgccaaggt | gcacgtggac | atcgaggccg acagcccctt | 960 |
| catcaagagc | ctgcagaagg | ccttccccag | cttcgaggtg | gagtccctgc aggtgacccc | 1020 |
| caacgaccac | gccaacgcca | gggccttcag | ccacctggcc | accaagctga tcgagcagga | 1080 |
| aaccgacaag | gacacccctga | tcctggacat | cggcagcgcc | ccctcaaggt gagtttgggg | 1140 |
| acccttgatt | gttctttctt | tttcgctatt | gtaaaattca | tgttatatgg aggggcaaa | 1200 |
| gttttcaggg | tgttgtttag | aatgggaaga | tgtcccttgt | atcactatgg accctcatga | 1260 |
| taattttgtt | tctttcactt | tctactctgt | tgacaaccat | tgtctcctct tattttcttt | 1320 |
| tcattttctg | taacttttttc | gttaaacttt | agcttgcatt | tgtaacgaat ttttaaattc | 1380 |

```
acttttgttt atttgtcaga ttgtaagtac tttctctaat cacttttttt tcaaggcaat    1440
cagggtatat tatattgtac ttcagcacag ttttagagaa caattgttat aattaaatga    1500
taaggtagaa tatttctgca tataaattct ggctggcgtg gaaatattct tattggtaga    1560
aacaactaca ccctggtcat catcctgcct ttctctttat ggttacaatg atatacactg    1620
tttgagatga ggataaaata ctctgagtcc aaaccgggcc cctctgctaa ccatgttcat    1680
gccttcttct ttttcctaca ggcggatgat gagcacccac aagtaccact gcgtgtgccc    1740
catgcggagc gccgaggacc ccgagcggct ggtgtgctac gccaagaagc tggccgccgc    1800
cagcggcaag gtgctggacc gggagatcgc cggcaagatc accgacctgc agaccgtgat    1860
ggccaccccc gacgccgaga gccccacctt ctgcctgcac accgacgtga cctgccggac    1920
agccgccgag gtggccgtgt accaggacgt gtacgccgtg cacgccccca cctccctgta    1980
ccaccaggcc atgaagggcg tgcggaccgc ctactggatc ggcttcgaca ccacccccctt    2040
catgttcgac gccctggccg agcctaccc cacctacgcc accaactggg ccgacgagca    2100
ggtgctgcag gcccggaaca tcggcctgtg cgccgccagc ctgaccgagg ccggctgggg    2160
caagctgtcc atcctgcgga gaagcagct gaagccctgc gacaccgtga tgttcagcgt    2220
gggcagcaca ctgtacaccg agagccggaa gctgctgcgg agctggcacc tgcccagcgt    2280
gttccacctg aagggcaagc agagcttcac ctgcagatgc gacaccatcg tgagctgcga    2340
gggctacgtg gtgaagaaaa tcaccatgtg ccctggcctg tacggcaaga ccgtgggcta    2400
cgccgtgacc taccacgccg agggcttcct ggtgtgcaag accaccgata ccgtgaaggg    2460
cgagagagtg agcttcccg tctgcaccta cgtgcccagc accatctgcg accagatgac    2520
cggtatcctg gccaccgatg tgacccccga ggacgcccag aaactgctgg tcggcctgaa    2580
ccagcggatc gtggtgaacg gccggaccca gcggaacacc aacaccatga gaaactacct    2640
gctgcccatc gtggccgtgg ccttcagcaa gtgggccaga gagtacaagg ccgacctgga    2700
cgacgagaag cccctgggcg tgcgggagcg gagcctgacc tgctgctgcc tgtgggcctt    2760
caagacccgg aagatgcaca ccatgtacaa gaagcccgac acccagacca tcgtgaaggt    2820
gcccagcgag ttcaacagct tcgtgatccc cagcctgtgg agcaccggcc tggccatccc    2880
cgtgcggagc cggatcaaga tgctgctggc caagaaaacc aagcgggagc tgatccccgt    2940
gctggacgcc agcagcgcca gggacgccga gcaggaagag aaagagcggc tggaagccga    3000
gctgacccgg gaggccctgc ccccctggt gcctatcgcc cctgccgaga ccggcgtggt    3060
ggacgtggat gtggaggaac tggaatacca cgccggagcc ggggtggtgg agaccccag    3120
atccgccctg aaggtgacag cccagcccaa cgacgtgctg ctgggcaact acgtggtgct    3180
gtcccccccag accgtgctga agagcagcaa gctggccccc gtgcaccctc tggccgagca    3240
ggtgaagatc atcacccaca acggcagggc cggcagatac caggtcgacg gctacgacgg    3300
ccgggtgctg ctgccatgcg gctccgccat ccctgtgccc gagttccagg ccctgagcga    3360
gagcgccaca atggtgtaca acgagcggga gttcgtgaac cggaagctgt accacattgc    3420
cgtgcacggc cctagcctga acaccgatga ggaaaactac gagaaagtgc gggccgagcg    3480
gaccgatgcc gagtacgtgt tcgacgtgga caagaaatgc tgcgtgaagc gggaggaagc    3540
cagcgggctg gtgctggtcg gggagctgac caacccccc ttccacgagt tcgcctacga    3600
gggcctgaag atccggccct ccgcccccta caagaccaca gtggtgggcg tgttcggcgt    3660
gcccggcagc ggcaagagcg ccatcatcaa gtccctggtg accaagcacg acctggtgac    3720
ctccggcaag aaagagaact gccaggaaat cgtcaacgac gtcaagaagc accggggcct    3780
```

```
ggacatccag gccaagacag tggacagcat cctgctgaac ggctgcagac gggccgtgga   3840
tatcctgtac gtggacgagg ccttcgcctg ccacagcggc accctgctgg ccctgatcgc   3900
cctggtgaag ccccggtcca aggtggtgct gtgcggcgac cccaagcagt gcggcttctt   3960
caacatgatg cagctgaagg tgaacttcaa ccacaacatc tgcaccgaag tgtgccacaa   4020
gagcatcagc cggcggtgca ccagacccgt gaccgccatc gtgtccaccc tgcactacgg   4080
cggcaagatg cggaccacca cccctgcaa caagcccatc atcatcgata ccaccggcca    4140
gaccaagccc aagcccggcg acatcgtgct gacctgcttc cgcggctggg tgaagcagct   4200
gcagctggac taccggggcc acgaggtgat gaccgccgcc gcctcccagg gcctgaccag   4260
aaagggcgtg tatgccgtgc ggcagaaggt gaacgagaac cccctgtacg cccctgccag   4320
cgagcacgtg aatgtgctgc tgaccccgga cgaggacagg ctggtgtgga aaaccctggc   4380
cggcgacccc tggatcaagg tgctgtccaa catcccccag ggcaacttca ccgccaccct   4440
ggaagagtgg caggaagagc acgacaagat catgaaggtg atcgagggcc tgccgcccc    4500 agtggacgcc ttccagaaca aggccaacgt gtgctgggcc aagagcctgg tgcctgtgct   4560
ggacaccgcc ggcatccggc tgaccgccga agagtggagc accatcatca ccgccttcaa   4620
agaggaccgg gcctacagcc ccgtggtggc cctgaacgag atctgcacca agtactacgg   4680
cgtggacctg gacagcggcc tgttcagcgc ccccaaggtg tccctgtact acgagaacaa   4740
ccactgggac aaccggccag gcggcaggat gtacggcttc aacgccgcca ccgccgccag   4800
actggaagcc cggcacacct ttctgaaggg ccagtggcac accggcaagc aggccgtgat   4860
cgccgagaga aagatccagc ccctgtccgt gctggataac gtgatcccta tcaaccggcg   4920
gctgccccac gccctggtgg ccgagtacaa cagtgaag   ggcagccggg tggagtggct   4980
ggtgaacaaa gtgcggggct accacgtgct gctggtgtct gagtacaacc tggccctgcc   5040
tcggcggagg gtgacctggc tgtcccctct gaacgtgaca ggcgccgaca ggtgctacga   5100
cctgagcctg ggcctgcctg ccgacgccgg cagattcgac ctggtgttcg tgaacatcca   5160
caccgagttc agaatccacc actaccagca gtgcgtggac cacgccatga agctgcagat   5220
gctgggcggc gacgccctga ggctgctgaa gcctggcggc agcctgctga tgcgggccta   5280
cggctacgcc gacaagatct ccgaggccgt ggtgtccagc ctgagccgga gttcagctc    5340 cgccagggtg ctgagacccg actgcgtgac cagcaacaca gaagtgtttc tgctgttcag   5400
caacttcgac aacggcaagc ggcccagcac cctgcaccag atgaacacca agctgtccgc   5460
cgtgtacgcc ggcgaggcca tgcacaccgc cggatgcgcc cccagctacc gggtgaagcg   5520
ggccgacatc gccacctgca ccgaggccgc cgtggtgaat gccgccaatg ccaggggcac   5580
cgtgggcgac ggcgtgtgca gggccgtggc caaaaagtgg cccagcgcct tcaagggcga   5640 ggccaccct gtgggcacca tcaaaaccgt gatgtgcggc agctaccccg tgatccacgc    5700
cgtggccccc aatttcagcg ccaccacaga ggccgagggc gaccgggaac tggccgccgt   5760
gtatagagcc gtggccgccg aagtgaacag actgagcctg agcagcgtgg ccatccctct   5820
gctgtccacc ggcgtgttca gcggcggcag ggaccggctg cagcagagcc tgaaccacct   5880
gttcaccgct atggacgcca ccgacgccga cgtgacaatc tactgccggg acaagagctg   5940
ggagaagaag atccaggaag ccatcgacat gaggaccgcc gtggagctgc tgaacgacga   6000
cgtggagctg acaaccgacc tggtgcgcgt gcacccgac agcagcctgg tgggccggaa     6060
gggctacagc accaccgacg gctccctgta cagctacttc gagggcacca agttcaacca   6120
```

```
ggccgccatc gatatggccg agatcctgac cctgtggccc aggctgcagg aagccaacga    6180
gcagatctgt ctgtacgccc tgggcgagac aatggacaac atccggtcca agtgccccgt    6240
gaacgacagc gacagcagca ccccccctcg gaccgtgccc tgcctgtgca gatacgccat    6300
gaccgccgag cggatcgccc ggctgcggag ccaccaggtg aagagcatgg tggtgtgcag    6360
cagcttcccc ctgcccaagt accacgtgga tggcgtgcag aaagtgaagt gcgagaaggt    6420
gctgctgttc gaccccaccg tgcctagcgt ggtgtccccc cggaagtacg ccgcctccac    6480
caccgaccac agcgacagaa gcctgcgggg cttcgacctg gactggacca ccgactccag    6540
cagcaccgcc agcgacacca tgagcctgcc agcctgcag agctgcgaca tcgacagcat    6600
ctacgagcct atggccccca tcgtggtgac cgccgacgtg caccctgagc cagccggcat    6660
cgccgacctg gccgccgatg tgcacccaga accgccgac cacgtggatc tggaaaaccc    6720
catccccct cccagaccca gagggccgc ctacctggcc agcagagccg ccgagaggcc    6780
cgtgcctgcc cccagaaagc ccaccccagc ccccagaacc gccttcagga acaagctgcc    6840
cctgaccttc ggcgacttcg acgagcacga ggtggacgc ctggccagcg gcatcacctt    6900
cggcgatttt gatgacgtgc tgcggctggg cagagccgga gcctatatct tcagcagcga    6960
caccggctcc ggccacctgc agcagaaaag cgtgagacac acaacctgc agtgcgccca    7020
gctggacgcc gtggaagagg aaaagatgta cccccccaag ctggataccg agcgggaaaa    7080
gctgctgctg ctgaaaatgc agatgcaccc cagcgaggcc aacaagagcc gctaccagtc    7140
taggaaggtg gagaacatga aggccaccgt ggtggaccgg ctgaccagcg cgccaggct    7200
gtacacaggg gccgacgtgg gcagaatccc tacctacgcc gtgcgctacc ccaggcccgt    7260
gtacagcccc accgtgatcg agcggttcag cagccccgac gtggccatcg ccgcctgcaa    7320
tgagtacctg tctaggaact acccaaccgt ggccagctac cagatcaccg atgagtacga    7380
tgcctacctg gacatggtgg acggcagcga cagctgcctg gaccgggcca ccttctgtcc    7440
cgccaagctg cggtgctacc ccaagcacca cgcctatcac cagcccaccg tgagaagcgc    7500
cgtgcccagc ccctccaga atacctgca gaatgtgctg gccgccgcca ccagcggaa    7560
ctgcaacgtg acccagatga gagaactgcc cacaatggac agcgccgtgt ttaacgtgga    7620
gtgcttcaag agatacgcct gcagcggcga gtactgggag gaatacgcca gcagcccat    7680
ccggatcacc accgagaaca tcaccaccta cgtgaccaag ctgaagggcc caaggccgc    7740
cgccctgttc gccaagaccc acaacctggt gccctgcag gaagtgccta tggacaggtt    7800
caccgtggac atgaagcggg acgtgaaggt gaccccctgc accaagcaca ccgaggaacg    7860
gcccaaggtg caggtgatcc aggccgccga gcctctggcc accgcctatc tgtgcggcat    7920
ccaccgggag ctggtgcggc ggctgaacgc cgtgctgagg cccaacgtgc acccctgtt    7980
cgacatgtcc gccgaggact cgacgccat catcgccagc cacttccacc ccggcgaccc    8040
agtgctggaa accgatatcg ccagcttcga caagagccag gacgacagcc tggccctgac    8100
cggcctgatg atcctggaag atctgggcgt ggaccagtac ctgctggatc tgatcgaggc    8160
cgccttcggc gagatcagca gctgccacct gcctaccggc acccggttca gttcggcgc    8220
catgatgaag agcggcatgt ttctgaccct gttcatcaac acagtgctga atatcaccat    8280
cgccagcagg gtgctggaac agcggctgac cgacagcgcc tgcgccgcct tcatcggcga    8340
cgacaacatc gtgcacggcg tgatcagcga caagctgatg gccgagcggt gcgcagctg    8400
ggtgaacatg gaagtgaaga ttatcgacgc cgtgatgggc gaaaagcccc cctacttctg    8460
cggcggcttc atcgtgttcg acagcgtgac acagaccgcc tgcagagtga cgaccccct    8520
```

```
gaagcggctg ttcaagctgg gcaaacctct gacagccgag gacaagcagg acgaggaccg    8580
gcggagggcc ctgtccgacg aggtgtccaa gtggttccgg accggcctgg gcgccgagct    8640
ggaagtggcc ctgacaagcc gctacgaggt ggagggctgc aagagcatcc tgatcgctat    8700
ggccaccctg gcccgggaca tcaaggcctt taagaagctg agaggccctg tcatccacct    8760
gtacggcgga ccccggctgg tgcggtgaga gctcgctgat cagcctcgac tgtgccttct    8820
agttgccagc catctgttgt ttgcccctcc cccgtgcctt ccttgaccct ggaaggtgcc    8880
actcccactg tcctttccta ataaaatgag gaaattgcat cgcattgtct gagtaggtgt    8940
cattctattc tggggggtgg ggtggggcag gacagcaagg gggaggattg ggaagacaat    9000
agcaggcatg cttaattaac aggccttggc gcgccgggtc tgggtaagct ctagttctca    9060
tgtttgacag cttatcatcg ataagcttta atgcggtagt ttagcacgaa ggagtcaaca    9120
tgttagaaga tctcaaacgc taggtattag aagccaacct ggcgctgcca aaacacaacc    9180
tggtcacgct cacatggggc aacgtcagcg ccgttgatcg cgagcgcggc gtctttgtga    9240
tcaaaccttc cggcgtcgat tacagcgtca tgaccgctga cgatatggtc gtggttagca    9300
tcgaaaccgg tgaagtggtt gaaggtacga aaaagccctc ctccgacacg ccaactcacc    9360
ggctgctcta tcaggcattc ccctccattg gcggcattgt gcatacgcac tcgcgccacg    9420
ccaccatctg ggcgcaggcg ggtcagtcga ttccagcaac cggcaccacc cacgccgact    9480
atttctacgg caccattccc tgcacccgca aaatgaccga cgcagaaatc aacggcgaat    9540
atgagtggga aaccggtaac gtcatcgtag aaacctttga aaaacagggt atcgatgcag    9600
cgcaaatgcc cggcgttctg gtccattccc acggcccgtt tgcatggggc aaaaatgccg    9660
aagatgcggt gcataacgcc atcgtgctgg aagaggtcgc ttatatgggg atattctgcc    9720
gtcagttagc gccgcagtta ccggatatgc agcaaacgct gctggataaa cactatctgc    9780
gtaagcatgg cgcgaaggca tattacgggc agtaatgaca gcccgcctaa tgagcgggct    9840
tttttttcca tgaccaaaat cccttaacgt gagttttcgt tccactgagc gtcagacccc    9900
gtagaaaaga tcaaaggatc ttcttgagat ccttttttc tgcgcgtaat ctgctgcttg    9960
caaacaaaaa aaccaccgct accagcggtg gtttgtttgc cggatcaaga gctaccaact    10020 cttttccga aggtaactgg cttcagcaga gcgcagatac caaatactgt ccttctagtg    10080
tagccgtagt taggccacca cttcaagaac tctgtagcac cgcctacata cctcgctctg    10140
ctaatcctgt taccagtggc tgctgccagt ggcgataagt cgtgtcttac cgggttggac    10200
tcaagacgat agttaccgga taaggcgcag cggtcgggct gaacggggggg ttcgtgca    10258
```

The invented claimed is:

1. A method for stimulating the immune system in a patient in need thereof, comprising administering one or more antigen(s) or a nucleic acid encoding said one or more antigen(s) and an alphaviral replicase as an adjuvant, said replicase comprising an RNA dependent RNA polymerase, or a nucleic acid encoding said replicase comprising an RNA dependent RNA polymerase, wherein said method does not comprise administering nucleic acids encoding viral template RNA containing cis-signals that interact with said RNA dependent RNA polymerase and wherein the alphaviral replicase is a Semliki Forest replicase.

2. The method according to claim 1, wherein the amino acid sequence of the replicase is set forth in SEQ ID NO:1.

3. The method according to claim 2, wherein the replicase is mutated in the nsP2 region generating the mutant RRR>RDR in positions 1185-1187 of SEQ ID NO: 1.

4. The method according to claim 2, wherein the replicase is mutated in the nsP2 region generating the mutant RRR>AAA in the positions 1185-1187of SEQ ID NO: 1.

5. The method according to claim 1, wherein said replicase is encoded by an expression vector.

6. The method according to claim 5, wherein said expression vector is a DNA vector.

7. The method according to claim 6, wherein said vector is pRSV-RDR.

8. The method according to claim 1, wherein said replicase is formulated together with a pharmaceutically acceptable excipient and/or constituent.

9. The method according to claim 1, wherein said alphaviral replicase is present in a composition.

10. The method according to claim 9, wherein said composition is used for the prevention and/or treatment of an infectious disease.

11. The method according to claim 9, wherein said composition is used for the prevention and/or treatment of a bacterial disease.

12. The method according to claim 9, wherein said composition is used to treat a patient with cancer.

13. The method according to claim 9, wherein said composition is used for the prevention and/or treatment of a viral disease.

14. The method according to claim 13, wherein the patient possesses an HIV infection.

15. The method according to claim 9, wherein the composition comprises a protein-based vaccine.

16. The method according to claim 9, wherein the composition comprises a vaccine which comprises an expression vector encoding said one or more antigen(s).

17. The method according to claim 16, wherein said replicase and said one or more antigen(s) are encoded by the same expression vector.

18. The method according to claim 16 or claim 17, wherein said expression vector encoding one or more antigen(s) is a DNA vector.

19. The method according to claim 18, wherein said vector further comprises:
 (a) a DNA sequence encoding a nuclear-anchoring protein operatively linked to a heterologous promoter, said nuclear-anchoring protein comprising
   i) a DNA binding domain which binds to a specific DNA sequence, and
   ii) a functional domain that binds to a nuclear component; and
 (b) a multimerized DNA binding sequence for the nuclear anchoring protein wherein said vector lacks an origin of replication functional in mammalian cells.

20. The method according to claim 19, wherein part i) and/or part ii) is obtained from the E2 protein of the Bovine Papilloma Virus type 1.

21. The method according to claim 3, wherein said administering of an alphaviral replicase comprises administering an expression vector encoding said replicase, wherein said expression vector does not comprise viral template RNA containing cis-signals that interact with RNA dependent RNA polymerase.

22. The method according to claim 4, wherein said administering of an alphaviral replicase comprises administering an expression vector encoding said replicase, wherein said expression vector does not comprise viral template RNA containing cis-signals that interact with RNA dependent RNA polymerase.

23. The method according to claim 5, wherein said administering of an alphaviral replicase comprises administering said expression vector, wherein said expression vector does not comprise viral template RNA containing cis-signals that interact with RNA dependent RNA polymerase.

24. The method according to claim 7, wherein said administering of an alphaviral replicase comprises administering said pRSV-RDR vector, wherein said pRSV-RDR vector does not express viral template RNA containing cis-signals that interact with RNA dependent RNA polymerase.

25. The method of claim 1, wherein said administering of an alphaviral replicase comprises administering a protein comprising the alphaviral replicase.

26. The method of claim 3, wherein said administering of an alphaviral replicase comprises administering a protein comprising the alphaviral replicase.

27. The method of claim 4, wherein said administering of an alphaviral replicase comprises administering a protein comprising the alphaviral replicase.

* * * * *